US009605314B2

(12) United States Patent
Minassian et al.

(10) Patent No.: US 9,605,314 B2
(45) Date of Patent: *Mar. 28, 2017

(54) MECP2E1 GENE

(71) Applicants: The Hospital For Sick Children, Toronto (CA); Centre for Addiction and Mental Health, Toronto (CA)

(72) Inventors: Berge A. Minassian, Toronto (CA); John B. Vincent, Toronto (CA)

(73) Assignees: The Hospital for Sick Children, Toronto, Ontario (CA); Centre for Addiction and Mental Health, Toronto, Ontario (CA)

( * ) Notice: Subject to any disclaimer, the term of this patent is extended or adjusted under 35 U.S.C. 154(b) by 309 days.

This patent is subject to a terminal disclaimer.

(21) Appl. No.: 14/100,889

(22) Filed: Dec. 9, 2013

(65) Prior Publication Data
US 2014/0186834 A1 Jul. 3, 2014

Related U.S. Application Data

(63) Continuation of application No. 12/657,559, filed on Jan. 21, 2010, now Pat. No. 8,637,236, which is a continuation-in-part of application No. 11/352,153, filed on Feb. 9, 2006, now Pat. No. 7,670,773, which is a continuation of application No. PCT/CA2005/000198, filed on Feb. 17, 2005.

(60) Provisional application No. 60/544,311, filed on Feb. 17, 2004.

(51) Int. Cl.
*C12Q 1/68* (2006.01)
*C07K 14/47* (2006.01)
*G01N 33/68* (2006.01)
*A61K 38/00* (2006.01)
*A61K 48/00* (2006.01)

(52) U.S. Cl.
CPC ............ *C12Q 1/6883* (2013.01); *C07K 14/47* (2013.01); *G01N 33/6896* (2013.01); *A61K 38/00* (2013.01); *A61K 48/00* (2013.01); *C12Q 2600/156* (2013.01); *G01N 2500/00* (2013.01); *G01N 2800/28* (2013.01)

(58) Field of Classification Search
None
See application file for complete search history.

(56) References Cited

U.S. PATENT DOCUMENTS

| 6,709,817 | B1 | 3/2004 | Zoghbi et al. |
| 7,670,773 | B2 | 3/2010 | Minassian et al. |
| 2002/0137067 | A1 | 9/2002 | Beaudet et al. |
| 2003/0082606 | A1 | 5/2003 | Lebo et al. |
| 2005/0227229 | A1 | 10/2005 | Lebo et al. |
| 2006/0194257 | A1 | 8/2006 | Minassian et al. |
| 2009/0098565 | A1 | 4/2009 | Minassian et al. |

FOREIGN PATENT DOCUMENTS

| JP | 2001-292775 | 10/2001 |
| WO | WO 02/068579 A2 | 9/2002 |
| WO | WO 2005/078099 A1 | 8/2005 |

OTHER PUBLICATIONS

Office Action for Japanese Application No. 2006-553398, Mail Date: Aug. 4, 2010.
Office Action for U.S. Appl. No. 12/313,251, Mail Date: Sep. 1, 2010.
Liu, J. and G. Baynam, "Cornelia deLange Syndrome," *Adv. Exp. Med. Biol.* 685: 111-123, Abstract (2010) (month not available).
de Brouwer, A.P., et al., "PRPS1 Mutations: Four Distinct Syndromes and Potential Treatment," *Am. J. Hum. Genet.*, 86: 506-518, Abstract (Apr. 2010).
Office Action, U.S. Appl. No. 12/313,251; Mail Date: Jul. 24, 2012.
Office Action for U.S. Appl. No. 11/352,153, dated May 3, 2007.
Office Action for U.S. Appl. No. 11/352,153, dated Nov. 30, 2007.
Office Action for U.S. Appl. No. 11/352,153, dated May 2, 2008.
Office Action for U.S. Appl. No. 11/352,153, dated Oct. 2, 2008.
Office Action for U.S. Appl. No. 11/352,153, dated Dec. 30, 2008.
Office Action for U.S. Appl. No. 11/352,153, dated Jul. 31, 2009.
Office Action for U.S. Appl. No. 11/352,153, dated Oct. 20, 2009.
Office Acton for U.S. Appl. No. 12/313,251, dated Mar. 18, 2010.
Schollen, et al., "Gross Rearrangements in the MECP2 Gene in Three Patients with Rett Syndrome: Implications for Routine Diagnosis of Rett Syndrome," *Human Mutation*, vol. 22, pp. 116-120 (2003).
Office Action for U.S. Appl. No 12/313,251, dated Feb. 22, 2011.
Final Office Action U.S. Appl. No. 12/313,251, dated Oct. 21, 2011.
Office Action U.S. Appl. No. 12/313,251, dated Feb. 1, 2012.
Bloecker, H., et al., Accession No. BX538060, Genbank Database, [online] Jun. 17, 2003, [retrieved on May 17, 2006] retrieved from the Internet http://www.ncbi.nlm.nih.gov/entrez/viewer.fcgi?db=nucleotide&val=31874178.
Bloecker, H., et al., Access on No. CAD97991, Genpept Database, [online] Jun. 17, 2003, [retrieved on May 17, 2006] retrieved from the Internet http://www.ncbi.nlm.nih.gov/enterez/viewerfcgi?db=protein&val-31874179.
Kass, S.U., et al., Accession No. AF051768, Genbank Database [online] Jan. 5, 1999 [retrieved on May 17, 2006] retrieved from the Internet http: //www. ncbi .n 1 m nih.gov/entrez/viewer.fcgi?db=nucleotide&val=4105998.
Kass, S.U., et al, Accession No. AAD02651, Genpept Database, [online] Jan. 5, 1999 [retrieved on May 17, 2006] retrieved from the Internet http:/www.ncbi_.nlm_.nih._gov/entreevi ewer Segi?db=protein&val=4105999.

(Continued)

Primary Examiner — Ileana Popa
(74) Attorney, Agent, or Firm — Foley & Lardner LLP

(57) ABSTRACT

The invention is a novel MECP2E1 splice variant and its corresponding polypeptide. The invention also includes methods of using these nucleic acid sequences and proteins in medical diagnosis and treatment of neuropsychiatric disorders or development disorders.

7 Claims, 6 Drawing Sheets

(56) References Cited

OTHER PUBLICATIONS

Coenraads, M., "Researchers Confirm Novel Form of the Rett Syndrome Protein," Rett Syndro Research Foundation: Press Releases: Mar. 22, 2004, pp. 1-2, [retrieved on May 17, 2006] Retrieved from the Internet http://www.rsrforg/about_rsrf/1.5.2.html.

Chen, R. Z., et al., "Deficiency of Methyl-CpG Binding Protein-2 in CNS Neurons Results in a Rett-like Phenotype in Mice," Nature Genetics, 27: 327-331 (2001).

Kriaucionis, S., et al., "The Major Form of MeCP2 has a Novel N-terminus Genera ed by Alternative Splicing," Nucleic Acids Research, 32(5): 1818-1823 (2004).

Evans, J. C., et al., "Variation in Exon 1 Coding Region and Promotor of MECP2 in Rat Syndrome and Controls," European Journal of Human Genetics, 13: 124-126 (2005).

Kim, S., et al., Novel de novo Nonsense Mutation of MECP2 in a Patient with Rett S Human Mutation, Mutation in Brief #307 Online (2000).

Erlandson, A., et al., "Multiplex Ligation-Dependent Probe Amplification (MLPA) Detects Large Deletions in the MECP2 Gene of Swedish Rett Syndrome Patients," Genetic Testing, 7(4): 329-332 (2003).

Bienvenu, T., et al., "MECP2 Mutations Account for most Cases of Typical Forn s of Rett Syndrome," Human Molecular Genetics, 9(9): 1377-1384 (2000).

Nicolao, P., et al., "DHPLC Analys s of the MECP2 Gene in Italian Rett Patients," Human Mutation, 18: 132-140 ( 2001).

Mnatzakanian, G. N., et al, "A Previously Unidentified MECP2 Open Reading Frame Defines a New Protein Isoform Relevant to Rett Syndrome," Nature Genetics, 36(4): 339-341 (2004).

Vacca, M., et al. "Mutation Analysis of the MECP2 Gene in British and Italian Rett Syndrome Fales," J. Mot Med., 78: 648-655 (2001).

Cheadle, J. P., et al., "Long-Read Sequence Analysis of the MECP2 Gene in Rett Syndrome Patients: Correlation of Disease Severity with Mutation Type and Location," Human Molecular Genetics, 9(7): 1119-1129 (2000).

Bourdon, V., et al., "A Detailed Analysis of the MECP2 Gene: Prevalence of Recurrent Mutations and Gross DNA Rearrangements in Rett Syndrome Patients," Hum. Genet. 108: 43-50 (2001).

Charman, T., et al., "Dimensional Phenotypic Analysis and Functional Categorisation of Mutations Reveal Novel Genotype-Phenotype Associations in Rett Syndrome," European Journal of Human Genetics, 13: 1121-1130 (2005).

Christodoulou, J., et al., "RettBASE: The USA MECP2 Variation Database—A New Mutation Database in Evolution," Human Mutation, 21: 466-472 (2003).

Amir, R. E., et al., "Rett Syndrome is Caused by Mutations in X-Linked MECP2, Encoding Methyl-CpG-Binding Protein 2," Nature Genetics, 23: 185-188 (1999).

Willard, H. F. and Hendrich, B.D., "Breaking the Silence in Rett Syndrome," Nature Genetics, 23: 27-128 (1999).

Buyse, I. M. and Hendrich, B.D., "Diagnostic Testing for Rett Syndrome by DHPLC and Direct Sequencing Analysis of the MECP2 Gene: Identification of Several Novel Mutations and Polymorphisms," Am. J. Hum. Genet., 67: 1428-1436 (2000).

Thistlethwaite, W. A., et al., "Rapid Genotyping of Common MeCP2 Mutations with an Electronic DNA Microchip Using Serial Differential Hybridization," Journal of Molecular Diagnostics, 5(2): 21-126 (2003).

Hammer, S., et al., "The Phenotypic Consequences of MECP2 Mutations Extend Beyond Rett Syndrome," Mental Retardation and Developmental Disabilities Research Reviews, 8: 94-98 (2002).

Meloni, I., et al., "A Mutation in the Rat Syndrome Gene, MECP2, Causes X-Linked Mental Retardation and Progressive Spasticity in Males," Am. .1 I-Turn. Genet., 67: 982-985 ( 2000).

Samaco, R. C., et al., "Multiple Pathways Regula c McCP2 Expression in Normal Brain Development and Exhibit Defects in Autism-Spectrum Disorders," Human Molecular Genetics, 3(6): 629-639 (2004).

Beyer, K. S., et al. "Mutation Analysis Analysis of the Coding Sequence of the MECP2 Gene in Infantile Autism," Hum. Genet., 111: 305-309 (2002).

Shi, J., et al., Detection of Heterozygous Deletions and Duplications in the MECP2 Gene in Rett Syndrome by Robust Dosage PCR (RD-PCR), Human Mutation, Mutation in Brief #809 Online, 7 pages (2005).

Fyfe, S., et al., "InterRett and RettBASE: International Rett Syndrome Association Da abases for Rett Syndrome," Journal of Child Neurology, 18: 709-713 (Oct. 2003).

Archer, H. L., et al., "Gross Rearrang ments of the MECP2 Gene are Found in Both Classical an Atypical Rett Syndrome Patients," J Med. Genet., 43: 451-456 (2006).

Van Esch, H., et al., "Duplication of the MECP2 Region is a Frequent Cause of Severe Mental Retardation and Progressive Neurological Systems in Males," Am. J. Hum. Genet., 77: 442-453 (Jul. 2005).

Boulanger, S., et al., "Evaluation of the Multiplex Ligation-Dependent Probe Amplification (MLPA) Technology in the Diagnosis of Rett Syndrome," Am. J. Hum. Genet., 73 (5): 572 (Nov. 2003).

Aber, K. M., et al., "Methly-CpG-Binding Protein 2 is Localized in the Postsynapt c Compartment: An Immunchemical Study of Subcellular Fractions," Neuroscience, 116: 77-80 (2003).

Bienvenu, T., et al., "ARX, A Novel Prd-class-homeobox Gene Highly Expressed in the Telencephalon, Is Mutated in X-linked Mental Retardation," Ilum. Mal. Gen., 11(8): 981-991 (2002).

Brown, L. Y. and Brown, S. A., "Alanine Tracts: The Expanding Story of Human Illness and Trinucleotide Repeats," Trends Genet . . . , 20(1): 51-58 (2004).

Cohen, D., et al., 1 VIECP2 Mutation in a Boy With Language Disorder and Schizophrenia, A Psychiatry, Letters to the Editor, 159(1): 148-149 (Jan. 2002).

Collins, A. L., et al., "Mild Overexpression of MeCP2 Causes a Progress ve Neurological Disorder in Mice," Hum. Mol. Gen., 13(21): 2679-2689 (Sep. 2004).

Coy, J. F., et al., "A Complex Pattern of Evolutionary Conservation and Alternative Polyadenylation within the Long 3'-Untranslated Region of the Methyl-CpG-Binding Protein 2 Gene (MeCP2) Suggests a Regulatory Role in Gene Expression," Hum. Mol. Genetics, 8(7): 1253-1262 (1999).

D'Esposito, M., et al., "Isolation, Physical Mapping and Northern Analysis of the X-Linked Human Gene Encoding Methyl CpG-Binding Protein, MECP2," Mamm. Genorne., 7, 533-535 (1996).

Gronskov, K., et al., "Screening of the ARX Gene in 682 Retarded Males," Eur. J. Hum. Genet., 12: 701-705 (Jun. 2004).

Hagberg, B., "Clinical Manifestations and Stages of Rett Syndrome," Mental Retardation and Developmental Disabilities Research Reviews, 8:61-65 (2002, month not available).

Hardingham, G. E., et al., "A Calcium Microdomain Near NMDA Receptors: On Switch for ERK-dependent Synapse-to-Nucleus Communication," Nature Neuroscience, 4(6): 565-566 (Jun. 2001).

Inoue, K. and Keegstra, K., "A Polyglycine Stretch is Necessary for Proper Targeting of the Protein Translocation Channel Precursor to the Outer Envelope Membrane of Chloroplasts," The Plant Journal, 34: 661-669 (2003).

Miltenberger-Miltenyi, G. and Laccone, F., "Mutations and Polymorphisms in the Human Methyl CpG-Binding Protein MECP2," Human Mutation, 22:107-115 (2003).

Orrico, A., et al., "M_ECP2 Mutation in Male Patients with Non-specific X-linked Mental Retardation," FEBS Letters, 481: 285-288 (2000).

Reichwald, K., et al., "Comparative Sequence Analysis of the MECP2-Locus in Human and Mouse Reveals New Transcribed Regions," Mamm, Genorne., 11: 182-190 (2000).

Schouten, J. P., et al., "Relative Quantification of 40 Nucleic Acid Sequences by Multiplex Ligation-Dependent Probe Amplification," Nucleic Acids Research, 30(12): e57, 13 pages (2002).

Shahbazian, M. D., et al., "Insight into Rett Syndrome: MeCP2 Levels Display Tissue-and-Cell-Specific Differences and Correlate with Neuronal Maturation," Hum. Mol. Gene., 11(2): 115-124 (2002).

(56) References Cited

OTHER PUBLICATIONS

Stancheva, I., et al., "A Mutant form of McCP2 Protein Associated with Human Rett Syndrome Cannot Be Displaced from Methylated DNA by Notch in *Xenopus* Embryos," *Ilifol. Cell.*, 12: 425-435 (2003).

Utsch, B., et al., "A Novel Stable Polyalanine [Poly(A)] Expansion in the *HOXA13* Gene Associated with Hand-Foot-Genital Syndrome: Proper Function of Poly(A)-Harbouring Transcription Factors Depends on a Critical repeat Length?," *Hum. Genet.* 110:488-494 (Apr. 2002).

Muhle, R., et al., "The Genetics of Autism," *Pediatrics*, 113:472-486 (May 2004).

Kato, M., "A New Paradigm for West Syndrome Based on Molecular and Cell Biology," *Epilepsy Research*, 70:S87-S95 (2006).

Abdolma eky, H.M. et al., "Genetics and Epigenetics in Major Psychiatric Disorders: Dilemmas, Achievements, Applications, and Future Scope," *Am. J. Pharmacogenomics*, 5:149-160 (2005).

Hardy, J., and Gwinn-Hardy, K., Genetic Classification of Primary Neurodegenerative Disease, *Science*, 282:1075-1079 (1998).

Amir, R.E., et al., "Mutations in Exon 1 of *MECP2* are a Rare Cause of Rett Syndrome" *J. Med. Genet.* 42: e15, 4 pages (2005).

Kleefstra, T., et al., "*MECP2* Analysis in Mentally Retarded Patients: Implications for Routine DNA Diagnostics" *Eur. J. Hum. Genet.* 12:24-28 (2004).

Mnatzakanian, G.N., et al., "A Previously Unidentified *MECP2* Open Reading Frame Defines a New Protein Isoform Relevant to Rett Syndrome," *Nat. Genet.* 36: 339-341 (2004).

Peippo, M.M., et al., "Pitt-Hopkins Syndrome in Two Patients and Further Definition of the Phenotype," *Clinical Dysmorphology*, 15: 47-54 (2006).

Poirier, K., et al., "Mutations in Exon 1 of *MECP2B* are not a Common Cause of X-Linked Mental Retardation in Males," *European J. Hum. Genet.* 13:523-524 (2005).

Ylisaukko-ojo, T., et a ., "MECP2 Mutation Analysis in Pat ents with Mental Retarda ion," *Am. I Med. Genet.* 132A: 121-124 (2005).

Notification of Transmittal of the International Search Report and the Written Opinion of the International Searching Authority, or the Declaration for International Application No. PCT/CA2005/000198, Mail Date: Jul. 4, 2005.

International Preliminary Report on Patentability for International Applica ion No. PCT/CA2005/000198, Mail Date: Aug. 31, 2006.

Office Action for U.S. Appl. No. 11/352,153, Mail Date: Nov. 29, 2006.

Yusufazai et al., "Functional consequences of Rett syndrome mutations of human MeCP2," *Nucleic Acids Research*, vol. 28, No. 21, pp. 4172-4179 (2000).

U.S. Office Action issued in related U.S. Appl. No. 12/313,251, dated Feb. 4, 2014.

U.S. Office Action issued in related U.S. Appl. No. 12/313,251, dated Apr. 22, 2015.

Japanese Notice of Reasons for Rejection issued in related Japanese Patent Application No. 2006-553398, dated Jan. 28, 2015.

Notice of Reasons for Rejection Issued in related Japanese Patent Application No. 2006-553398, dated Apr. 28, 2014.

Optiz, Am. J. Med. Genet. vol. 130B, No., Sep. 15, 2004, p. 104 [Abstract].

Office Action issued in related U.S. Appl. No. 12/313,251, dated Aug. 27, 2015.

Sawada, et al., "Detection of Triplet Repeat Expansion in the Human Genome by Use of Hybridization signal Intensity," *Analytical Biochemistry*, vol. 286, pp. 59-66 (2000).

Office Action issued in related U.S. Appl. No. 12/313,251, dated Jan. 13, 2016.

Office Action issued in related U.S. Appl. No. 12/313,251, dated Jul. 6, 2016.

Database GenBank [online], Accession No. NM_004992 http://www.ncbi.nlm.nih.gov/sviewer/viewer.fcgi?val=7710148 &sat=OLD03&satkey=6827913 Dec. 21, 2003 uploaded, Leonard, H. et al., Definition: *Homo sapiens* methyl CpG binding protein 2 (Rett syndrome) (MECP2), mRNA. [retrieved on Jul. 27, 2010].

Notice of Reasons for Rejection issued in related Japanese Patent Application No. 2015-147517, dated Jun. 23, 2016.

Notice of Allowance issued in related U.S. Appl. No. 12/313,251, dated Sep. 30, 2016.

A.

B.

C.

A

MECP2E1 GENE

RELATED APPLICATIONS

This application is a continuation of U.S. patent application Ser. No. 12/657,559, filed Jan. 21, 2010, which is a continuation-in-part of U.S. patent application Ser. No. 11/352,153, filed Feb. 9, 2006, now U.S. Pat. No. 7,670,773, which is a continuation of International Patent Application No. PCT/CA2005/000198 which designated the United States and was filed on Feb. 17, 2005, which claims the benefit of U.S. Provisional Patent Application No. 60/544,311, filed on Feb. 17, 2004. The contents of the above applications are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Feb. 28, 2014, is named 103779-0609 SL.txt and is 154,492 bytes in size.

BACKGROUND OF THE INVENTION

Neuropsychiatric disorders account for six of the ten highest impact diseases worldwide, according to the World Health Organization. Cost to the US economy is $100 billion—one of every four persons entering physician offices has a diagnosable mental disorder.

Rett syndrome (RTT) (OMIM #312750) is characterized by onset, in girls, of a gradual slowing of neurodevelopment in the second half of the first year of life towards stagnation by age four, followed by regression and loss of acquired fine motor and communication skills. A pseudostationary period follows during which a picture of preserved ambulation, aberrant communication and stereotypic hand wringing approximates early autism. Regression, however, remains insidiously ongoing and ultimately results in profound mental retardation.

Up to 80% of patients with RTT have mutations in exons 3 and 4 of the 4-exon MECP2 gene (FIG. 1a) encoding the MeCP2 transcriptional repressor. Mutations in the remaining 20% of patients has remained elusive. In the known transcript of the gene all four exons are utilized, the translation start site is in exon 2, and exon 1 and most of exon 2 form the 5' untranslated region (UTR). For clarity, this transcript is named MECP2E2 (previously MECP2A), and its encoded protein MeCP2E2 (previously MeCP2A).

No mutation specific to the MeCP2E2-defining exon 2 has been found to date despite several hundred patients analyzed for mutations in this exon. These studies did not include exon 1 as it was considered non-coding.

Non-inactivating MECP2 mutations have also been associated with phenotypes that overlap RTT such as mental retardation and autism. There is a need for the identification of further mutations to account for the remaining 20% of RTT patients so that methods of diagnosing and treating RTT can be identified.

Mutations in the Rett syndrome gene, MECP2, have also been found among autism patients as well as in patients with childhood onset psychosis, Angelman syndrome, non-syndromic mental retardation and neo-natal encepalopathy, demonstrating that there may be diverse phenotypic consequences of mutations in MECP2.

SUMMARY OF THE INVENTION

The present inventors have identified a novel open reading frame of the MECP2 gene, that is called MECP2E1. Inspection of the 5'UTR revealed that, whereas exon 2 has a number of in-frame stops upstream of the ATG, exon 1 contains an open reading frame across its entire length including an ATG. This open reading frame encodes a transcript composed of exons 1, 3 and 4 of the MECP2 gene. MECP2E1 is similar to MECP2E2 (GenBank accession # NM_004992, SEQ ID NO. 1, except with nucleotides 71-193 absent, corresponding to the splicing out of exon 2.

Accordingly, the present invention provides an isolated nucleic acid molecule comprising a sequence encoding the MeCP2E1 protein. The invention also includes the corresponding polypeptide, MeCP2E1.

In one embodiment, the purified and isolated nucleic acid molecule comprises
(a) a nucleic acid sequence encoding a protein as shown in SEQ ID No. 4;
(b) a nucleic acid sequence complementary to (a);
(c) a nucleic acid sequence that has substantial homology to (a) or (b);
(d) a nucleic acid sequence that is an analog to a nucleic acid sequence of (a), (b), or (c);
(e) a fragment of (a) to (d) that is at least 15 bases, preferably 20 to 30 bases, and which will hybridize to a nucleic acid sequence of (a), (b), (c) or (d) under stringent hybridization conditions; or
(f) a nucleic acid molecule differing from any of the nucleic acids of (a) to (c) in codon sequences due to the degeneracy of the genetic code.

In a specific embodiment of the invention, an isolated nucleic acid molecule is provided having a sequence as shown in SEQ ID No. 3 or a fragment or variant thereof.

The inventors have found that patients with a neuropsychiatric disorder or developmental disorder such as Rett's syndrome and mental retardation, had mutations in exon 1 of the MECP2E1 gene. Accordingly, the present invention provides a method of detecting a neuropsychiatric disorder or developmental disorder comprising detecting a mutation or deletion in exon 1 of the MECP2E1 sequence (SEQ ID No. 3). A mutation can be detected by sequencing PCR products from genomic DNA using primers X1F/X1R: mutation screening primers (FIG. 1). Detection of insertion or deletion mutations may require the cloning of the PCR product into a suitable plasmid vector, followed by transfection into *E. Coli*, and sequencing of clones from isolated colonies. Alternatively, a mutation can be detected by multiple ligation-dependent probe amplification (MLPA) using 20 probe pairs that target the four MECP2 exons, six X-linked control regions and ten autosomal control regions. A mutation or deletion can also be detected by assaying for the protein product encoded by MECP2E1.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The patent or application file contains at least one drawing executed in color. Copies of this patent or patent application publication with color drawings will be provided by the Office upon request and payment of the necessary fee.

The invention will now be described in relation to the drawings in which:

FIG. 5 discloses SEQ ID NOS 18 and 47-55, respectively, in order of appearance.

DETAILED DESCRIPTION OF THE INVENTION

Figure 1:
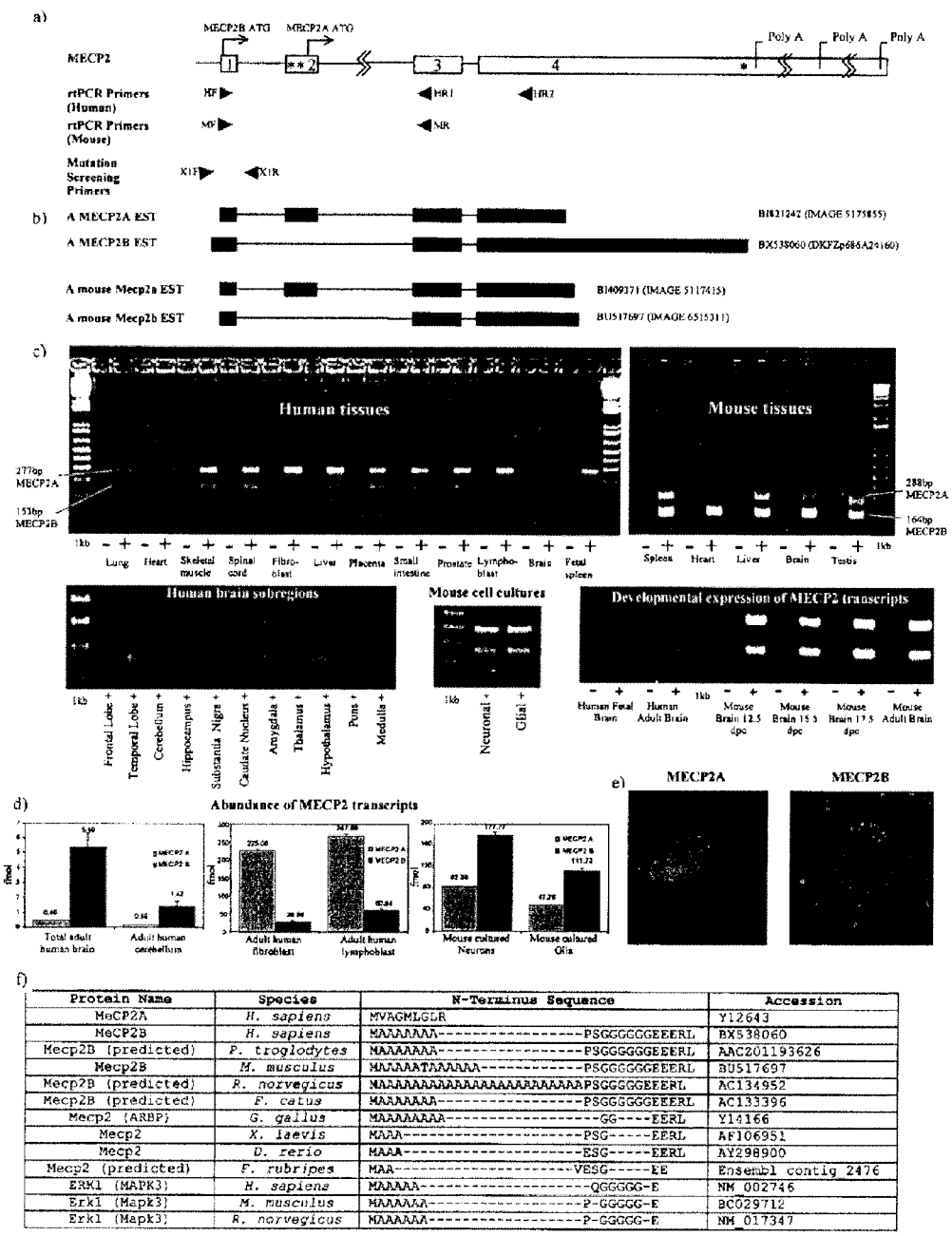
FIG. 1 shows MECP2 5' splice variants. a) Structure of the MECP2 gene. Numbered boxes indicate exons; asterisks indicate in-frame stop codons. In the traditional MECP2E2 splice variant, the start codon is in exon 2. In MECP2E1, exon 2 is not present and the start codon is in exon 1. HF/HR1 and MF/MR: human and mouse primer pairs used in the rtPCR experiments shown in panel c. HR2: a second human reverse primer, which confirms the results obtained with HR1(data not shown). X1F/X1R: mutation screening primers (see FIG. 2). Primer sequences (5'-3'): HF-ctcggagagagggctgtg (SEQ ID No. 5), HR1-cttgagggggtttgtccttga (SEQ ID No. 6), HR2-cgtttgatcaccatgacctg (SEQ ID No. 7), MF-aggaggcgaggaggagagac (SEQ ID No. 8), MR-ctggctctgcagaatggtg (SEQ ID No. 9), X1F-ccatcacagccaatgacg (SEQ ID No. 19), X1R-aggggggagggtagagaggag (SEQ ID No. 20). b) Examples of MECP2 ESTs. c) PCR results using primers in (a) (HF/HR1 and MF/MR) on cDNA from indicated adult tissues (except where indicated otherwise) and cell cultures; d.p.c.: days postcoitum. d) Transcript-specific real-time quantitative PCR (SYBR Green detection method) on cDNA from indicated tissues or cell cultures. e) 3'myc-tagged MeCP2E1 (and MeCP2E2) localize principally in the nucleus, and in indeterminate puncti in the cytoplasm. f) N-termini of indicated proteins (SEQ ID NOS 30-42, respectively, in order of appearance); dashes represent no amino acids.

The present inventors have identified a MECP2 splice variant that contributes to new coding sequence that may contain mutations in patients with neuropsychiatric disorders such as Rett's syndrome and mental retardation.

I. Nucleic Acid Molecules of the Invention

As hereinbefore mentioned, the present invention relates to isolated MECP2E1 nucleic acid molecules. The term "isolated" refers to a nucleic acid substantially free of cellular material or culture medium when produced by recombinant DNA techniques, or chemical precursors, or other chemicals when chemically synthesized.

The term "nucleic acid" is intended to include DNA and RNA and can be either double stranded or single stranded. The term is also intended to include a strand that is a mixture of nucleic acid molecules and nucleic acid analogs and/or nucleotide analogs, or that is made entirely of nucleic acid analogs and/or nucleotide analogs.

Broadly stated, the present invention provides an isolated nucleic acid molecule containing a sequence encoding the MECP2E1 transcript of the MECP2 gene. Accordingly, the present invention provides an isolated nucleic acid molecule containing a sequence encoding MECP2E1 shown in SEQ ID No. 4 or a fragment, variant, or analog thereof.

In one embodiment, the purified and isolated nucleic acid molecule comprises (a) a nucleic acid sequence encoding a MECP2E1 protein as shown in SEQ ID No. 4;

(b) a nucleic acid sequence complementary to (a);

(c) a nucleic acid sequence that has substantial homology to (a) or (b);

(d) a nucleic acid sequence that is an analog to a nucleic acid sequence of (a), (b), or (c);

(e) a fragment of (a) to (d) that is at least 15 bases, preferably 20 to 30 bases, and which will hybridize to a nucleic acid sequence of (a), (b), (c) or (d) under stringent hybridization conditions; or (f) a nucleic acid molecule differing from any of the nucleic acids of (a) to (c) in codon sequences due to the degeneracy of the genetic code.

In a specific embodiment of the invention, the isolated nucleic acid molecule has a sequence as shown in SEQ ID No. 3 or a fragment or variant thereof.

The term "MECP2E1" means an isoform of the MECP2 gene that contains exons 1, 3 and 4 but lacks exon 2. This gene was previously referred to as MECP2B but is now called MECP2E1 indicating the translation start site in exon one. The term "MECP2E1" includes the nucleic acid sequence as shown in SEQ ID No. 3 as well as mutations, variants and fragments thereof that are associated with neuropsychiatric disorders and developmental disorders. "MECP2E1" can also be referred to as "MECP2_e1." The "MeCP2E1" protein can also be referred to as "MeCP2_e1." MECP2E2 is the transcript of the gene that contains exons 1, 2, 3 and 4. "MECP2E2" can also be referred to as "MECP2_e2." The "MeCP2E2" protein can also be referred to as "MeCP2_e2."

It will be appreciated that the invention includes nucleic acid molecules encoding truncations of the MeCP2E1 proteins of the invention, and analogs and homologs of the MeCP2E1 proteins of the invention and truncations thereof, as described below.

Further, it will be appreciated that the invention includes nucleic acid molecules comprising nucleic acid sequences having substantial sequence homology with the nucleic acid sequences of the invention and fragments thereof. The term "sequences having substantial sequence homology" means those nucleic acid sequences which have slight or inconsequential sequence variations from these sequences, i.e. the sequences function in substantially the same manner to produce functionally equivalent proteins. The variations may be attributable to local mutations or structural modifications.

Generally, nucleic acid sequences having substantial homology include nucleic acid sequences having at least 70%, preferably 80-90% identity with the nucleic acid sequences of the invention.

Sequence identity is most preferably assessed by the algorithm of the BLAST version 2.1 program advanced search (BLAST is a series of programs that are available online at www.ncbi.nlm.nih gov/BLAST. The advanced blast search (www.ncbi.nlm.nih.gov/blast/blast.cgi?J-form=1) is set to default parameters. (i.e. Matrix BLOSUM62; Gap existence cost 11; Per residue gap cost 1; Lambda ratio 0.85 default).). For example, if a nucleotide sequence (called "Sequence A") has 90% identity to a portion of the nucleotide sequence in SEQ ID No. 3, then Sequence A will be identical to the referenced portion of the nucleotide sequence in SEQ ID No. 3, except that Sequence A may include up to 10 point mutations, such as substitutions with other nucleotides, per each 100 nucleotides of the referenced portion of the nucleotide sequence in SEQ ID No. 3. Nucleotide sequences functionally equivalent to the MECP2E1 transcript can occur in a variety of forms as described below.

The term "a nucleic acid sequence which is an analog" means a nucleic acid sequence which has been modified as compared to the sequence of (a), (b) or (c) wherein the modification does not alter the utility of the sequence as described herein. The modified sequence or analog may have improved properties over the sequence shown in (a), (b) or (c). One example of a modification to prepare an analog is to replace one of the naturally occurring bases (i.e. adenine, guanine, cytosine or thymine) of the sequence shown in SEQ ID No. 3, with a modified base such as such as xanthine, hypoxanthine, 2-aminoadenine, 6-methyl, 2-propyl and other alkyl adenines, 5-halo uracil, 5-halo cytosine, 6-aza uracil, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8 amino guanine, 8-thiol guanine, 8-thiolalkyl guanines, 8-hydroxyl guanine and other 8-substituted guanines, other aza and deaza uracils, thymidines, cytosines, adenines, or guanines, 5-trifluoromethyl uracil and 5-trifluoro cytosine.

Another example of a modification is to include modified phosphorous or oxygen heteroatoms in the phosphate backbone, short chain alkyl or cycloalkyl intersugar linkages or short chain heteroatomic or heterocyclic intersugar linkages in the nucleic acid molecule shown in SEQ ID No. 3. For example, the nucleic acid sequences may contain phosphorothioates, phosphotriesters, methyl phosphonates, and phosphorodithioates.

A further example of an analog of a nucleic acid molecule of the invention is a peptide nucleic acid (PNA) wherein the deoxyribose (or ribose) phosphate backbone in the DNA (or RNA), is replaced with a polyamide backbone which is similar to that found in peptides (P. E. Nielsen, et al Science 1991, 254, 1497). PNA analogs have been shown to be resistant to degradation by enzymes and to have extended lives in vivo and in vitro. PNAs also bind stronger to a complimentary DNA sequence due to the lack of charge repulsion between the PNA strand and the DNA strand. Other nucleic acid analogs may contain nucleotides containing polymer backbones, cyclic backbones, or acyclic backbones. For example, the nucleotides may have morpholino backbone structures (U.S. Pat. No. 5,034,506). The analogs may also contain groups such as reporter groups, a group for improving the pharmacokinetic or pharmacodynamic properties of nucleic acid sequence.

Another aspect of the invention provides a nucleic acid molecule, and fragments thereof having at least 15 bases, which hybridizes to the nucleic acid molecules of the invention under hybridization conditions. Such nucleic acid molecules preferably hybridize to all or a portion of MECP2E1 or its complement under stringent conditions as defined herein (see Sambrook et al. (most recent edition) Molecular Cloning: A Laboratory Manual, Cold Spring Harbor Laboratory Press, Cold Spring Harbor, N.Y.; Ausubel et al. (eds.), 1995, Current Protocols in Molecular Biology, (John Wiley & Sons, NY)). The portion of the hybridizing nucleic acids is typically at least 15 (e.g. 20, 25, 30 or 50) nucleotides in length. The hybridizing portion of the hybridizing nucleic acid is at least 80% e.g. at least 95% or at least 98% identical to the sequence or a portion or all of a nucleic acid encoding a MeCP2E1 polypeptide, or its complement. Hybridizing nucleic acids of the type described herein can be used, for example, as a cloning probe, a primer (e.g. a PCR primer) or a diagnostic probe. Hybridization of the oligonucleotide probe to a nucleic acid sample typically is performed under stringent conditions. Nucleic acid duplex or hybrid stability is expressed as the melting temperature or Tm, which is the temperature at which a probe dissociates from a target DNA. This melting temperature is used to define the required stringency conditions. If sequences are to be identified that are related and substantially identical to the probe, rather than identical, then it is useful to first establish the lowest temperature at which only homologous hybridization occurs with a particular concentration of salt (e.g. SSC or SSPE). Then, assuming that 1% mismatching results in a 1 degree Celsius decrease in the Tm, the temperature of the final wash in the hybridization reaction is reduced accordingly (for example, if sequences having greater than 95% identity with the probe are sought, the final wash temperature is decreased by 5 degrees Celsius). In practice, the change in Tm can be between 0.5 degrees Celsius and 1.5 degrees Celsius per 1% mismatch. Low stringency conditions involve hybridizing at about: 1×SSC, 0.1% SDS at 50° C. High stringency conditions are: 0.1×SSC, 0.1% SDS at 65° C. Moderate stringency is about 1×SSC 0.1% SDS at 60 degrees Celsius. The parameters of salt concentration and temperature can be varied to achieve the optimal level of identity between the probe and the target nucleic acid.

Isolated and purified nucleic acid molecules having sequences which differ from the nucleic acid sequence shown in SEQ ID No. 3 due to degeneracy in the genetic code are also within the scope of the invention. The genetic code is degenerate so other nucleic acid molecules, which encode a polypeptide identical to the MeCP2E1 amino acid sequence SEQ ID No. 3 may also be used.

The present invention also includes mutated forms of MEC2P2E1 associated with a neuropsychiatric disorder or developmental disorder including the specific mutations listed in Table 1. Specifically, the following mutations are associated with Rett's syndrome: (1) an 11 bp deletion in nucleotides 38 to 54 shown in SEQ ID No. 1; (2) a deletion of exon 1 containing nucleotides 1-69 shown in SEQ ID No. 1; (3) an adenine to thymine change at nucleotide position 8 shown in SEQ ID No. 1; (4) a deletion in the sequence TG at nucleotide positions 70-71 in SEQ ID No. 1 (5) an adenine to guanine change at nucleotide position 8 shown in SEQ ID No. 1; (6) a cytosine to thymine change at nucleotide position 12 shown in SEQ ID No. 1; and (7) a deletion in the sequence TG at nucleotide positions 69 and 70 in SEQ ID No. 1.

The following mutations are associated with developmental delay: (1) an insertion of one or more copies of the trinucleotide sequence GCC between nucleotides 11 and 29 shown in SEQ ID No. 1; (2) a deletion of one or more copies of the trinucleotide sequence GCC between nucleotides 11 and 29 shown in SEQ ID No. 1; (3) an insertion of the nucleotide sequence GGA between nucleotides 38 and 54 shown in SEQ ID No. 1; (4) a deletion of the nucleotide sequence GC at nucleotides −38 and −39 upstream of nucleotide 1 shown in SEQ ID No. 1; and (5) a deletion of the nucleotide sequence AG at nucleotides −19 and −20 upstream of nucleotide 1 shown in SEQ ID No. 1.

With respect to mutations (4) and (5) in the developmental delay group, these are upstream of nucleotide 1 shown in SEQ ID No. 1 GenBank Accession number BX538060 has the upstream sequences. Therefore, for greater clarity mutation (4), that consists of a deletion of the nucleotide sequence GC at nucleotides −38 and −39, corresponds to nucleotides 11-12 of sequence BX538060; and mutation (5), that consists of a deletion of the nucleotide sequence AG at nucleotides −19 and −20, corresponds to nucleotides 30-31 of BX538060.

Nucleic acid molecules from MECP2E1 can be isolated by preparing a labeled nucleic acid probe based on all or part of the nucleic acid sequences as shown in SEQ ID No. 3, and using this labelled nucleic acid probe to screen an appropriate DNA library (e.g. a cDNA or genomic DNA library). Nucleic acids isolated by screening of a cDNA or genomic DNA library can be sequenced by standard techniques. Another method involves comparing the MECP2E1 sequence to other sequences, for example using bioinformatics techniques such as database searches or alignment strategies, and detecting the presence of a MECP2E1 nucleic acid sequence.

Nucleic acid molecules of the invention can also be isolated by selectively amplifying a nucleic acid using the polymerase chain reaction (PCR) methods and cDNA or genomic DNA. It is possible to design synthetic oligonucleotide primers from the nucleic acid molecules as shown in SEQ ID No. 3 for use in PCR. A nucleic acid can be amplified from cDNA or genomic DNA using these oligonucleotide primers and standard PCR amplification techniques. The nucleic acid so amplified can be cloned into an appropriate vector and characterized by DNA sequence analysis. It will be appreciated that cDNA may be prepared from mRNA, by isolating total cellular mRNA by a variety of techniques, for example, by using the guanidinium-thiocyanate extraction procedure of Chirgwin et al., Biochemistry, 18, 5294-5299 (1979). cDNA is then synthesized from the mRNA using reverse transcriptase (for example, Moloney MLV reverse transcriptase available from Gibco/BRL, Bethesda, Md., or AMV reverse transcriptase available from Seikagaku America, Inc., St. Petersburg, Fla.).

An isolated nucleic acid molecule of the invention which is RNA can be isolated by cloning a cDNA encoding a novel protein of the invention into an appropriate vector which allows for transcription of the cDNA to produce an RNA molecule which encodes the MeCP2E1 protein. For example, a cDNA can be cloned downstream of a bacteriophage promoter, (e.g. a T7 promoter) in a vector, cDNA can be transcribed in vitro with T7 polymerase, and the resultant RNA can be isolated by standard techniques.

A nucleic acid molecule of the invention may also be chemically synthesized using standard techniques. Various methods of chemically synthesizing polydeoxynucleotides are known, including solid-phase synthesis which, like peptide synthesis, has been fully automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373,071).

The initiation codon and untranslated sequences of the nucleic acid molecules of the invention may be determined using currently available computer software designed for the purpose, such as PC/Gene (IntelliGenetics Inc., Calif.). Regulatory elements can be identified using conventional techniques. The function of the elements can be confirmed by using these elements to express a reporter gene which is operatively linked to the elements. These constructs may be introduced into cultured cells using standard procedures. In addition to identifying regulatory elements in DNA, such constructs may also be used to identify proteins interacting with the elements, using techniques known in the art.

The sequence of a nucleic acid molecule of the invention may be inverted relative to its normal presentation for transcription to produce an antisense nucleic acid molecule. Preferably, an antisense sequence is constructed by inverting a region preceding the initiation codon or an unconserved region. In particular, the nucleic acid sequences contained in the nucleic acid molecules of the invention or a fragment thereof, preferably a nucleic acid sequence shown in SEQ ID No. 3 may be inverted relative to its normal presentation for transcription to produce antisense nucleic acid molecules.

The antisense nucleic acid molecules of the invention or a fragment thereof, may be chemically synthesized using naturally occurring nucleotides or variously modified nucleotides designed to increase the biological stability of the molecules or to increase the physical stability of the duplex formed with mRNA or the native gene e.g. phosphorothioate derivatives and acridine substituted nucleotides. The antisense sequences may be produced biologically using an expression vector introduced into cells in the form of a recombinant plasmid, phagemid or attenuated virus in which antisense sequences are produced under the control of a high efficiency regulatory region, the activity of which may be determined by the cell type into which the vector is introduced.

The invention also provides nucleic acids encoding fusion proteins comprising a novel protein of the invention and a selected protein, or a selectable marker protein (see below).

II. Novel Proteins of the Invention

The invention further includes an isolated MeCP2E1 protein encoded by the nucleic acid molecules of the invention. Within the context of the present invention, a protein of the invention may include various structural forms of the primary protein which retain biological activity.

Broadly stated, the present invention provides an isolated protein encoded by exon 1, 3 and 4 of the MECP2 gene.

In a preferred embodiment of the invention, the MeCP2E1 protein has the amino acid sequence as shown in SEQ ID No. 4 or a fragment or variant thereof.

The invention also includes mutated forms of the MeCP2E 1 protein that are associated with a neuropsychiatric disorder or developmental disorder. Specifically, the invention includes the mutations in MECP2E1 described in Table 1.

In addition to full length amino acid sequences, the proteins of the present invention also include truncations of the protein, and analogs, and homologs of the protein and truncations thereof as described herein. Truncated proteins may comprise peptides of at least fifteen amino acid residues.

Analogs or variants of the protein having the amino acid sequence shown in SEQ ID No. 4 and/or truncations thereof as described herein, may include, but are not limited to an amino acid sequence containing one or more amino acid substitutions, insertions, and/or deletions Amino acid substitutions may be of a conserved or non-conserved nature. Conserved amino acid substitutions involve replacing one or more amino acids of the proteins of the invention with amino acids of similar charge, size, and/or hydrophobicity characteristics. When only conserved substitutions are made the resulting analog should be functionally equivalent. Non-conserved substitutions involve replacing one or more amino acids of the amino acid sequence with one or more amino acids which possess dissimilar charge, size, and/or hydrophobicity characteristics.

One or more amino acid insertions may be introduced into the amino acid sequence shown in SEQ ID No. 4. Amino acid insertions may consist of single amino acid residues or sequential amino acids ranging from 2 to 15 amino acids in length. For example, amino acid insertions may be used to destroy target sequences so that the protein is no longer active. This procedure may be used in vivo to inhibit the activity of a protein of the invention.

Deletions may consist of the removal of one or more amino acids, or discrete portions from the amino acid sequence shown in SEQ ID No. 4. The deleted amino acids may or may not be contiguous. The lower limit length of the resulting analog with a deletion mutation is about 10 amino acids, preferably 100 amino acids.

Analogs of a protein of the invention may be prepared by introducing mutations in the nucleotide sequence encoding the protein. Mutations in nucleotide sequences constructed for expression of analogs of a protein of the invention must preserve the reading frame of the coding sequences. Furthermore, the mutations will preferably not create complementary regions that could hybridize to produce secondary mRNA structures, such as loops or hairpins, which could adversely affect translation of the receptor mRNA.

Mutations may be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site specific mutagenesis procedures may be employed to provide an altered gene having particular codons altered according to the substitution, deletion, or insertion required. Deletion or truncation of a protein of the invention may also be constructed by utilizing convenient restriction endonuclease sites adjacent to the desired deletion. Subsequent to restriction, overhangs may be filled in, and the DNA religated. Exemplary methods of making the alterations set forth above are disclosed by Sambrook et al (Molecular Cloning: A Laboratory Manual, 2nd Ed., Cold Spring Harbor Laboratory Press, 1989).

The proteins of the invention also include homologs of the amino acid sequence having the exon 1 region shown in SEQ ID No. 4 and/or truncations thereof as described herein.

A homologous protein includes a protein with an amino acid sequence having at least 70%, preferably 80-90% identity with the amino acid sequence as shown in SEQ ID No. 4 and includes the exon 1 region characteristic of the MeCP2E1 protein. As with the nucleic acid molecules of the invention, identity is calculated according to methods known in the art. Sequence identity is most preferably assessed by the algorithm of BLAST version 2.1 advanced search. BLAST is a series of programs that are available online at www.ncbi.nlm nih.gov/BLAST. The advanced BLAST search (www.ncbi.nlm nih gov/blast/blast.cgi?J-form=1) is set to default parameters (i.e. Matrix BLOSUM62, Gap existence cost 11; Per residue gap cost 1; Lambda ration 0.85 default).

The invention also contemplates isoforms of the proteins of the invention. An isoform contains the same number and kinds of amino acids as a protein of the invention, but the isoform has a different molecular structure. The isoforms contemplated by the present invention are those having the same properties as a protein of the invention as described herein.

The present invention also includes a protein of the invention conjugated with a selected protein, or a selectable marker protein (see below) to produce fusion proteins. Additionally, immunogenic portions of a protein of the invention are within the scope of the invention.

The proteins of the invention (including truncations, analogs, etc.) may be prepared using recombinant DNA methods. Accordingly, the nucleic acid molecules of the present invention having a sequence which encodes a protein of the invention may be incorporated in a known manner into an appropriate expression vector which ensures good expression of the protein. Possible expression vectors include but are not limited to cosmids, plasmids, or modified viruses (e.g. replication defective retroviruses, adenoviruses and adeno-associated viruses), so long as the vector is compatible with the host cell used. The expression vectors are "suitable for transformation of a host cell", means that the expression vectors contain a nucleic acid molecule of the invention and regulatory sequences selected on the basis of the host cells to be used for expression, which is operatively linked to the nucleic acid molecule. Operatively linked is intended to mean that the nucleic acid is linked to regulatory sequences in a manner which allows expression of the nucleic acid.

The invention therefore contemplates a recombinant expression vector of the invention containing a nucleic acid molecule of the invention, or a fragment thereof, and the necessary regulatory sequences for the transcription and translation of the inserted protein-sequence. Suitable regulatory sequences may be derived from a variety of sources, including bacterial, fungal, or viral genes (For example, see the regulatory sequences described in Goeddel, Gene Expression Technology: Methods in Enzymology 185, Academic Press, San Diego, Calif. (1990). Selection of appropriate regulatory sequences is dependent on the host cell chosen, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector. It will also be appreciated that the necessary regulatory sequences may be supplied by the native protein and/or its flanking regions.

The invention further provides a recombinant expression vector comprising a DNA nucleic acid molecule of the invention cloned into the expression vector in an antisense orientation. That is, the DNA molecule is operatively linked to a regulatory sequence in a manner which allows for expression, by transcription of the DNA molecule, of an RNA molecule which is antisense to a nucleotide sequence comprising the nucleotides as shown SEQ ID No. 3. Regulatory sequences operatively linked to the antisense nucleic acid can be chosen which direct the continuous expression of the antisense RNA molecule.

The recombinant expression vectors of the invention may also contain a selectable marker gene which facilitates the selection of host cells transformed or transfected with a recombinant molecule of the invention. Examples of selectable marker genes are genes encoding a protein such as G418 and hygromycin which confer resistance to certain drugs, β-galactosidase, chloramphenicol acetyltransferase, or firefly luciferase. Transcription of the selectable marker gene is monitored by changes in the concentration of the selectable marker protein such as β-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of recombinant expression vectors of the invention and in particular to determine the effect of a mutation on expression and phenotype. It will be appreciated that selectable markers can be introduced on a separate vector from the nucleic acid of interest.

The recombinant expression vectors may also contain genes which encode a fusion moiety which provides increased expression of the recombinant protein; increased solubility of the recombinant protein; and aid in the purification of a target recombinant protein by acting as a ligand in affinity purification. For example, a proteolytic cleavage site may be added to the target recombinant protein to allow separation of the recombinant protein from the fusion moiety subsequent to purification of the fusion protein.

Recombinant expression vectors can be introduced into host cells to produce a transformed host cell. The term "transformant host cell" is intended to include prokaryotic and eukaryotic cells which have been transformed or transfected with a recombinant expression vector of the invention. The terms "transformed with", "transfected with", "transformation" and "transfection" are intended to encompass introduction of nucleic acid (e.g. a vector) into a cell by one of many possible techniques known in the art. Prokaryotic cells can be transformed with nucleic acid by, for example, electroporation or calcium-chloride mediated transformation. Nucleic acid can be introduced into mammalian cells via conventional techniques such as calcium phosphate or calcium chloride co-precipitation, DEAE-dextran-mediated transfection, lipofectin, electroporation or microinjection. Suitable methods for transforming and transfecting host cells can be found in Sambrook et al. (Molecular Cloning: A Laboratory Manual, 2nd Edition, Cold Spring Harbor Laboratory press (1989)), and other laboratory textbooks.

Suitable host cells include a wide variety of prokaryotic and eukaryotic host cells. For example, the proteins of the invention may be expressed in bacterial cells such as E. coli, insect cells (using baculovirus), yeast cells or mammalian cells. Other suitable host cells can be found in Goeddel, Gene Expression Technology: Methods in Enzymology 185, Academic Press, San Diego, Calif. (1991).

The proteins of the invention may also be prepared by chemical synthesis using techniques well known in the chemistry of proteins such as solid phase synthesis (Merrifield, 1964, J. Am. Chem. Assoc. 85:2149-2154) or synthesis in homogenous solution (Houbenweyl, 1987, Methods of Organic Chemistry, ed. E. Wansch, Vol. 15 I and II, Thieme, Stuttgart).

III. Applications

A. Diagnostic Applications

As previously mentioned, the present inventors have isolated a novel splice variant of the MECP2 gene, MECP2E1, and have shown that exon 1 is deleted or mutated in people with neuropsychiatric disorders or developmental disorders such as Rett's syndrome or mental retardation. As a result, the present invention also includes a method of detecting a neuropsychiatric or developmental disorder by detecting a mutation or deletion in the MECP2E1 nucleic acid or MeCP2E1 protein.

The term "neuropsychiatric disorder" as used herein includes, but is not limited to, autism/autism spectrum disorder, epilepsy, Angelman syndrome, Prader-Willi syndrome, encephalopathy, schizophrenia, bipolar affective disorder, depression, obsessive compulsive disorder, panic disorder, attention deficit hyperactivity disorder, and ataxia.

The term "developmental disorder" includes but is not limited to, mental retardation.

i) Detecting Mutations in the Nucleic Acid Sequence

In one embodiment, the present invention provides a method for detecting a neuropsychiatric or developmental disorder comprising detecting a deletion or mutation in exon 1 of the MECP2 gene in a sample obtained from an animal, preferably a mammal, more preferably a human The Examples and Table 1 summarize some of the mutations found in MECP2E1 in patient's with Rett's syndrome or developmental delay. (They are also described in Section I). Screening assays can be developed for each of the mutations. Examples of methods that can be used to detect mutations include sequencing, polymerase chain reaction, reverse transcription-polymerase chain reaction, denaturing HPLC, electrophoretic mobility, nucleic acid hybridization, fluorescent in situ hybridization and multiplex ligation-dependent probe amplification. Details of screening assays that may be employed are provided in Examples 3, 4 or 5.

Rett's syndrome has been shown to be caused by deletions in exon 1 of MECP2. Patients homozygous for these deletions can be detected by PCR-amplifying and sequencing exon 1 and flanking sequences using X1F/X1R primers.

Consequently, the present invention includes a method for determining a deletion in exon 1 of the MECP2 gene by a method comprising:

(a) amplifying the nucleic acid sequences in the sample with primers X1F (5'-CCATCACAGCCAATGACG-3') (SEQ ID No. 19) and X1R (5'-AGGGGGAGGGTAGA-GAGGAG-3') (SEQ ID No. 20) in a polymerase chain reaction;

(b) amplifying the nucleic acid sequences from a control with same primers;

(c) sequencing the amplified sequences; and (d) comparing the sample sequences to the control sequences wherein deletion of nucleotides in the sample sequence compared to the control sequence indicates that the sample is from an animal with Rett's syndrome.

Additional exon 1 mutations not detectable by the PCR reaction, can be identified using multiplex ligation-dependent probe amplification (MLPA) in all four exons. MLPA analysis is described in reference 5 and in Schouten, U.S. application Ser. No. 10/218,567, (publication number 2003/0108913) which are incorporated herein in by reference. Accordingly, the present invention includes a method for determining a deletion in exon 1 of the MECP2 gene by performing MLPA analysis with 20 probe pairs that target the four MECP2 exons, six X-linked control regions and ten autosomal control regions.

One skilled in the art will appreciate that other methods, in addition to the ones discussed above and in the examples, can be used to detect mutations in exon 1 of the MECP2 gene. For example, in order to isolate nucleic acids from a sample, one can prepare nucleotide probes from the nucleic acid sequences of the invention. In addition, the nucleic acid probes described herein (for example, see FIG. 1) can also be used. A nucleotide probe may be labelled with a detectable marker such as a radioactive label which provides for an adequate signal and has sufficient half life such as $^{32}P$, $^{3}H$, $^{14}C$ or the like. Other detectable markers which may be used include antigens that are recognized by a specific labelled antibody, fluorescent compounds, enzymes, antibodies specific for a labelled antigen, and chemiluminescent compounds. An appropriate label may be selected having regard to the rate of hybridization and binding of the probe to the nucleotide to be detected and the amount of nucleotide available for hybridization.

Accordingly, the present invention also relates to a method of detecting the presence of a nucleic acid molecule containing exon 1 of the MECP2 gene in a sample comprising contacting the sample under hybridization conditions with one or more of nucleotide probes which hybridize to the nucleic acid molecules and are labelled with a detectable marker, and determining the degree of hybridization between the nucleic acid molecule in the sample and the nucleotide probes.

Hybridization conditions which may be used in the methods of the invention are known in the art and are described for example in Sambrook J, Fritch E F, Maniatis T. In: Molecular Cloning, A Laboratory Manual, 1989. (Nolan C, Ed.), Cold Spring Harbor Laboratory Press, Cold Spring Harbor, N.Y. The hybridization product may be assayed using techniques known in the art. The nucleotide probe may be labelled with a detectable marker as described herein and the hybridization product may be assayed by detecting the detectable marker or the detectable change produced by the detectable marker.

Prior to hybridizing a sample with DNA probes, the sample can be treated with primers that flank the MECP2 gene in order to amplify the nucleic acid sequences in the sample. The primers used may be the ones described in the present application. For example, primers specific for human MECP2 include HF(ctcggagagagggctgtg) (SEQ ID No. 5), HR1(cttgagggtttgtccttga) (SEQ ID No. 6), HR2(cgtttgat-caccatgacctg) (SEQ ID No. 7). Primers for mouse MECP2 include MF(aggaggcgaggaggagagac) (SEQ ID NO. 8) and MR (ctggctctgcagaatggtg) (SEQ ID No. 9). In addition, the sequence of the MECP2 gene provided herein also permits the identification and isolation, or synthesis of new nucleotide sequences which may be used as primers to amplify a nucleic acid molecule of the invention. The primers may be used to amplify the genomic DNA of other species. The PCR amplified sequences can be examined to determine the relationship between the genes of various species.

The length and bases of the primers for use in the PCR are selected so that they will hybridize to different strands of the desired sequence and at relative positions along the sequence such that an extension product synthesized from one primer when it is separated from its template can serve as a template for extension of the other primer into a nucleic acid of defined length. Primers which may be used in the invention are oligonucleotides i.e. molecules containing two or more deoxyribonucleotides of the nucleic acid molecule of the invention which occur naturally as in a purified restriction endonuclease digest or are produced synthetically using techniques known in the art such as for example phosphotriester and phosphodiester methods (See Good et al Nucl. Acid Res 4:2157, 1977) or automated techniques (See for example, Conolly, B.A. Nucleic Acids Res. 15(7): 3131, 1987). The primers are capable of acting as a point of initiation of synthesis when placed under conditions which permit the synthesis of a primer extension product which is complementary to the DNA sequence of the invention i.e. in the presence of nucleotide substrates, an agent for polymerization such as DNA polymerase and at suitable temperature and pH. Preferably, the primers are sequences that do not form secondary structures by base pairing with other copies of the primer or sequences that form a hair pin configuration. The primer preferably contains between about 7 and 25 nucleotides.

The primers may be labelled with detectable markers which allow for detection of the amplified products. Suitable detectable markers are radioactive markers such as P-32, S-35, I-125, and H-3, luminescent markers such as chemiluminescent markers, preferably luminol, and fluorescent markers, preferably dansyl chloride, fluorescein-5-isothiocyanate, and 4-fluor-7-nitrobenz-2-axa-1,3 diazole, enzyme markers such as horseradish peroxidase, alkaline phosphatase, β-galactosidase, acetylcholinesterase, or biotin.

It will be appreciated that the primers may contain non-complementary sequences provided that a sufficient amount of the primer contains a sequence which is complementary to a nucleic acid molecule of the invention or oligonucleotide fragment thereof, which is to be amplified. Restriction site linkers may also be incorporated into the primers allowing for digestion of the amplified products with the appropriate restriction enzymes facilitating cloning and sequencing of the amplified product.

In an embodiment of the invention a method of determining the presence of a nucleic acid molecule of the invention is provided comprising treating the sample with primers which are capable of amplifying the nucleic acid molecule or a predetermined oligonucleotide fragment thereof in a polymerase chain reaction to form amplified sequences, under conditions which permit the formation of amplified sequences and, assaying for amplified sequences.

The polymerase chain reaction refers to a process for amplifying a target nucleic acid sequence as generally described in Innis et al, Academic Press, 1990 in Mullis et al., U.S. Pat. No. 4,863,195 and Mullis, U.S. Pat. No. 4,683,202 which are incorporated herein by reference. Conditions for amplifying a nucleic acid template are described in M. A. Innis and D.H. Gelfand, PCR Protocols, A Guide to Methods and Applications M.A. Innis, D.H. Gelfand, J.J. Sninsky and T.J. White eds, pp 3-12, Academic Press 1989, which is also incorporated herein by reference.

The amplified products can be isolated and distinguished based on their respective sizes using techniques known in the art. For example, after amplification, the DNA sample can be separated on an agarose gel and visualized, after staining with ethidium bromide, under ultra violet (UV) light. DNA may be amplified to a desired level and a further extension reaction may be performed to incorporate nucleotide derivatives having detectable markers such as radioactive labelled or biotin labelled nucleoside triphosphates. The primers may also be labelled with detectable markers as discussed above. The detectable markers may be analyzed by restriction and electrophoretic separation or other techniques known in the art.

The conditions which may be employed in the methods of the invention using PCR are those which permit hybridization and amplification reactions to proceed in the presence of DNA in a sample and appropriate complementary hybridization primers. Conditions suitable for the polymerase chain reaction are generally known in the art. For example, see M.A. Innis and D.H. Gelfand, PCR Protocols, A guide to Methods and Applications M.A. Innis, D.H. Gelfand, J.J. Sninsky and T.J. White eds, pp 3-12, Academic Press 1989, which is incorporated herein by reference. Preferably, the PCR utilizes polymerase obtained from the thermophilic bacterium *Thermus aquatics* (Taq polymerase, GeneAmp Kit, Perkin Elmer Cetus) or other thermostable polymerase may be used to amplify DNA template strands.

It will be appreciated that other techniques such as the Ligase Chain Reaction (LCR) and NASBA may be used to amplify a nucleic acid molecule of the invention (Barney in "PCR Methods and Applications", August 1991, Vol. 1(1), page 5, and European Published Application No. 0320308, published Jun. 14, 1989, and U.S. Pat. No. 5,130,238 to Malek).

(ii) Detecting the MeCP2E1 Protein

In another embodiment, the present invention provides a method for detecting a neuropsychiatric or developmental disorder comprising detecting a deletion or mutation in the MeCP2E1 protein in a sample from an animal.

The MeCP2E1 protein of the present invention may be detected in a biological sample using antibodies that are specific for MeCP2E1 using various immunoassays that are discussed below.

Conventional methods can be used to prepare the antibodies. For example, by using a peptide from the MeCP2E1 protein of the invention, polyclonal antisera or monoclonal antibodies can be made using standard methods. A mammal, (e.g., a mouse, hamster, or rabbit) can be immunized with an immunogenic form of the peptide which elicits an antibody response in the mammal. Techniques for conferring immunogenicity on a peptide include conjugation to carriers or other techniques well known in the art. For example, the peptide can be administered in the presence of adjuvant. The progress of immunization can be monitored by detection of antibody titers in plasma or serum. Standard ELISA or other immunoassay procedures can be used with the immunogen as antigen to assess the levels of antibodies. Following immunization, antisera can be obtained and, if desired, polyclonal antibodies isolated from the sera.

To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art, (e.g., the hybridoma technique originally developed by Kohler and Milstein (Nature 256, 495-497 (1975)) as well as other techniques such as the human B-cell hybridoma technique (Kozbor et al., Immunol. Today 4, 72 (1983)), the EBV-hybridoma technique to produce human monoclonal antibodies (Cole et al. Monoclonal Antibodies in Cancer Therapy (1985) Allen R. Bliss, Inc., pages 77-96), and screening of combinatorial antibody libraries (Huse et al., Science 246, 1275 (1989)). Hybridoma cells can be screened immunochemically for production of antibodies specifically reactive with the peptide and the monoclonal antibodies can be isolated. Therefore, the invention also contemplates hybridoma cells secreting monoclonal antibodies with specificity for a protein of the invention.

The term "antibody" as used herein is intended to include fragments thereof which also specifically react with a protein of the invention, or peptide thereof. Antibodies can be fragmented using conventional techniques and the fragments screened for utility in the same manner as described above. For example, F(ab')$_2$ fragments can be generated by treating antibody with pepsin. The resulting F(ab')$_2$ fragment can be treated to reduce disulfide bridges to produce Fab' fragments.

Chimeric antibody derivatives, i.e., antibody molecules that combine a non-human animal variable region and a human constant region are also contemplated within the scope of the invention. Chimeric antibody molecules can include, for example, the antigen binding domain from an antibody of a mouse, rat, or other species, with human constant regions. Conventional methods may be used to make chimeric antibodies containing the immunoglobulin variable region which recognizes a CipA protein (See, for example, Morrison et al., Proc. Natl. Acad. Sci. U.S.A. 81,6851 (1985); Takeda et al., Nature 314, 452 (1985), Cabilly et al., U.S. Pat. No. 4,816,567; Boss et al., U.S. Pat. No. 4,816,397; Tanaguchi et al., European Patent Publication EP171496; European Patent Publication 0173494, United Kingdom patent GB 2177096B).

Monoclonal or chimeric antibodies specifically reactive with a protein of the invention as described herein can be further humanized by producing human constant region chimeras, in which parts of the variable regions, particularly the conserved framework regions of the antigen-binding domain, are of human origin and only the hypervariable regions are of non-human origin. Such immunoglobulin molecules may be made by techniques known in the art, (e.g., Teng et al., Proc. Natl. Acad. Sci. U.S.A., 80, 7308-7312 (1983); Kozbor et al., Immunology Today, 4, 7279 (1983); Olsson et al., Meth. Enzymol., 92, 3-16 (1982)), and PCT Publication WO92/06193 or EP 0239400). Humanized antibodies can also be commercially produced (Scotgen Limited, 2 Holly Road, Twickenham, Middlesex, Great Britain.)

Specific antibodies, or antibody fragments, reactive against a protein of the invention may also be generated by screening expression libraries encoding immunoglobulin genes, or portions thereof, expressed in bacteria with peptides produced from the nucleic acid molecules of the present invention. For example, complete Fab fragments, VH regions and FV regions can be expressed in bacteria using phage expression libraries (See for example Ward et al., Nature 341, 544-546: (1989); Huse et al., Science 246, 1275-1281 (1989); and McCafferty et al. Nature 348, 552-554 (1990)).

Antibodies may also be prepared using DNA immunization. For example, an expression vector containing a nucleic acid of the invention (as described above) may be injected into a suitable animal such as mouse. The protein of the invention will therefore be expressed in vivo and antibodies will be induced. The antibodies can be isolated and prepared as described above for protein immunization.

The antibodies may be labelled with a detectable marker including various enzymes, fluorescent materials, luminescent materials and radioactive materials. Examples of suitable enzymes include horseradish peroxidase, biotin, alkaline phosphatase, β-galactosidase, or acetylcholinesterase; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include S-35, Cu-64, Ga-67, Zr-89, Ru-97, Tc-99m, Rh-105, Pd-109, In-111, I-123, I-125, I131, Re-186, Au-198, Au-199, Pb-203, At –211, Pb-212 and Bi-212. The antibodies may also be labelled or conjugated to one partner of a ligand binding pair. Representative examples include avidin-biotin and riboflavin-riboflavin binding protein. Methods for conjugating or labelling the antibodies discussed above with the representative labels set forth above may be readily accomplished using conventional techniques.

The antibodies reactive against proteins of the invention (e.g. enzyme conjugates or labelled derivatives) may be used to detect a protein of the invention in various samples, for example they may be used in any known immunoassays which rely on the binding interaction between an antigenic determinant of a protein of the invention and the antibodies. Examples of such assays are radioimmunoassays, enzyme immunoassays (e.g. ELISA), immunofluorescence, immuno-precipitation, latex agglutination, hemagglutination, and histochemical tests. Thus, the antibodies may be used to identify or quantify the amount of a protein of the invention in a sample in order to diagnose the presence of Rett's syndrome.

In a method of the invention a predetermined amount of a sample or concentrated sample is mixed with antibody or labelled antibody. The amount of antibody used in the process is dependent upon the labelling agent chosen. The resulting protein bound to antibody or labelled antibody may be isolated by conventional isolation techniques, for example, salting out, chromatography, electrophoresis, gel filtration, fractionation, absorption, polyacrylamide gel electrophoresis, agglutination, or combinations thereof.

The sample or antibody may be insolubilized, for example, the sample or antibody can be reacted using known methods with a suitable carrier. Examples of suitable carriers are Sepharose or agarose beads. When an insolubilized sample or antibody is used protein bound to antibody or unreacted antibody is isolated by washing. For example, when the sample is blotted onto a nitrocellulose membrane, the antibody bound to a protein of the invention is separated from the unreacted antibody by washing with a buffer, for example, phosphate buffered saline (PBS) with bovine serum albumin (BSA).

When labelled antibody is used, the presence of MeCP2E1 can be determined by measuring the amount of labelled antibody bound to a protein of the invention in the sample or of the unreacted labelled antibody. The appropriate method of measuring the labelled material is dependent upon the labelling agent.

When unlabelled antibody is used in the method of the invention, the presence of MeCP2E1 can be determined by measuring the amount of antibody bound to the protein using substances that interact specifically with the antibody to cause agglutination or precipitation. In particular, labelled antibody against an antibody specific for a protein of the invention, can be added to the reaction mixture. The presence of a protein of the invention can be determined by a suitable method from among the already described techniques depending on the type of labelling agent. The antibody against an antibody specific for a protein of the invention can be prepared and labelled by conventional procedures known in the art which have been described herein. The antibody against an antibody specific for a protein of the invention may be a species specific anti-immunoglobulin antibody or monoclonal antibody, for example, goat anti-rabbit antibody may be used to detect rabbit antibody specific for a protein of the invention.

(iii) Kits

The reagents suitable for carrying out the methods of the invention may be packaged into convenient kits providing the necessary materials, packaged into suitable containers. Such kits may include all the reagents required to detect a nucleic acid molecule or protein of the invention in a sample by means of the methods described herein, and optionally suitable supports useful in performing the methods of the invention.

In one embodiment of the invention, the kit includes primers which are capable of amplifying a nucleic acid molecule of the invention or a predetermined oligonucleotide fragment thereof, all the reagents required to produce the amplified nucleic acid molecule or predetermined fragment thereof in the polymerase chain reaction, and means for assaying the amplified sequences. The kit may also include restriction enzymes to digest the PCR products. In another embodiment of the invention the kit contains a nucleotide probe which hybridizes with a nucleic acid molecule of the invention, reagents required for hybridization of the nucleotide probe with the nucleic acid molecule, and directions for its use. In a further embodiment of the invention the kit includes antibodies of the invention and reagents required for binding of the antibody to a protein of the invention in a sample.

The kits may include nucleic acid molecules, proteins or antibodies of the invention (described above) to detect or treat neuropsychiatric disorders and developmental disorders together with instructions for the use thereof.

The methods and kits of the present invention may be used to detect neuropsychiatric and developmental disorders such as Rett's syndrome and mental retardation. Samples which may be tested include bodily materials such as blood, urine, serum, tears, saliva, feces, tissues, organs, cells and the like. In addition to human samples, samples may be taken from mammals such as non-human primates, etc.

Before testing a sample in accordance with the methods described herein, the sample may be concentrated using techniques known in the art, such as centrifugation and filtration. For the hybridization and/or PCR-based methods described herein, nucleic acids may be extracted from cell extracts of the test sample using techniques known in the art.

B. Therapeutic Applications

As mentioned previously, the nucleic acid molecules of the present invention are deleted or mutated in people with neuropsychiatric disorders and developmental disorders.

Accordingly, the present invention provides a method of treating or preventing neuropsychiatric disorders and developmental disorders by administering a nucleic acid sequence containing a sufficient portion of the MECP2E1 splice variant to treat or prevent neuropsychiatric disorders and developmental disorders. The present invention includes a use of a nucleic acid molecule or protein of the invention to treat or detect neuropsychiatric disorders and developmental disorders.

Recombinant molecules comprising a nucleic acid sequence or fragment thereof, may be directly introduced into cells or tissues in vivo using delivery vehicles such as retroviral vectors, adenoviral vectors and DNA virus vectors. They may also be introduced into cells in vivo using physical techniques such as microinjection and electroporation or chemical methods such as coprecipitation and incorporation of DNA into liposomes. Recombinant molecules may also be delivered in the form of an aerosol or by lavage.

The nucleic acid sequences may be formulated into pharmaceutical compositions for administration to subjects in a biologically compatible form suitable for administration in vivo. By "biologically compatible form suitable for administration in vivo" is meant a form of the substance to be administered in which any toxic effects are outweighed by the therapeutic effects. The substances may be administered to living organisms including humans, and animals. Administration of a therapeutically active amount of the pharmaceutical compositions of the present invention is defined as an amount effective, at dosages and for periods of time necessary to achieve the desired result. For example, a therapeutically active amount of a substance may vary according to factors such as the disease state, age, sex, and weight of the individual, and the ability of antibody to elicit a desired response in the individual. Dosage regima may be adjusted to provide the optimum therapeutic response. For example, several divided doses may be administered daily or the dose may be proportionally reduced as indicated by the exigencies of the therapeutic situation.

The active substance may be administered in a convenient manner such as by injection (subcutaneous, intravenous, etc.), oral administration, inhalation, transdermal application, or rectal administration. Depending on the route of administration, the active substance may be coated in a material to protect the compound from the action of enzymes, acids and other natural conditions which may inactivate the compound.

The compositions described herein can be prepared by per se known methods for the preparation of pharmaceutically acceptable compositions which can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985). On this basis, the compositions include, albeit not exclusively, solutions of the substances in association with one or more pharmaceutically acceptable vehicles or diluents, and contained in buffered solutions with a suitable pH and iso-osmotic with the physiological fluids.

C. Experimental Models

The present invention also includes methods and experimental models for studying the function of the MECP2 gene and MeCP2E 1 protein. Cells, tissues and non-human animals that lack the MECP2E1 splice variant or partially lack in MeCP2E1 expression may be developed using recombinant expression vectors having a specific deletion or mutation in the MECP2E1 gene. A recombinant expression vector may be used to inactivate or alter the MECP2 gene by homologous recombination and thereby create a MECP2E1 deficient cell, tissue or animal. In particular, a targeted mutation could be designed to result in deficient MECP2E1 while MECP2E2 remains unaltered. This can be accomplished by targeting exon 1 of the MECP2 gene.

Null alleles may be generated in cells, such as embryonic stem cells by deletion mutation. A recombinant MECP2 gene may also be engineered to contain an insertion mutation which inactivates MECP2E1. Such a construct may then be introduced into a cell, such as an embryonic stem cell, by a technique such as transfection, electroporation, injection etc. Cells lacking an intact MECP2 gene may then be identified, for example by Southern blotting, Northern Blotting or by assaying for MECP2E1 using the methods described herein. Such cells may then be fused to embryonic stem cells to generate transgenic non-human animals deficient in MECP2E1. Germline transmission of the mutation may be achieved, for example, by aggregating the embryonic stem cells with early stage embryos, such as 8 cell embryos, in vitro; transferring the resulting blastocysts into recipient females and; generating germline transmission of the resulting aggregation chimeras. Such a mutant animal may be used to define specific cell populations, developmental patterns and in vivo processes, normally dependent on MECP2E1 expression. The present invention also includes the preparation of tissue specific knock-outs of the MECP2E 1 variant.

The following non-limiting examples are illustrative of the present invention:

EXAMPLES

Example 1

Identification of MEC2E1 Splice Variant

Inspection of the 5'UTR revealed that, whereas exon 2 has a number of in-frame stops upstream of the ATG, exon 1 contains an open reading frame across its entire length including an ATG. Submitting a theoretical construct composed of exons 1, 3 and 4 to the ATGpr program (www.hri.co.jp/atgpr/), which predicts the likelihood of an ATG to be an initiation codon based on significance of its surrounding Kozak nucleotide context, returned a reliability score of 97% compared to 64% for MECP2E2. A search in EST databases identified eight examples of our theorized transcript (named MECP2E1) (FIG. 1b) (vs. 14 examples of MECP2E2). MECP2E1 would be predicted to encode a new variant, MeCP2E1, with an alternative longer N-terminus determined by exon 1.

Example 2

Expression of MECP2E1

To confirm that MECP2E1 is in fact expressed and not an artifact of cDNA library preparations, cDNA from a variety of tissues was PCR-amplified using a 5'-primer in exon 1 and a 3"-primer in exon 3 (FIG. 1a). Two PCR products corresponding to MECP2E2 and MECP2E1 by size and sequence were obtained in all tissues, including fetal and adult brain, and in brain subregions (FIG. 1c). Results in mouse were similar (FIG. 1c). The expression levels of the two transcripts in adult human brain were quantified. MECP2E1 expression is 10 times higher than MECP2E2

(FIG. 1d). The subcellular localization of MeCP2E1 following transfection of 3' myc-tagged MECP2E1 into COS-7 cells was found to be principally in the nucleus (FIG. 1e).

MECP2E1 was not detected in previous expression studies. Northern analyses reveal three transcripts, 1.9, 5 and 10.1 kb, with the differences in size due to alternative polyadenylation signal usage (4, 6, 8) (FIG. 1a). MECP2E1 differs from MECP2E2 in lacking the 124-nucleotide exon 2. At the 5 and 10.1 kb positions on the gel, the two transcripts would not be separable. In the 1.9 kb range, published northern blots do show a thick or double band likely corresponding to the two transcripts. Likewise, conventional western blot analysis would not allow resolution of the two MeCP2 isoforms (molecular weight difference <0.9 kD; FIG. 1f).

Example 3

Mutations in MECP2E1 in Rett's Syndrome

Figure 2:
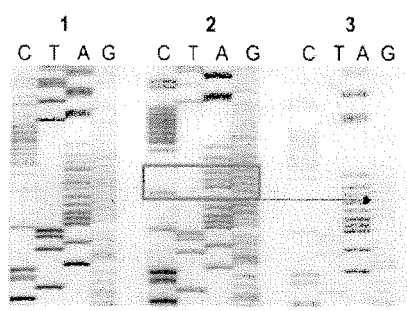
FIG. 2 shows a deletion mutation in patient V1. a1) Sequence of PCR product from genomic DNA using primers X1F/X1R (FIG. 1a). Note mixed sequence. a2) and a3) Sequences of clones of the patient's wild-type and mutant alleles respectively; red box indicating the 11 nucleotides deleted in the mutated allele. b) Electropherograms of the same cloned wild-type and deleted alleles (SEQ ID NOS 43-46, respectively, in order of appearance). c) PCR on indicated cDNAs using primers HF/HR1 (FIG. 1a,c). Lanes 1 and 2 (on 2.5% high resolution agarose) are from control and patient whole blood respectively. Lanes 3 to 8 (on 6% denaturing polyacrylamide) are from control blood (3), patient blood (4), control fetal brain (5), control adult brain (6), control testis (7) and control genomic DNA (8). Note that expression of the patient's MECP2E2 transcript with the 11bp exon 1 deletion (band at 266bp) is not diminished compared to the non-deleted allele (277bp). The 141 and 152bp bands are the deleted and non-deleted MECP2E1 transcripts respectively.
Figure 2:
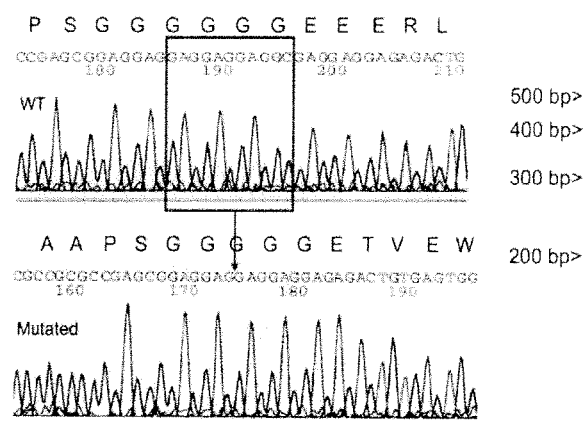
Figure 2:
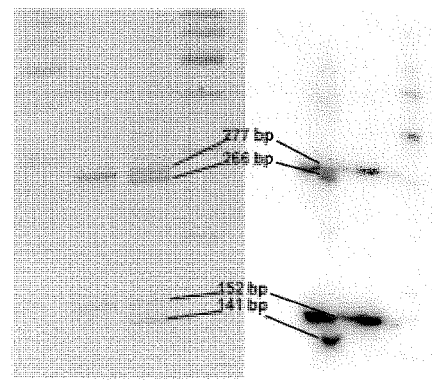

To determine whether the new coding region is mutated in Rett's syndrome, Exon 1 and flanking sequences were PCR-amplified and sequenced in 19 girls with typical RTT in whom no mutations had been found in the other exons. One patient (V1) was found to carry an 1 lbp deletion mutation in exon 1 (FIG. 2). The deletion occurs within the predicted exon 1 open reading frame of MECP2E1 and leads to a frame shift that results in a missense amino acid sequence followed by a premature stop codon after amino acid 36. It does not affect the coding sequence of MECP2E2. This sequence change was not found in 200 control individuals including the patient's parents and brother.

Figure 3:
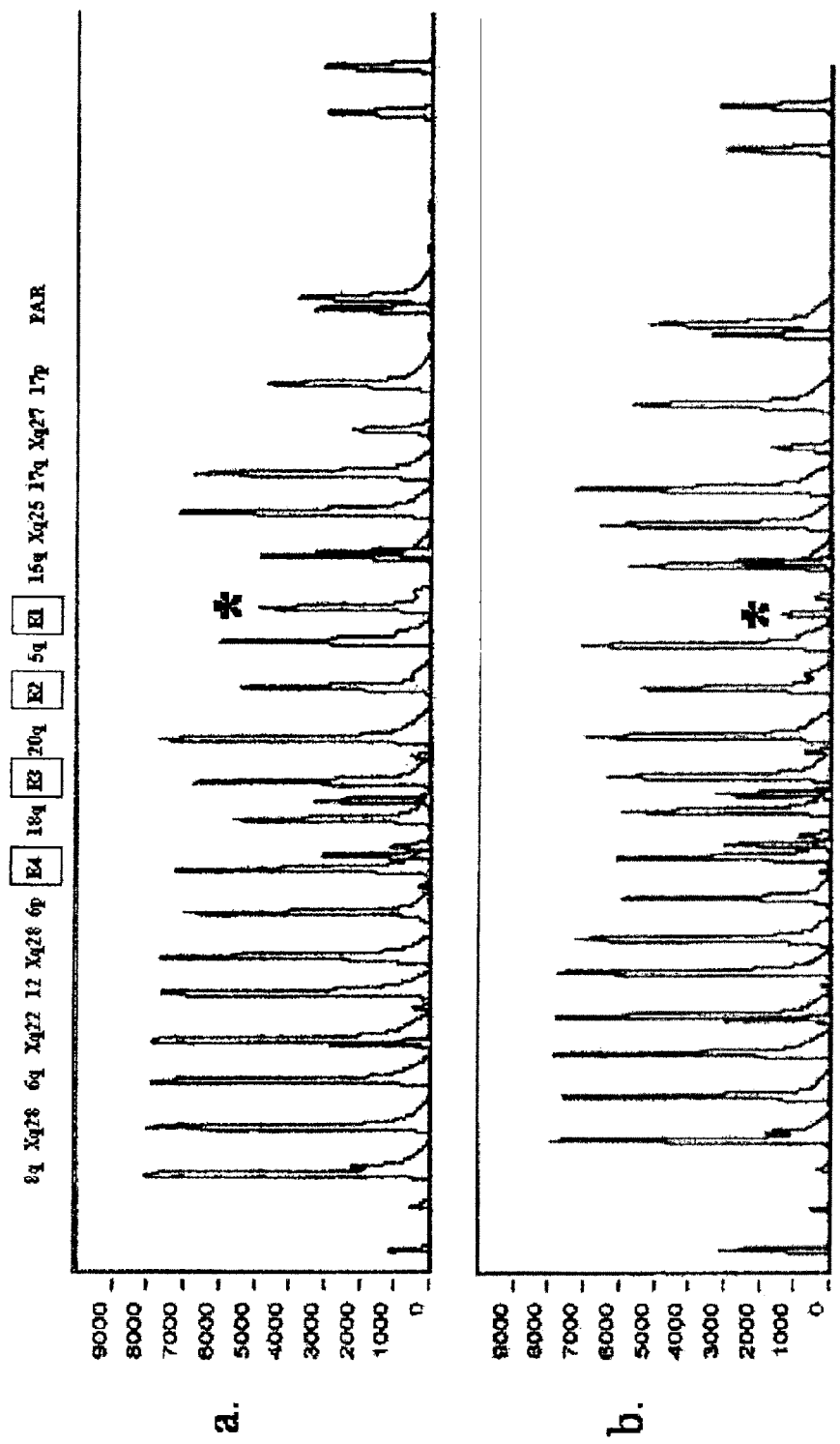
FIG. 3 shows a deletion mutation in patient V2. MECP2 Multiplex ligation-dependent probe amplification (MLPA) peak profiles are shown. Control loci are listed along the top. Boxed regions (E1-E4) indicate MECP2 exons 1-4. a) MLPA profile of normal control. b) MLPA profile of patient V2 shows a hemizygous exon 1 deletion (asterisk). The result was consistently reproducible and sequencing ruled out the possibility of a SNP interfering with the ligation efficiency of the MLPA reaction.

To search, in the remaining patients, for additional exon 1 deletions not detectable by our PCR reaction, multiplex ligation-dependent probe amplification (MLPA) (5) was performed in all four exons and detected a hemizygous deletion of exon 1 in one patient (Patient V2; FIG. 3). Finally, an additional patient with an MLPA-detected deletion restricted to exon 1 was recently documented in abstract form, though the effect on MECP2E1 was not realized (S. Boulanger et al. *Am J Hum Genet.* 73, 572 (2003)).

In contrast, no mutation specific to the MeCP2E2-defining exon 2 has been found to date despite several hundred patients analyzed for mutations in this exon (31 publications; most reviewed in ref. 3). These studies did not include exon 1 as it was considered non-coding.

Exon 1 deletions result in absent or truncated MeCP2E1 proteins. However, they also result in shortening of MECP2E2's 5'UTR and may possibly affect its expression. This possibility was tested in patient V1 by RT-PCR on whole blood. No diminution of MECP2E2 expression was present (FIG. 2c). In conclusion, mutation data indicate that inactivation of MeCP2E1 is sufficient in RTT, but the same cannot be said, to date, of MeCP2E2.

Materials and Methods

PCR, manual sequencing, cloning, rtPCR, gel blotting. PCR amplification was performed using $[NH_4]_2SO_4$-containing PCR buffer (MBI Fermentas) with 1M betaine, 200 µM dNTPs including 50% deaza dGTP, with a 95° C. denaturing step for 3 minutes, followed by cycling at 95° C. for 30 secs, 55° C. for 30 secs, 72° C. for 45 secs for 30 cycles, followed by a 7 minute soak step at 72° C. Manual sequencing was performed, following extraction from a 1% agarose gel, using the Thermosequenase™ kit (USB/Amersham) and run on a 6% denaturing polyacrylamide gel for 3 hours. PCR products were cloned using the pDRIVE vector (Qiagen PCR cloning kit). Whole blood RNA was extracted using the PAXgene Blood RNA Kit (Qiagen). Reverse transcription was performed with random hexamers and a standard Superscript III protocol (Invitrogen). Human brain subregion cDNA was obtained from OriGene. The polyacrylamide gel in (FIG. 2c) was blotted onto Hybond N+(Amersham) and hybridized with primer HF labeled at the 3' end with $[\alpha^{32}I]$-dCTP using deoxynucleotidyl transferase (MBI Fermentas).

Figure 4:
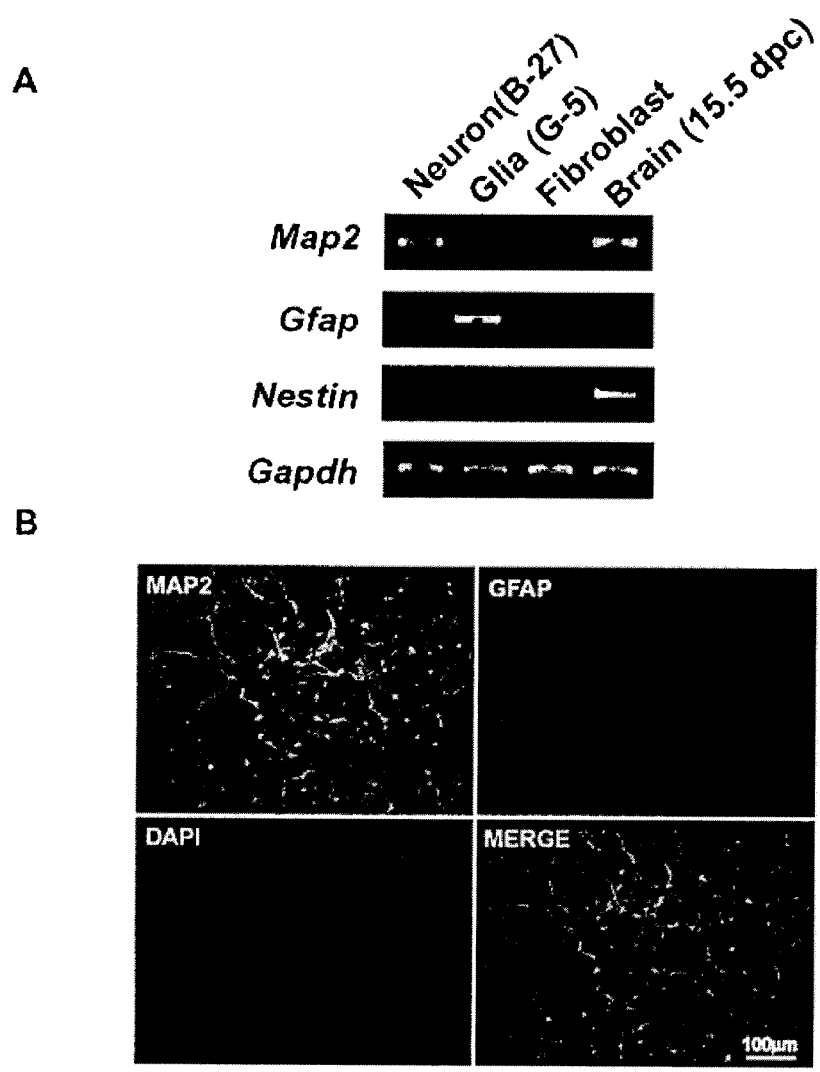
FIG. 4 shows the characterization of the primary brain cell cultures by rtPCRR (A) and IF (B). (A) Map2, Gfap and Nestin expressions indicate that the cultures in B-27 medium were composed primarily of neurons and those in G-5 medium were glial cells. Fibroblasts from the same embryos were also cultured and used as negative controls. Whole brain tissue (15.5 dpc) was used as a positive control for Map2 and Nestin. (B) Double staining for neurons was performed with mouse anti-MAP2 and rabbit anti-GFAP antibodies. They were also counterstained with DAPI (blue). Most of the cells are neurons, which stained positively for MAP2 (green), and an insignificant percentage of contamination with glial cells stained positively for GFAP (red) was detected.

Preparation of neuronal and glial cultures. Cerebral cortices were prepared from 15.5 days postcoitum (15.5 dpc) embryos of CD-1 mice. The procedure of Yamasaki et al. (Yamasaki et al. Hum Mol Genet. 12: 837-847, 2003) was used. Briefly, fetal cerebral cortices without meninges were dissociated by mechanical trituration and digested with 0.25% trypsin with EDTA. After adding fetal bovine serum (FBS; GIBCO BRL), filtered cells were collected by centrifugation. The cell pellet was resuspended in Neurobasal (GIBCO BRL) medium supplemented with B-27 (GIBCO BRL) for growth of neurons or with G-5 (GIBCO BRL) for growth of glial cells. Cells were plated on polyethyleneimine-coated plastic dishes at a density of $2 \times 10^6$ cells/ ml. Cultures of neurons and glial cells were maintained in 5% $CO_2$ at 37° C. for 6 days and 12 days, respectively. Isolated brain cells were characterized by RT-PCR and immunofluorescence (IF) using the markers MAP2 (microtubule-associated protein 2) for neurons, GFAP (glial fibrillary acidic protein) for glial cells and NESTIN for progenitor cells. For IF, the following specific antibodies were used: mouse monoclonal anti-MAP2 (CHEMICON), and rabbit polyclonal anti-GFAP (DAKO). The primers used for rtPCR were same as Yamasaki et al. To obtain a semi-quantitative PCR, optimal cDNA concentration and number of cycles were determined according to Gapdh amplification as an internal control. FIG. 4 shows the characterization of the primary brain cell cultures by rtPCR (A) and IF (B).

Quantitative rtPCR. To determine the quantity of the MECP2 transcripts in different tissues, we developed transcript-specific real-time quantitative PCR assays using SYBR Green detection method (PE Applied Biosystems, ABI PRISM 7900 Sequence Detection System). The following MECP2E2-specific forward primer (25 nM) (in exon 2) was designed: 5'-ctcaccagttcctgctttgatgt-3' (SEQ ID No. 12). The MECP2E1-specific primer (25 nM) was placed at the junction of exons 1 and 3: 5'-aggagagactggaagaaaagtc-3' (SEQ ID No. 10). Both assays used the same reverse primer (25 nM) in exon 3: 5'-cttgaggggtttgtccttga-3' (SEQ ID No. 11), producing fragments of 161—(MECP2E2) and 65-bp (MECP2E1). The corresponding transcript-specific primers (25 nM) for the mouse mecp2 transcripts (mecp2e2 167 by and mecp2e1 71 bp) were 5'-ctcaccagttcctgctttgatgt-3' (SEQ ID No. 12) (MECP2E2); 5'-aggagagactggaggaaaagtc-3' (SEQ ID No. 13) (MECP2E1) and the common reverse primer 5'-cttaaacttcagtggcttgtctctg-3' (SEQ ID No. 14). PCR conditions were: 2 min 50 C, 10 min 95 C and 40 cycles of 15 sec 95 C, 85 s 60 C. The PCR reactions were performed in separate tubes; and absolute quantitation of the MECP2E2 and E1 transcripts was performed from cDNA from human adult brain, cerebellum, fibroblast and lymphoblast (Clontech, Palo Alto, USA), as well as from murine neuronal and glial cell cultures (see above). Results were analyzed using the standard curve method according to the manufacturer's instructions (PE Applied Biosystems, ABI PRISM 7900 Sequence Detection System). The standard curve was developed using dilutions of the transcript-specific purified PCR products.

Immunofluorescence light microscopy. 3'-myc-tagged MECP2E2 and MECP2E1 constructs (pcDNA3.1A-

MECP2E2-myc and pcDNA3.1A-MECP2E1-myc) were generated by PCR amplification of full-length cDNA of each transcript with BamHI (5') and XbaI (3') restriction sites attached and subsequent cloning in-frame with myc into pcDNA3.1 version A (Invitrogen). The forward primer for MECP2E2 contained the start codon in exon 2 (5'-tatggatccATGgtagctgggat-3') (SEQ ID No. 15), while the forward primer for MECP2E1 included the start codon in exon1 (5'-tatggatccggaaaATGgccg-3') (SEQ ID No. 16) (BamHI restriction site underlined, start codon uppercase). The reverse primer was the same for both amplifications (5'-gcgtctagagctaactctct-3') (SEQ ID No. 17) (XbaI restriction site underlined). The template used for PCR was small intestine cDNA for MECP2E2 and skeletal muscle cDNA for MECP2E1. pcDNA3.1A-MECP2E2-myc and pcDNA3.1A-MECP2E1-myc (2 ug) were transfected into COS-7 cells using lipofectamine (Invitrogen) and the lipid-DNA complex was exposed in DMEM (GIBCO) for 5 hours. Forty-eight hours post-transfection the cultures were rinsed in PBS and fixed for 15 min at −20° C. in an acetone: methanol (1:1) mix, blocked for 1 hour (10% BSA in PBS) and incubated with anti-myc (Santa Cruz Biotechnology, 1:50 in blocking buffer) for 45 min at room temperature. After washing with PBS, slides were incubated with secondary antibody (FITC-labeled goat anti-mouse (Jackson Immunoresearch labs), 1:400, detectable through the green filter) in blocking solution, mounted with Dako Anti-Fade and analyzed by immunofluorescence light microscopy.

MLPA analysis. MLPA was performed as described by Schouten et al., supra and as described by Schouten, supra. MECP2 test kits from MRC-Holland, Amsterdam, Netherlands (www.mrc-holland.com) were utilized and consisted of 20 probe pairs that target the four MECP2 exons, six X-linked control regions and ten autosomal control regions. Briefly, 100-200 ng of genomic DNA was denatured and hybridized with the probe mix overnight at 60° C. The following morning the paired probes were ligated using heat stable Ligase-65 at 54° C. for 15 minutes. The ligation was followed with PCR with a common primer pair that hybridizes to the terminal end of each ligation product. One PCR primer was FAM-labeled and conditions for the PCR were as follows: 95° C. 30s, 60° C. 30s and 72° C. 1 min. The resulting amplicons were analyzed on an ABI 3100 capillary electrophoresis instrument and ABI Genescan software. All data management and comparisons to normal controls were done with Excel software.

Discussion

Recently, studies in frog (*Xenopus laevis*) afforded important insight into the role of MeCP2 in neurodevelopmental transcription regulation. MeCP2 was shown to be a component of the SMRT complex involved in the regulation of genes involved in neuronal differentiation following developmental stage-specific mediation by Notch-Delta. The frog Mecp2 transcript targeted for silencing in these experiments is an orthologue of MECP2E1 (FIG. 1*f*). In fact, MeCP2E1 appears to be the only form of MeCP2 in non-mammalian vertebrates (FIG. 1*f*).

The new MeCP2 N-terminus is a distinctive 21 amino acid peptide including polyalanine and polyglycine tracts (MAAAAAAAPSGGGGGGEEERL) (SEQ ID No. 18) (FIG. 1*f*). A similar N-terminus occurs in the ERK1 (MAPK3) extracellular signal-regulated kinase (FIG. 1*f*), a key common component of multiple signal transduction pathways. Intriguingly, in neurons, both ERK1 and MeCP2 have been shown to be present in the post-synaptic compartment, in addition to the nucleus, and the former shown to translocate between the two compartments to link synaptic activity to transcriptional regulation. It is possible that MeCP2E1 similarly links synaptic function, in this case neurodevelopmental synaptic contact guidance, with transcriptional regulation. The only other proteins in which consecutive polyalanine and polyglycine tracts are found are in some members of the homeobox (HOX) family. These, like MeCP2, are developmental transcription regulators.

Finally, non-inactivating MECP2 mutations have been associated with phenotypes that overlap RTT such as mental retardation and autism. The MeCP2 variant discovered in this study is a candidate for involvement in these disorders.

Example 4

Mutations in MECP2E1 in Mental Retardation

Figure 5:
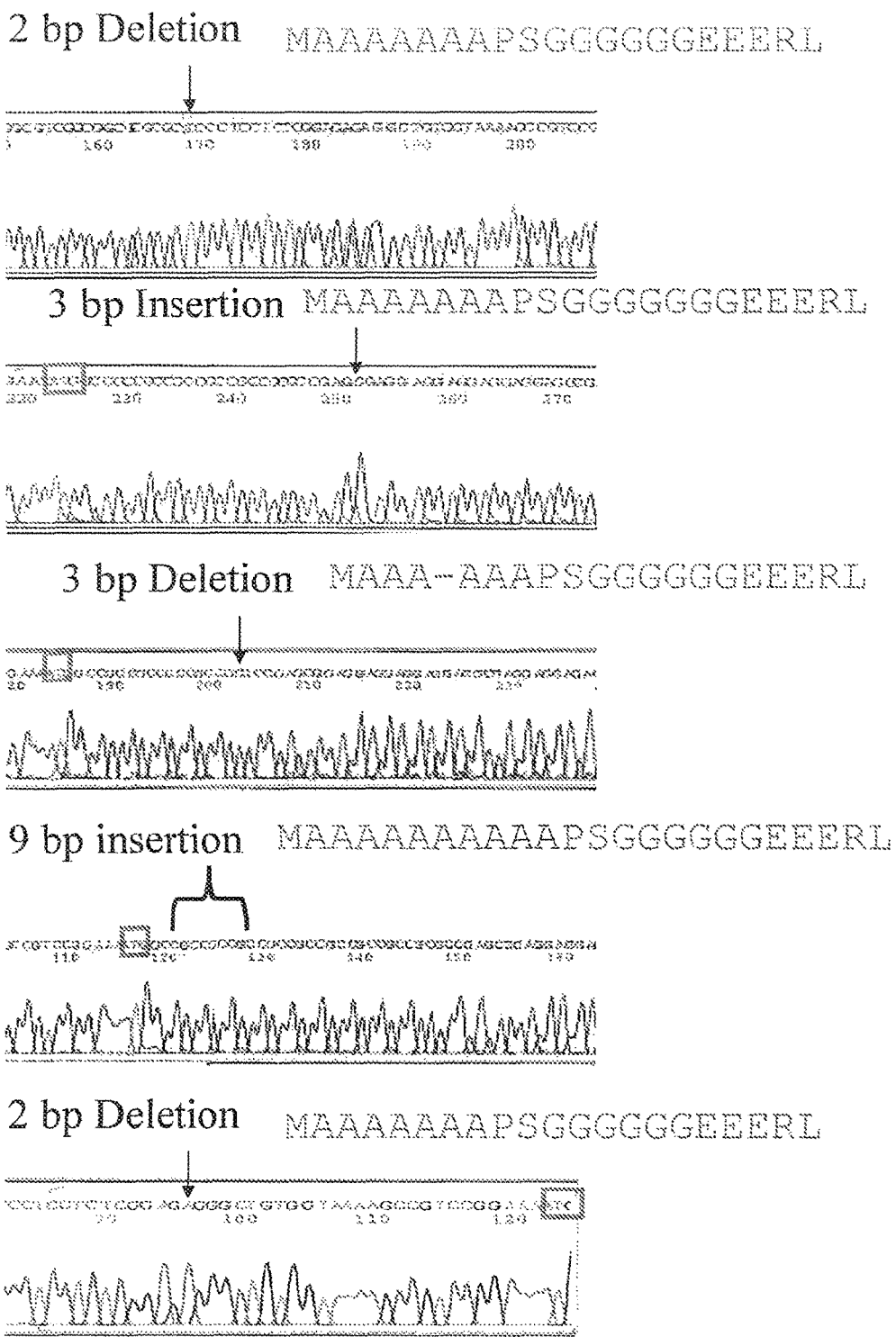
FIG. 5 shows the nucleotide sequence of the five MECP2 exon 1 variants identified in female MR patients. All sequences were obtained from single colonies, after cloning the heterozygous PCR product into the pDRIVE vector (Qiagen). The ATG start codon is indicated by a red box, where possible. The resulting amino acid sequence is also indicated, with wild type sequence shown in red, and changes indicated in green type.
Figure 6:
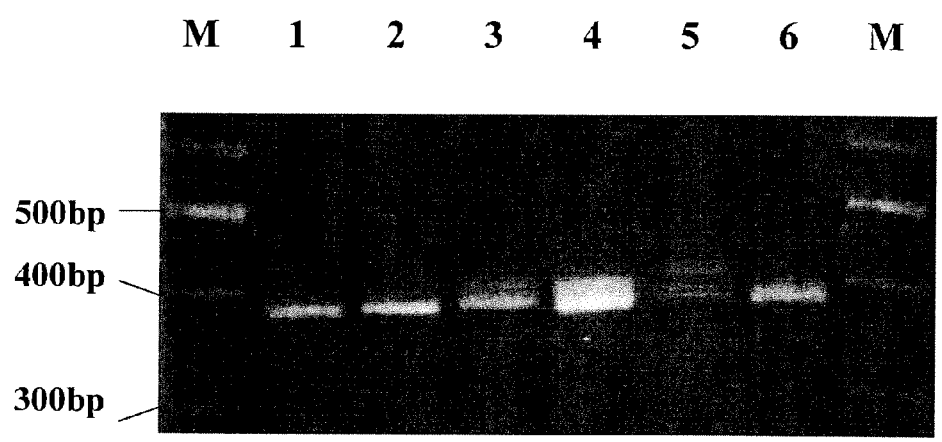
FIG. 6 shows a high resolution agarose gel (2.2%) of PCR product for MECP2 exon 1 for negative controls (Lanes 1 and 2), 3 bp insertion (Lanes 3 and 4), 9 bp insertion (Lane 5) and 2 bp deletion (Lane 6). Size ladder (M) 100 bp ladder (MBI Fermentas), flanks the PCR lanes.

The inventors screened the MECP2E1 gene in N=401 autism probands, and in N=493 patients with non-specific mental retardation. Autism probands recruited through the Hospital for Sick Children in Toronto (N=146; 114 male, 32 female) and from London, UK (N=13; 10 male, 3 female) were also screened, as well as probands from multiplex families from the Autism Genetic Resource Exchange (AGRE; N=242; 100 female, 142 male). Local institutional ethics board approval was obtained, and written consent given by participants. Anonymized DNA samples were also obtained for 293 female and 200 male patients with non-specific developmental delay/mental retardation who had been referred for fragile-X testing (but tested negative) to the Department of Pediatric Laboratory Medicine at the Hospital for Sick Children. Polymerase chain reaction followed by denaturing high performance liquid chromatography (DHPLC) was used for mutation detection, with PCR primers and conditions as described previously in Example 3. PCR product from female individuals suspected of carrying a sequence variant was cloned into the pDRIVE vector (Qiagen), and at least four clones sequenced using automated BIGDYE™ Terminator v3.1 Cycle Sequencing Kit (ABI 3100) in forward and reverse directions. PCR products from males were excised from agarose gel, column purified, then sequenced, also using automated BIGDYE™ Terminator v3.1 Cycle Sequencing Kit (ABI 3100) in both forward and reverse directions. No mutations were identified among the autism screening set, however sequence variants were identified among eight of the female MR cases (see FIG. 5), three of which result in insertion or deletion of amino acids within the polyalanine repeat stretch, and two of which result in insertion of a glycine residue within the polyglycine repeat at the N-terminal portion of MECP2E1. The first individual identified was heterozygous for a deletion of a GpC dinucleotide positioned 45-46 bp upstream of the putative MECP2E1 start codon. This deletion could disrupt a potential SP1 transcription factor binding site (as predicted using AliBaba2.1 www.gene-regulation.com/pub/programs/alibaba2/index.html), and may also eliminate potentially methylatable cytosine residues. Another individual is heterozygous for an ApG dinucleotide deletion 26 bp upstream of the MECP2E1 start codon. Two individuals are heterozygous for a GGA trinucleotide insertion within a poly[GGA] stretch, which would result in an additional glycine residue within the predicted polyglycine stretch. A fifth individual is heterozygous for a GCC trinucleotide deletion within a triplet repeat stretch encoding polyalanine. Two individuals are heterozygous for a 9 bp insertion, also within the GCC trinucleotide repeat/polyalanine region, and would result in the polyalanine stretch being extended from seven to ten residues.

The amino acid sequence variation in ~2% of female non-specific MR cases in a new isoform of a protein that has previously been associated with a mental retardation syndrome, is extremely intriguing. Moreover, the fact that the variation occurs within a part of the protein that is conserved across many vertebrate species also adds to the interest (100% identity to chimpanzee, orang-utan, macaque, cat and dog MeCP2E1 amino acid sequence). It would be particularly useful to know whether there are any specific phenotypic features among the individuals with the variants, how severe the symptoms are an whether there are overlaps with or distinctions from the Rett syndrome phenotypes. However, since the DNAs were anonymized, it is not possible, in this instance, to correlate the mutations discovered with phenotypic features or severity. In an attempt to address this issue, a second sample set of MR cases (188 female and 96 male) from the Greenwood Genetic Center, South Carolina, were screened, followed by sequencing. No variants were found in the males, and two of the females carried the GGA insertion encoding an extra glycine residue.

In the present study, three female MR patients were identified with a 3 bp insertion leading to an extra glycine residue within the polyglycine stretch at the N-terminal end of MeCP2E 1. No disease association has previously been reported with expansion within a glycine repeat. The function of polyglycine stretches, either within the context of the MeCP2E1 protein or more generally, is not known, although a study of the Toc75 protein in plants suggests that a polyglycine stretch in the protein is essential for correct targeting of the protein to the chloroplast outer envelope. A similar function of protein trafficking may also be the case for mammalian proteins with polyglycine stretches, and for MeCP2E1.

The variants within the polyalanine tracts are of particular interest, as they are rarely polymorphic, and because a number of small expansions (or duplications) within such tracts have been reported to cause diseases, ranging from cleidocranial dysplasia (RUNX2), oculopharyngeal muscular dystrophy (PABPN1) and mental retardation (ARX; this gene is also X-chromosomal and has a very broad array of phenotypes—see above). The majority of polyalanine disease genes encode transcription factors, although PABPN1 gene encodes a polyadenylate binding protein. On the one hand, amongst these diseases, the smallest pathogenic repeats within the transcription factor genes are generally greater than 20 alanines in length, thus it could be considered improbable that a stretch of alanines as short as that encoded by MECP2E1 could be pathogenic, and a change of 1 or 3 alanine residues could be considered likely to be rare polymorphisms. There is currently some uncertainty as to whether small expansion of 1 or 3 alanine residues within the ARX gene may be pathogenic or innocent variants. On the other hand, oculopharyngeal muscular dystrophy is caused by mutations within a GCG tract in the PABPN1 gene, that expand a polyalanine tract from just 10 alanine residues to between 12 and 17 alanine residues. Moreover, as with the polyalanine tract in MeCP2E1, the polyalanine tract in PABPN1 is right at the N-terminal end of the gene, and thus it is possible that smaller mutations within repeat stretches within the N-terminal portion of a protein may be more detrimental than larger mutations located in the central portions of proteins.

A recently published study screened for mutations in MECP2 exon 1 among 97 Rett patients with no mutation in exons 2, 3 or 4, and among 146 controls. One of the Rett patients was found to have a 6 bp insertion within the polyalanine-encoding [GCC] stretch, but no such variations were observed among the controls. The variant was inherited from an unaffected mother, and it was concluded that the variant is thus unlikely to be etiologically relevant. However, it has also been demonstrated recently that even subtle changes in expression of MECP2 in mice can have profound neurological and behavioural consequences. It is apparent that patients with the same MECP2 mutation may have very different phenotypic features and severity, and it is likely that variation in X-inactivation pattern plays a role in this discordancy. Thus it is quite feasible that variation in exon 1, either within the repeat stretches resulting in change in length of polyalanine or polyglycine stretch, or in the region just upstream of the start codon, may affect function or expression levels resulting in a neuropathological phenotype.

Example 5

Additional Mutations in MECP2E1 in Rett's Syndrome

The entire coding regions of exons 1, 2, 3 and 4 and their intronic flanking sequences were analyzed. Exons 2 to 4 were amplified by PCR with primer pairs designed with the use of genomic sequence information from the Human Genome Project working draft site (UCSC, www.genome.ucsc.edu) and the Lasergene Primer select program. The PCR products were loaded on 2% agarose gel to confirm amplification before analysis for base changes by dHPLC (WAVE Nucleic Acid Fragment Analysis System from Transgenomic, San Jose, Calif.). Solvent A consisted of 0.1 mol/L triethylammonim acetate (TEAA) and 25% acetonitrile and solvent B contained 1M TEAA, 25% acenonitril. PCR products showing a chromatographic variation on dHPLC were sequenced directly on an automatic sequencer (Gene Reader 4200). The sequencing data was analyzed using DNA Star software SeqMan (Lasergene). Exon 1 was PCR amplified and sequenced in all patients as recently described.

The first exon 1 mutation consists of two missing base pairs at the exon 1 intron 1 boundary. Because of the nature of the sequence in this region, we cannot resolve whether the missing two nucleotides are the first two base pairs of intron 1 (GT) or the last nucleotide of exon 1 (T) and the first nucleotide of intron 1 (G). In either case, the missing pair of nucleotides destroys the predicted consensus splice site and results in read through of intron 1 (data not shown). In the second patient with an exon 1 mutation a 1A-3T substitution (ATG->TTG) changes the first Methionine codon into a Leucine. The prediction is that MECP2E1 translation would be greatly or totally hindered due to absence of a start codon. MECP2E2 would be normally made (and appears unable to rescue the disease phenotype).

Example 6

Additional Mutations in MECP2E1 in Rett's Syndrome

Patients

Thirty-five samples from females were referred to Children's Mercy Hospital for RTT testing in a two year period spanning September of 2004 through September of 2006 (See, for example, Saunders, C. J., et al., "Novel Exon 1 Mutations in MECP2 Implicate Isoform MeCP2_e1 in Classical Rett Syndrome," *American Journal of Medical Genetics*, 149A: 1019-1023 (2009)). These patients had various clinical presentations, including autism, mental retardation, developmental delay, and "Angelman-like", and only 9 patients fit the criteria for classical (N=7) or variant (N=2) RTT. Permission to review patient charts was obtained through the Children's Mercy Hospitals and Clinics' Institutional Review Board. In addition, 16 female patients were ascertained through either the Hospital for Sick Children or Centre for Addiction and Mental Health in Toronto, either with autism and developmental delay (N=14) or Rett syndrome (N=2). This ascertainment was subsequent to the study reported by Mnatzakanian, G. et al., "A previously unidentified MECP2 open reading frame defines a new protein isoform relevant to Rett syndrome," *Nat. Genet.*, 36: 339-341 (2004) and there is no overlap of subjects between that and the current study. Screening for mutations in MECP2 identified four patients with mutations involving exon 1.

Patient 1 was a 20-year-old at the time of testing who had a long standing clinical diagnosis of RTT but had never undergone confirmatory DNA testing. She met the criteria for classical RTT, with the exception of acquired microcephaly (head circumference is at 15%). Following normal perinatal development, she sat at 6 months, walked at 14 months, used simple words at 18 months, around which time she began to regress. She lost all speech in addition to purposeful hand movements, which were replaced by a sifting activity. She now walks with a shuffling gait, exhibits some aggressive behavior, is nonverbal, and has medically intractable epilepsy.

Patient 2 was 7 years old at the time of testing. She met the criteria for classical RTT, with the exception of acquired microcephaly (head circumference 50%). She had a period of normal development, such as smiling, rolling over, and sitting at appropriate times, but around 10 months she exhibited global developmental delay. There was no clear regression in her skills at that point. Around the age of 2, she developed a stereotypic midline hand movement involving her left hand in her mouth and her right hand twirling her hair or rubbing her hair between her fingers. She commando crawls for mobility and will take steps with assistance. She is very hirsute and has precocious puberty with pubic hair development beginning at age 5. She has episodic seizures that do not require daily medication. She had previously tested negative for MECP2 mutations in exons 2-4, MECP2 duplications and deletions, and research testing involving sequencing of the MECP2 promoter region. The family came to the clinic in pursuit of mutation screening for the cyclin-dependent kinase-like 5 (CDKL5) gene, but upon closer examination of the patient's medical record, it was discovered that exon 1 of MECP2 had not been sequenced.

Patient 3 was a 16-year-old female with a clinical diagnosis of Rett syndrome since 20 months of age. She had microcephaly, developmental regression, severe cognitive insufficiency, midline hand movements, general tonic-clonic seizure disorder, loss of gait, diffuse hypertonicity, scoliosis treated with surgery, GE reflux requiring gastrostomy tube, and multiple hospitalizations for bacterial pneumonia. On her last admission for pneumonia, she succumbed to respiratory insufficiency and was not resuscitated. Brain autopsy showed microencephaly, subpial gliosis, minimal loss of Purkinje cells with gliosis, and isolated eosinophilic neurons in the dentate nucleus and brain stem. Previous testing for MECP2 exons 2-4 was negative.

Patient 4 had a clinical diagnosis of Rett syndrome since age 10. At birth, she had a normal head circumference but poor muscle tone. Global developmental delays, intense eye contact and screaming spells were noted in infancy. Teeth grinding, hand flapping, and deterioration in fine motor skills began from age 3 to 4. Speech development was slow but she acquired a vocabulary of about 25 words before the onset of loss of speech at age 6 and she became non-verbal by age 10. She first walked at age 14 months following intensive physiotherapy, and still walks unassisted despite occasional loss of balance due to mild gait dyspraxia. Other significant medical history included scoliosis (treated with surgery) and chronic constipation. There is no history of seizures or acquired microcephaly. When the patient was 28 years old, the family sought molecular genetic testing to confirm the clinical diagnosis of Rett syndrome.

Research ethics board approval was obtained for the study, and written consent obtained for the four patients described here.

Sequence Analysis

DNA from blood, or in the case of patient 3, cultured fibroblast cells, was extracted by a manual salting out procedure (Lahiri, D.K. and Nurnberger, J.I., "A rapid non-enzymatic method for the preparation of HMW DNA from blood for RFLP studies," *Nucleic Acids Res.*, 19: 5444 (1991)). For most of the 35 subjects the entire MECP2 coding region (exons 1-4) was analyzed (primers and PCR conditions available upon request); for Patients 2 and 3, only exon 1 was analyzed since the remaining coding region had been previously tested by an outside laboratory. Exon 1 of the MECP2 gene was PCR-amplified as described previously (Mnatzakanian, G. et al., "A previously unidentified MECP2 open reading frame defines a new protein isoform relevant to Rett syndrome," *Nat. Genet.*, 36: 339-341 (2004)) and verified on a 2% agarose gel. Fragments were purified using ExoSAPit (USB Corp., Cleveland Ohio). Purified products were sequenced in both forward and reverse directions by automated fluorescent dye-terminator sequencing using Big Dye v3.0 (Applied Biosystems, Foster City, Calif.) and run on an ABI310 (Applied Biosystems). For Patient 2, allele-specific sequence was obtained after cloning the heterozygous PCR product into a TA cloning vector (Invitrogen, Carlsbad, Calif.). The sequence data was compared to the MECP2 reference sequence AF030876 using Sequencher software (Gene Codes, Ann Arbor, Mich.).

In silica analysis of efficiency of translation start sites affected by exon 1 mutations was performed on MEPC2 mRNA sequences using NetStart (www.cbs.dtu.dk/services/NetStart).

X-Chromosome Inactivation

X-chromosome inactivation was assessed on genomic DNA from peripheral blood leukocytes by methylation-sensitive restriction digestion followed by PCR amplification across the androgen receptor [CAG] repeat region, according to the method described by Plenge, R. M. et al., "Skewed X-chromosome inactivation is a common feature of X-linked mental retardation disorders," *Am J Hum Genet.*, 71: 168-173 (2002).

Results

In 51 samples tested for RTT, four unrelated patients with exon 1 mutations were identified.

In Patient 1, a mutation was detected, c.1A>T in SEQ ID No. 1 that disrupts the initiation codon, changing it to a leucine. SEQ ID No. 1 contains non-coding exon sequence upstream of the start codon, so the mutation is located at position 8 in SEQ ID No. 1 which corresponds to the first position in the coding exon of SEQ ID No. 1. In silica analysis of translation initiation using NetStart predicts that translation of MeCP2_e1 would be ablated, but without any negative affect on translation of MeCP2_e2. The patient's mother tested negative for this mutation, however the father's DNA was not available for testing. X-chromosome inactivation in peripheral blood leukocytes appeared to be random.

Patient 2 has a mutation, c.62+1delTG in SEQ ID No. 1, affecting the splice donor (Amir, R E et al., "Mutations in exon 1 of MECP2 are a rare cause of Rett syndrome," *J Med. Genet.*, 42: e15 (2005)). SEQ ID No. 1 contains non-coding exon sequence upstream of the start codon, so the mutation is located at positions 69 and 70 in SEQ ID No. 1 which corresponds to positions 62 and 63 in the coding exon of SEQ ID No. 1. Analysis of parental DNA revealed that it arose as a de novo mutation, not present in either parent. This mutation is predicted to disrupt splicing of the MECP2E1 mRNA, and may also affect the translation of the MeCP2_e2 isoform from the exon 2-containing mRNA, MECP2E2 (Amir, R E. et al., "Mutations in exon 1 of MECP2 are a rare cause of Rett syndrome," *J Med. Genet.*, 42: e15 (2005) and Saxena, A. et al., "Lost in translation: translational interference from a recurrent mutation in exon 1 of MECP2,"*J Med. Genet.*, 43: 470-477 (2006)). This patient had a random pattern of X-chromosome inactivation in peripheral blood leukocytes.

Patient 3 had a C>T transition (c.5C>T) in SEQ ID No. 1 resulting in a missense mutation, A2V. SEQ ID No. 1 contains non-coding exon sequence upstream of the start codon, so the mutation is located at position 12 in SEQ ID No. 1 which corresponds to the fifth position in the coding exon of SEQ ID No. 1. Though an alanine to valine substitution is conservative in retaining a nonpolar side chain, this is a residue that is perfectly conserved throughout evolution and marks the beginning of a polyalanine stretch which is present in all vertebrate species (Harvey, C. G. et al., "Sequence Variants Within Exon 1 of MECP2 Occur in Females With Mental Retardation," *Am J Med Genet (Neuropsychiatr Genet)*, 144: 355-360 (2007)). Though the role of this repeat is unknown, it contains multiple binding sites for the SP1 transcription factor, the alterations of which would affect the rate of gene transcription. This patient's parents both tested negative for this mutation, indicating this is a de novo mutation.

Patient 4 had a A>G transition (c.1 A>G) in SEQ ID No. 1 resulting in the start methionine codon being substituted by a valine codon. SEQ ID No. 1 contains non-coding exon sequence upstream of the start codon, so the mutation is located at position 8 in SEQ ID No. 1 which corresponds to the first position in the coding exon of SEQ ID No. 1. Both parents were negative for this mutation. As with Patient 1, this mutation is predicted to ablate translation of MeCP2_e1, but without any negative affect on translation of MeCP2_e2. X-chromosome inactivation in peripheral blood leukocytes showed skewing, 90:10.

The presence of these missense/start codon mutations in classic Rett patients, uniquely affecting the MeCP2_e1 isoform, clearly indicates the importance of this isoform in the etiology of Rett syndrome. None of these sequence changes were identified in a previous study that screened MECP2 exon 1 in 1,811 subjects with developmental delay or autism, and 498 healthy adult control individuals (Harvey, C. G. et al., "Sequence Variants Within Exon 1 of MECP2 Occur in Females With Mental Retardation," *Am J Med Genet (Neuropsychiatr Genet)*, 144: 355-360 (2007)).

Discussion

MECP2 was sequenced in 51 females with various clinical presentations, including developmental delay, autism, atypical and classical RTT, referred to the laboratory for testing. In patients with identified mutations, X-chromosome inactivation was analyzed. Four patients were identified with exon 1 mutations (c.1A>T; c.1A>G; c.5C>T), two of which affected the start codon, one a missense change, and one patient had a previously reported splice site mutation, c.62+1delGT. The 4 patients fit criteria for classical RTT, and thus these findings add support to previous reports that exon 1 mutations may be associated with a severe phenotype. Also, these findings add significant weight to the mounting evidence suggesting that the MeCP2_e1 isoform is the etiologically relevant form of the protein.

As discussed above, three mutations were detected within exon 1 of the MECP2 gene in 35 clinical samples referred to CMH for MECP2 sequencing, and in one out of 16 samples from the Toronto patient set. All four were associated with classical RTT. Two of these patients had previously tested negative by molecular testing, which at the time included sequencing of exons 2-4 of the MECP2 gene. Following the reports of the second MeCP2 isoform (MeCP2_e1) and the clinical utility of sequencing exon 1, these patients were tested for exon 1 mutations. The total number of distinct exon 1 mutations detected by sequencing is now 10. Two of these mutations, c.47_57del11nt and c.62+1delGT, have been found in more than one patient (see Table 2). This brings the number of Rett patients known to have a mutation within exon 1 of MECP2 to 14.

All mutations localized to exon 1 reported until recently have been either small insertions or deletions or large deletions removing the entire exon. The c.1A>T and c.1A>G mutations, which are single base pair changes, are the first point mutations to be reported in exon 1 of the MECP2 gene (also see Gauthier, J. et al., "Clinical stringency greatly improves mutation detection in Rett syndrome," *Can J Neurol Sci*, 32: 321-6 (2005)). The c.1A>T and c.1A>G mutations alter the initiation codon, which would mostly likely result in absent translation of MeCP2_e1. MeCP2_e2 would be presumably unaffected but is clearly unable to compensate, as evidenced by the patients' classic RTT symptoms. Patient 3 had a C>T transition (c.5C>T) resulting in a missense mutation, A2V. This alanine is a perfectly conserved residue that marks beginning of a polyalanine stretch that is present in all vertebrate species (Harvey, C. G. et al., "Sequence Variants Within Exon 1 of MECP2 Occur in Females With Mental Retardation," *Am J Med Genet (Neuropsychiatr Genet)*, 144: 355-360 (2007)). The role of this repeat is unknown, but it could play a role in the regulation of gene transcription, given the multiple binding sites for the SP1 transcription factor. This patient's parents both tested negative for this mutation, indicating this is a de novo, most likely pathogenic mutation. This also emphasizes the functional importance of the N-terminal portion of MeCP2_e1. There are a number of lines of evidence pointing to the likelihood that the MeCP2_e1 isoform is more relevant to RTT etiology than MeCP2_e2: a) no exon 2 missense mutations (which should only affect MeCP2_e2) have been identified to date; b) MeCP2_e 1 is the predominant isoform expressed in neuronal tissues Kriaucionis, S, and Bird, A., "The major form of MECP2 has a novel N-terminus generated by alternative splicing," *Nucleic Acids Res*, 32: 1818-1823 (2004); Mnatzakanian, G. et al., "A previously unidentified MECP2 open reading frame defines a new protein isoform relevant to Rett syndrome," *Nat. Genet.*, 36: 339-341 (2004)); c) MeCP2_e1 appears to be the ancestral form of the gene-MeCP2_e2 is only found among the higher vertebrates (Mnatzakanian, G. et al., "A previously unidentified MECP2 open reading frame defines a new protein isoform relevant to Rett syndrome," *Nat. Genet.*, 36: 339-341 (2004) and Harvey, C. G. et al., "Sequence Variants Within Exon 1 of MECP2 Occur in Females With Mental Retardation," *Am J Med Genet (Neuropsychiatr Genet)*, 144: 355-360 (2007). On the other hand, analysis of the MECP2 exon 1 11bp deletion (c.47_57del11nt (p.Gly16Glufs)) identified in a number of studies (Mnatzakanian, G. et al., "A previously unidentified MECP2 open reading frame defines a new protein isoform relevant to Rett syndrome," *Nat. Genet.*, 36: 339-341 (2004); Amir, R. E. et al., "Mutations in exon 1 of MECP2 are a rare cause of Rett syndrome," *J Med. Genet.*, 42: e15 (2005); Saxena, A. et al., "Lost in translation: translational interference from a recurrent mutation in exon 1 of MECP2," *J Med. Genet.*, 43: 470-477 (2006); and Ravn, K. et al., "Mutations found within exon 1 of MECP2 in Danish patients with Rett syndrome," *Clin Genet.*, 67: 532-533 (2005)) has suggested that both isoforms of MeCP2 are disrupted in these patients, and thus could not exclude a role for MeCP2_e2 in RTT etiology (Saxena, A. et al., "Lost in translation: translational interference from a recurrent mutation in exon 1 of MECP2," *J Med. Genet.*, 43: 470-477 (2006)). However, the missense and start codon mutations, where only MeCP2_e1 is likely disrupted, cast further doubt on a role for MeCP2_e2 in the disorder.

Previous studies have concluded that sequencing exon 1 contributes little to the mutation detection rate in RTT, even in pre-selected populations such as classical RTT patients who had already tested negative for mutations in exons 2-4 of the gene (Amir, R. E. et al., "Mutations in exon 1 of MECP2 are a rare cause of Rett syndrome," *J Med. Genet.*, 42: e15 (2005); Evans, J. C. et al., "Variation in exon 1 coding region and promoter of MECP2 in Rett syndrome and controls," *Eur J Hum Genet.*, 13: 124-126 (2005); and Quenard, A. et al., "Deleterious mutation in exon 1 of MECP2 in Rett syndrome," *Eur J Med. Genet.*, 49: 313-322 (2006)). However, the results of the study described herein, which spanned two years with a total of 51 female patients tested, a minority of whom met the clinical criteria for classical RTT (9) or variant RTT (2), were quite different. Other clinical presentations such as autism or developmental delay were much more frequent in this testing population, which would be less likely to be associated with a MECP2 mutation. Seven other studies examining the exon 1 mutation frequency in Rett females have been published to date (see Table 3). All of these studies were restricted to patients meeting criteria for classic or variant RTT and except for one study (Quenard, A. et al., "Deleterious mutation in exon 1 of MECP2 in Rett syndrome," *Eur J Med Genet.*, 49: 313-322 (2006)), all were looking at patients who had previously tested negative for mutations in exons 2-4. The detection rates for mutations within exon 1 range from 0% to 25% (See Table 3) in these studies, with several groups concluding that exon 1 mutations are a rare cause of RTT (Amir, R. E. et al., "Mutations in exon 1 of MECP2 are a rare cause of Rett syndrome," *J Med. Genet.*, 42: e15 (2005); Evans, J. C. et al., "Variation in exon 1 coding region and promoter of MECP2 in Rett syndrome and controls," *Eur J Hum Genet.*, 13: 124-126 (2005); and Quenard, A. et al., "Deleterious mutation in exon 1 of MECP2 in Rett syndrome," *Eur J Med. Genet.*, 49: 313-322 (2006)). In this study of 51 unselected patients, 4 had exon 1 mutations (7.8%). For the sake of comparison, if the numbers are restricted to only those patients who fit the classic or atypical RTT criteria, then the exon 1 mutation frequency is 36%. The average detection rate from the reports listed in Table 3 is 8.1% (median 5%). Taken together, these data indicate that exon 1 mutations detectable by sequencing are slightly more common than previously reported (Amir, R. E. et al., "Mutations in exon 1 of MECP2 are a rare cause of Rett syndrome," *J Med. Genet.*, 42: e15 (2005); Evans, J. C. et al., "Variation in exon 1 coding region and promoter of MECP2 in Rett syndrome and controls," *Eur J Hum Genet.*, 13: 124-126 (2005); and Quenard, A. et al., "Deleterious mutation in exon 1 of MECP2 in Rett syndrome," *Eur J Med. Genet.*, 49: 313-322 (2006)).

Although genotype-phenotype correlations are difficult to make in RTT because of differences in X-chromosome inactivation (XCI), several authors have observed that patients with exon 1 mutations result in a severe RTT phenotype (Amir, R. E. et al., "Mutations in exon 1 of MECP2 are a rare cause of Rett syndrome," *J Med. Genet.*, 42: e15 (2005); Bartholdi, D. et al., "Clinical profiles of four patients with Rett syndrome carrying a novel exon 1 mutation or genomic rearrangement in the MECP2 gene," *Clin Genet.*, 69: 319-326 (2006); and Chunshu, Y. et al., "A patient with classic Rett syndrome with a novel mutation in MECP2 exon 1," *Clin Genet.*, 70: 530-531 (2006)). This could be because exon 1 mutations cause premature truncation of the more relevant, brain-dominant isoform (Kriaucionis, S, and Bird, A., "The major form of MECP2 has a novel N-terminus generated by alternative splicing," *Nucleic Acids Res*, 32: 1818-1823 (2004) and Mnatzakanian, G. et al., "A previously unidentified MECP2 open reading frame defines a new protein isoform relevant to Rett syndrome," *Nat. Genet.*, 36: 339-341 (2004)).

Out of the 14 patients harboring mutations within exon 1, all but two had classic/severe RTT. The two patients with atypically mild RTT had the same c.47_57del11nt mutation, which has also been reported in classic RTT patients (Table 2), differences for which could be attributed to skewed XCI. All four of the patients in this study had classic RTT, with one dying at an early age from pneumonia at the age of 16. Although the numbers are too small to be of any statistical significance, it is worth noting that 4 of the 14 patients listed in Table 2 died by the age of 25 (median age 17.5). RTT patients do have a decreased survival compared to the general population, but survival to 20 years was 94% in a preliminary study of patients from Texas (del Junco, D. et al., "Survival in a large cohort of US girls and women with Rett syndrome,". *J Child Neurol.*, 8:101-102 (1993), Abstract.) and 85.3% in a large Australian cohort of 276 RTT patients (Laurvick, C. L. et al., "Rett syndrome in Australia: a review of the epidemiology,". *J Pediatr,* 148: 347-352 (2006)).

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

MECP2E1 mutations or variants identified to date.

| Nucleotide change | Position relative to NM_004992 (SEQ ID No. 1) | Amino acid change | Effect of change | Associated phenotype | Number of Patients with mutation |
|---|---|---|---|---|---|
| 11 bp deletion | Between 38 to 54 | Frameshift leads to nonsense mutation, premature truncation of protein after amino acid 36 | MECP2E1 disrupted, MECP2E2 not disrupted | Rett | 1 |
| Exon 1 deletion | 1-69 | No MECP2E1 translation | MECP2E1 and MECP2E2 disrupted | Rett | 1 |
| 1A->T | 8 | 1Met->Leu | MECP2E1 disrupted, MECP2E2 possibly diminished | Rett | 1 |
| del [TG] | 69 to 70 | Destroys exon1/intron 1 splice site, resulting in read through and nonsense translation, with truncation after amino acid 97 | MECP2E1 disrupted, MECP2E2 probably not disrupted | Rett | 1 |
| ins [GCCGCCGCC] | Between nt 11 and 29 | ins[Ala]3 within N terminal polyalanine stretch of MECP2E1 | May affect function and or translation of MECP2E1, but not MECP2E2 | Developmental Delay | 2 |
| del [GCC] | Between nt 11 and 29 | del Ala within N terminal polyalanine stretch of MECP2E1 | May affect function and or translation of MECP2E1, but not MECP2E2 | Developmental Delay | 1 |
| ins [GGA] | Between 38 to 54 | ins Gly | May affect function and or translation of MECP2E1, but not MECP2E2 | Developmental Delay | 5 |
| −45 del [GC] | −38 to −39 relative to BX538060 | In 5'UTR, 45nt upstream of START codon-potential SP1 transcription factor binding site | May affect transcription or translation of MECP2E1 | Developmental Delay | 1 |
| −26 del [AG] | −19 to −20 relative to BX538060 | In 5'UTR, 26nt upstream of START codon | May affect transcription or translation of MECP2E1 | Developmental Delay | 1 |

"del" indicates a deletion;
"ins" indicates an insertion

TABLE 2

Summary of reported exon 1 sequence mutations in MECP2 to date.

| Mutation | Patient Age | Age at Death (Cause) | XCI | RTT Phenotype |
|---|---|---|---|---|
| c.1A > T (p.Met1?) | 20 | n/a | 63:37 | classic |
| c.1A > G (p.Met1?) | 28 | n/a | 90:10 | classic |
| c.5C > T (p.A2V) | | 16 (pneumonia) | Not done | classic |
| c.23_27dup5nt (p.Ser10Argfs) | | 25 (not given) | — | classic |
| c.30delCinsGA (p.Ser10Argfs) | | 19 (pneumonia) | 70:30 | classic |
| c.47_57del11nt (p.Gly16Glufs) | 27 | n/a | — | classic |
| c.47_57del11nt (p.Gly16Glufs) | 37 | n/a | — | classic |
| c.47_57del11nt (p.Gly16Glufs) | ? | n/a | 44:56 | atypical (mild) |
| c.47_57del11nt (p.Gly16Glufs) | 13 | n/a | 73:27 | atypical (mild) |
| c.48_55dup (p.Glu19Alafs) | 5 | n/a | Random | classic |
| c.59_60delGA (p.Arg20Thrfs) | 5 | n/a | 48:52 | classic |
| c.62 + 1delGT | 8 | n/a | 68:32 | classic |
| c.62 + 1delGT | 7 | n/a | 78:22 | classic |
| c.62 + 2_62 + 3del | | 6½ (not given) | Random | atypical (severe) |

TABLE 3

Literature reports of exon 1 mutation frequency in females with RTT and variant RTT phenotype.

| Frequency of Mutations in Exon 1 | Phenotype | Previously Negative for Exons 2-4 | Large Gene Rearrangements Including Exon 1 |
|---|---|---|---|
| 1/19; 5.2% | Typical RTT | Yes | 1 patient, exon 1 |
| 2/63; 3.2% | 38 classic RTT, 25 atypical RTT | Yes | Not tested |
| 2/212; .9% | 211 typical RTT, 1 atypical (severe) RTT | No | 4 patients, large deletions* |
| 2/10; 20% | Typical RTT | Yes | None |
| 1/20; 5% | 12 classic RTT, 8 variant RTT, | Yes | 1 patient, exons 1-2 |
| 1/20; 5% | Classic and atypical RTT | Yes | Not tested |
| 0/97; 0% | 37 classic RTT and 60 atypical | Yes | None (Not all were tested) |
| 1/4; 25% | Classic RTT | Not specified | n/a |
| 4/51; 7.8% | 9 classical RTT, 2 variant RTT; (the rest have autism, MR, microcephaly, etc.) | 21 Patients | Not tested |
| Total: 14/496; 2.8% | | | 6 Deletions |

*One deletion including promoter and exon 1, one including exons 1-2, one including promoter and exons 1-2, and one complete gene deletion

We claim:

1. A method of detecting a point mutation in the human MECP2 gene that disrupts the initiation codon in exon 1, comprising
   (a) contacting an MECP2 nucleic acid in a sample from a human with a detectably labelled oligonucleotide that specifically hybridizes to an MECP2 nucleic acid sequence comprising a guanine at a position corresponding to nucleotide position 8 of SEQ ID NO:1 under high stringency conditions, and
   (b) detecting hybridization of the oligonucleotide to the MECP2 nucleic acid from the human, wherein detecting hybridization indicates the presence of a guanine at a position corresponding to nucleotide position 8 of SEQ ID NO:1, and wherein the mutation disrupts the initiation codon in exon 1.

2. The method according to claim 1, wherein the method further comprises: amplifying the MECP2 nucleic acid in the sample with primers X1F (5'- CCATCACAGCCAAT-GACG-3') (SEQ ID No. 19) and X1R (5'-AGGGGGAGGG-TAGAGAGGAG-3') (SEQ ID No. 20) in a polymerase chain reaction.

3. The method according to claim 1, wherein the MECP2 nucleic acid from the sample comprises SEQ ID NO:3.

4. The method of claim 1, further comprising extracting nucleic acid from the sample.

5. The method of claim 1, further comprising amplifying the nucleic acid in the sample.

6. The method according to claim 1, wherein the method further comprises performing an assay selected from the group consisting of multiplex ligation-dependent probe amplification, direct sequencing, polymerase chain reaction, reverse transcription-polymerase chain reaction, denaturing high performance liquid chromatography, electrophoretic mobility, and fluorescent in situ hybridization.

7. The method according to claim 1, wherein the oligonucleotide is detectably labelled with a radioactive label, a fluorescent compound, an enzyme, or a chemiluminescent compound.

* * * * *

SEQUENCE LISTING

```
<160> NUMBER OF SEQ ID NOS: 55

<210> SEQ ID NO 1
<211> LENGTH: 10182
<212> TYPE: DNA
<213> ORGANISM: Homo sapiens

<400> SEQUENCE: 1
ccggaaaatg gccgccgccg ccgccgccgc gccgagcgga ggaggaggag gaggcgagga      60
ggagagactg ctccataaaa atacagactc accagttcct gctttgatgt gacatgtgac     120
tccccagaat acaccttgct tctgtagacc agctccaaca ggattccatg gtagctggga     180
tgttagggct cagggaagaa aagtcagaag accaggacct ccagggcctc aaggacaaac     240
ccctcaagtt taaaaaggtg aagaaagata agaaagaaga gaaagagggc aagcatgagc     300
ccgtgcagcc atcagcccac cactctgctg agcccgcaga ggcaggcaaa gcagagacat     360
cagaagggtc aggctccgcc ccggctgtgc cggaagcttc tgcctccccc aaacagcggc     420
gctccatcat ccgtgaccgg ggacccatgt atgatgaccc caccctgcct gaaggctgga     480
cacggaagct taagcaaagg aaatctggcc gctctgctgg gaagtatgat gtgtatttga     540
tcaatcccca gggaaaagcc tttcgctcta aagtggagtt gattgcgtac ttcgaaaagg     600
taggcgacac atccctggac cctaatgatt ttgacttcac ggtaactggg agagggagcc     660
cctcccggcg agagcagaaa ccacctaaga agcccaaatc tcccaaagct ccaggaactg     720
gcagaggccg gggacgcccc aaagggagcg gcaccacgag acccaaggcg gccacgtcag     780
agggtgtgca ggtgaaaagg gtcctggaga aaagtcctgg gaagctcctt gtcaagatgc     840
cttttcaaac ttcgccaggg ggcaaggctg aggggggtgg ggccaccaca tccacccagg     900
tcatggtgat caaacgcccc ggcaggaagc gaaaagctga ggccgaccct caggccattc     960
```

-continued

```
ccaagaaacg gggccgaaag ccggggagtg tggtggcagc cgctgccgcc gaggccaaaa    1020
agaaagccgt gaaggagtct tctatccgat ctgtgcagga gaccgtactc cccatcaaga    1080
agcgcaagac ccgggagacg gtcagcatcg aggtcaagga agtggtgaag cccctgctgg    1140
tgtccaccct cggtgagaag agcgggaaag gactgaagac ctgtaagagc cctgggcgga    1200
aaagcaagga gagcagcccc aaggggcgca gcagcagcgc ctcctcaccc cccaagaagg    1260
agcaccacca ccatcaccac cactcagagt ccccaaaggc ccccgtgcca ctgctcccac    1320
ccctgccccc acctccacct gagcccgaga gctccgagga ccccaccagc ccccctgagc    1380
cccaggactt gagcagcagc gtctgcaaag aggagaagat gccagagga ggctcactgg     1440 agagcgacgg ctgccccaag gagccagcta agactcagcc cgcggttgcc accgccgcca    1500
cggccgcaga aaagtacaaa caccgagggg agggagagcg caaagacatt gtttcatcct    1560
ccatgccaag gccaaacaga gaggagcctg tggacagccg gacgcccgtg accgagagag    1620
ttagctgact ttacacggag cggattgcaa agcaaaccaa caagaataaa ggcagctgtt    1680
gtctcttctc cttatgggta gggctctgac aaagcttccc gattaactga aataaaaaat    1740
attttttttt ctttcagtaa acttagagtt tcgtggcttc agggtgggag tagttggagc    1800
attggggatg ttttcttac  cgacaagcac agtcaggttg aagacctaac cagggccaga    1860
agtagctttg cacttttcta aactaggctc cttcaacaag gcttgctgca gatactactg    1920
accagacaag ctgttgacca ggcacctccc ctcccgccca aacctttccc ccatgtggtc    1980
gttagagaca gagcgacaga gcagttgaga ggacactccc gttttcggtg ccatcagtgc    2040
cccgtctaca gctcccccag ctcccccac  ctcccccact cccaaccacg ttgggacagg    2100
gaggtgtgag gcaggagaga cagttggatt ctttagagaa gatggatatg accagtggct    2160
atggcctgtg cgatcccacc cgtggtggct caagtctggc cccacaccag ccccaatcca    2220
aaactggcaa ggacgcttca caggacagga aagtggcacc tgtctgctcc agctctggca    2280
tggctaggag gggggagtcc cttgaactac tgggtgtaga ctggcctgaa ccacaggaga    2340
ggatggccca gggtgaggtg gcatggtcca ttctcaaggg acgtcctcca acgggtggcg    2400
ctagaggcca tggaggcagt aggacaaggt gcagcaggc  tggcctgggg tcaggccggg    2460
cagagcacag cggggtgaga gggattccta atcactcaga gcagtctgtg acttagtgga    2520
caggggaggg ggcaaagggg gaggagaaga aaatgttctt ccagttactt tccaattctc    2580
ctttagggac agcttagaat tatttgcact attgagtctt catgttccca cttcaaaaca    2640
aacagatgct ctgagagcaa actggcttga attggtgaca tttagtccct caagccacca    2700
gatgtgacag tgttgagaac tacctggatt tgtatatata cctgcgcttg ttttaaagtg    2760
ggctcagcac atagggttcc cacgaagctc cgaaactcta agtgtttgct gcaattttat    2820
aaggacttcc tgattggttt ctcttctccc cttccatttc tgccttttgt tcatttcatc    2880
ctttcacttc tttcccttcc tccgtcctcc tccttcctag ttcatccctt ctcttccagg    2940
cagccgcggt gcccaaccac acttgtcggc tccagtcccc agaactctgc ctgccctttg    3000
tcctcctgct gccagtacca gccccaccct gttttgagcc ctgaggaggc cttgggctct    3060
gctgagtccg acctggcctg tctgtgaaga gcaagagagc agcaaggtct tgctctccta    3120
ggtagccccc tcttccctgg taagaaaaag caaaaggcat ttcccaccct gaacaacgag    3180
ccttttcacc cttctactct agagaagtgg actggaggag ctgggcccga tttggtagtt    3240
gaggaaagca cagaggcctc ctgtggcctg ccagtcatcg agtggcccaa caggggctcc    3300
```

-continued

```
atgccagccg accttgacct cactcagaag tccagagtct agcgtagtgc agcagggcag    3360
tagcggtacc aatgcagaac tcccaagacc cgagctggga ccagtacctg ggtccccagc    3420
ccttcctctg ctccccctttt tccctcggag ttcttcttga atggcaatgt tttgcttttg   3480
ctcgatgcag acaggggcc agaacaccac acatttcact gtctgtctgg tccatagctg     3540
tggtgtaggg gctagaggc atgggcttgc tgtgggtttt taattgatca gttttcatgt     3600
gggatcccat cttttttaacc tctgttcagg aagtccttat ctagctgcat atcttcatca   3660
tattggtata tccttttctg tgtttacaga gatgtctctt atatctaaat ctgtccaact    3720
gagaagtacc ttatcaaagt agcaaatgag acagcagtct tatgcttcca gaaacaccca    3780
caggcatgtc ccatgtgagc tgctgccatg aactgtcaag tgtgtgttgt cttgtgtatt    3840
tcagttattg tccctggctt ccttactatg gtgtaatcat gaaggagtga acatcatag     3900
aaactgtcta gcacttcctt gccagtcttt agtgatcagg aaccatagtt gacagttcca    3960
atcagtagct taagaaaaaa ccgtgtttgt ctcttctgga atggttagaa gtgagggagt    4020
ttgccccgtt ctgtttgtag agtctcatag ttggactttc tagcatatat gtgtccattt    4080
ccttatgctg taaaagcaag tcctgcaacc aaactcccat cagcccaatc cctgatccct    4140
gatcccttcc acctgctctg ctgatgaccc ccccagcttc acttctgact cttccccagg    4200
aagggaaggg gggtcagaag agagggtgag tcctccagaa ctcttcctcc aaggacagaa    4260
ggctcctgcc cccatagtgg cctcgaactc ctggcactac caaggacac ttatccacga     4320
gagcgcagca tccgaccagg ttgtcactga aagatgtttt attttggtca gttgggttt     4380
tatgtattat acttagtcaa atgtaatgtg gcttctggaa tcattgtcca gagctgcttc    4440
cccgtcacct gggcgtcatc tggtcctggt aagaggagtg cgtggcccac caggccccc     4500
tgtcacccat gacagttcat tcagggccga tggggcagtc gtggttggga acacagcatt    4560
tcaagcgtca ctttatttca ttcgggcccc acctgcagct ccctcaaaga ggcagttgcc    4620
cagcctcttt cccttccagt ttattccaga gctgccagtg gggcctgagg ctccttaggg    4680
ttttctctct atttcccccct ttcttcctca ttccctcgtc tttcccaaag gcatcacgag   4740
tcagtcgcct ttcagcaggc agccttggcg gtttatcgcc ctggcaggca ggggccctgc    4800
agctctcatg ctgcccctgc cttggggtca ggttgacagg aggttggagg gaaagcctta    4860
agctgcagga ttctcaccag ctgtgtccgg cccagttttg gggtgtgacc tcaatttcaa    4920
ttttgtctgt acttgaacat tatgaagatg ggggcctctt tcagtgaatt tgtgaacagc    4980
agaattgacc gacagctttc cagtacccat ggggctaggt cattaaggcc acatccacag    5040
tctcccccac ccttgttcca gttgttagtt actacctcct ctcctgacaa tactgtatgt    5100
cgtcgagctc cccccaggtc taccectccc ggccctgcct gctggtgggc ttgtcatagc    5160
cagtgggatt gccggtcttg acagctcagt gagctggaga tacttggtca cagccaggcg    5220
ctagcacagc tcccttctgt tgatgctgta ttcccatatc aaaagacaca ggggacaccc    5280
agaaacgcca catcccccaa tccatcagtg ccaaactagc caacggcccc agcttctcag    5340
ctcgctggat ggcggaagct gctactcgtg agcgccagtg cgggtgcaga caatcttctg    5400
ttgggtggca tcattccagg cccgaagcat gaacagtgca cctgggacag ggagcagccc    5460
caaattgtca cctgcttctc tgcccagctt ttcattgctg tgacagtgat ggcgaaagag    5520
ggtaataacc agacacaaac tgccaagttg ggtggagaaa ggagtttctt tagctgacag    5580
aatctctgaa ttttaaatca cttagtaagc ggctcaagcc caggagggag cagagggata    5640
cgagcggagt cccctgcgcg ggaccatctg gaattggttt agcccaagtg gagcctgaca    5700
```

```
gccagaactc tgtgtccccc gtctaaccac agctccttttt ccagagcatt ccagtcaggc    5760
tctctgggct gactgggcca ggggaggtta caggtaccag ttctttaaga agatctttgg    5820
gcatatacat ttttagcctg tgtcattgcc ccaaatggat tcctgtttca agttcacacc    5880
tgcagattct aggacctgtg tcctagactt cagggagtca gctgtttcta gagttcctac    5940
catggagtgg gtctggagga cctgcccggt gggggggcag agccctgctc cctccgggtc    6000
ttcctactct tctctctgct ctgacgggat ttgttgattc tctccatttt ggtgtctttc    6060
tcttttagat attgtatcaa tctttagaaa aggcatagtc tacttgttat aaatcgttag    6120
gatactgcct cccccagggt ctaaaattac atattgaagg ggaaaagctg aacactgaag    6180
tcagttctca acaatttaga aggaaaacct agaaacatt tggcagaaaa ttacatttcg      6240 atgttttga atgaatacga gcaagctttt acaacagtgc tgatctaaaa atacttagca     6300
cttggcctga gatgcctggt gagcattaca ggcaagggga atctggaggt agccgacctg    6360
aggacatggc ttctgaacct gtcttttggg agtggtatgg aaggtggagc gttcaccagt    6420
gacctggaag gcccagcacc accctccttc ccactcttct catcttgaca gagcctgccc    6480
cagcgctgac gtgtcaggaa aacacccagg gaactaggaa ggcacttctg cctgaggggc    6540
agcctgcctt gcccactcct gctctgctcg cctcggatca gctgagcctt ctgagctggc    6600
ctctcactgc ctcccccaagg cccctgcct gccctgtcag gaggcagaag gaagcaggtg   6660
tgagggcagt gcaaggaggg agcacaaccc ccagctcccg ctccgggctc cgacttgtgc    6720
acaggcagag cccagaccct ggaggaaatc ctacctttga attcaagaac atttggggaa    6780
tttggaaatc tctttgcccc caaaccccca ttctgtccta cctttaatca ggtcctgctc    6840
agcagtgaga gcagatgagg tgaaaaggcc aagaggtttg gctcctgccc actgatagcc    6900
cctctccccg cagtgtttgt gtgtcaagtg gcaaagctgt tcttcctggt gaccctgatt    6960
atatccagta acacatagac tgtgcgcata ggcctgcttt gtctcctcta tcctgggctt    7020
ttgttttgct ttttagtttt gcttttagtt tttctgtccc tttttattta acgcaccgact    7080 agacacacaa agcagttgaa ttttatata tatatctgta tattgcacaa ttataaactc      7140
attttgcttg tggctccaca cacacaaaaa aagacctgtt aaaattatac ctgttgctta    7200
attacaatat ttctgataac catagcatag gacaagggaa aataaaaaaa gaaaaaaag     7260 aaaaaaaaac gacaaatctg tctgctggtc acttcttctg tccaagcaga ttcgtggtct    7320
tttcctcgct tctttcaagg gctttcctgt gccaggtgaa ggaggctcca ggcagcaccc    7380
aggttttgca ctcttgtttc tcccgtgctt gtgaaagagg tcccaaggtt ctgggtgcag    7440
gagcgctccc ttgacctgct gaagtccgga acgtagtcgg cacagcctgg tcgccttcca    7500
cctctgggag ctggagtcca ctggggtggc ctgactcccc cagtcccctt cccgtgacct    7560
ggtcagggtg agcccatgtg gagtcagcct cgcaggcctc cctgccagta gggtccgagt    7620
gtgtttcatc cttcccactc tgtcgagcct ggggctgga gcggagacgg gaggcctggc    7680
ctgtctcgga acctgtgagc tgcaccaggt agaacgccag ggaccccaga atcatgtgcg    7740
tcagtccaag gggtcccctc caggagtagt gaagactcca gaaatgtccc tttcttctcc    7800
cccatcctac gagtaattgc atttgctttt gtaattctta atgagcaata tctgctagag    7860
agtttagctg taacagttct ttttgatcat cttttttaa taattagaaa caccaaaaaa    7920
atccagaaac ttgttcttcc aaagcagaga gcattataat caccagggcc aaaagcttcc    7980
ctccctgctg tcattgcttc ttctgaggcc tgaatccaaa agaaaaacag ccataggccc    8040
```

| | |
|---|---|
| tttcagtggc cgggctaccc gtgagccctt cggaggacca gggctggggc agcctctggg | 8100 |
| cccacatccg gggccagctc cggcgtgtgt tcagtgttag cagtgggtca tgatgctctt | 8160 |
| tcccacccag cctgggatag gggcagagga ggcgaggagg ccgttgccgc tgatgtttgg | 8220 |
| ccgtgaacag gtgggtgtct gcgtgcgtcc acgtgcgtgt tttctgactg acatgaaatc | 8280 |
| gacgcccgag ttagcctcac ccggtgacct ctagccctgc ccggatggag cggggcccac | 8340 |
| ccggttcagt gtttctgggg agctggacag tggagtgcaa aaggcttgca gaacttgaag | 8400 |
| cctgctcctt cccttgctac cacggcctcc tttccgtttg atttgtcact gcttcaatca | 8460 |
| ataacagccg ctccagagtc agtagtcaat gaatatatga ccaaatatca ccaggactgt | 8520 |
| tactcaatgt gtgccgagcc cttgcccatg ctgggctccc gtgtatctgg acactgtaac | 8580 |
| gtgtgctgtg tttgctcccc ttccccttcc tctttgccc tttacttgtc tttctggggt | 8640 |
| ttttctgttt gggtttggtt tggtttttat ttctccttt gtgttccaaa catgaggttc | 8700 |
| tctctactgg tcctcttaac tgtggtgttg aggcttatat ttgtgtaatt tttggtgggt | 8760 |
| gaaaggaatt ttgctaagta aatctcttct gtgtttgaac tgaagtctgt attgtaacta | 8820 |
| tgtttaaagt aattgttcca gagacaaata ttttctagaca ctttttcttt acaaacaaaa | 8880 |
| gcattcggag ggaggggat ggtgactgag atgagagggg agagctgaac agatgacccc | 8940 |
| tgcccagatc agccagaagc cacccaaagc agtggagccc aggagtccca ctccaagcca | 9000 |
| gcaagccgaa tagctgatgt gttgccactt tccaagtcac tgcaaaacca ggttttgttc | 9060 |
| cgcccagtgg attcttgttt tgcttccct cccccgaga ttattaccac catcccgtgc | 9120 |
| ttttaaggaa aggcaagatt gatgtttcct tgaggggagc caggagggga tgtgtgtgtg | 9180 |
| cagagctgaa gagctgggga gaatgggct gggcccaccc aagcaggagg ctgggacgct | 9240 |
| ctgctgtggg cacaggtcag gctaatgttg gcagatgcag ctcttcctgg acaggccagg | 9300 |
| tggtgggcat tctctctcca aggtgtgccc cgtgggcatt actgtttaag acacttccgt | 9360 |
| cacatcccac cccatcctcc agggctcaac actgtgacat ctctattccc cacccctcccc | 9420 |
| ttcccagggc aataaaatga ccatggaggg ggcttgcact ctcttggctg tcacccgatc | 9480 |
| gccagcaaaa cttagatgtg agaaaacccc ttcccattcc atggcgaaaa catctcctta | 9540 |
| gaaaagccat taccctcatt aggcatggtt ttgggctccc aaaacacctg acagcccctc | 9600 |
| cctcctctga gaggcggaga gtgctgactg tagtgaccat tgcatgccgg gtgcagcatc | 9660 |
| tggaagagct aggcagggtg tctgcccct cctgagttga agtcatgctc ccctgtgcca | 9720 |
| gcccagaggc cgagagctat ggacagcatt gccagtaaca caggccaccc tgtgcagaag | 9780 |
| ggagctggct ccagcctgga aacctgtctg aggttgggag aggtgcactt ggggcacagg | 9840 |
| gagaggccgg gacacactta gctggagatg tctctaaaag ccctgtatcg tattcacctt | 9900 |
| cagttttttgt gttttgggac aattacttta gaaaataagt aggtcgtttt aaaaacaaaa | 9960 |
| attattgatt gcttttttgt agtgttcaga aaaaggttc tttgtgtata gccaaatgac | 10020 |
| tgaaagcact gatatattta aaaacaaaag gcaatttatt aaggaaattt gtaccatttc | 10080 |
| agtaaacctg tctgaatgta cctgtatacg tttcaaaaac cccccccccc cactgaatcc | 10140 |
| ctgtaaccta tttattatat aaagagtttg ccttataaat tt | 10182 |

```
<210> SEQ ID NO 2
<211> LENGTH: 486
<212> TYPE: PRT
<213> ORGANISM: Homo sapiens

<400> SEQUENCE: 2
```

```
Met Val Ala Gly Met Leu Gly Leu Arg Glu Glu Lys Ser Glu Asp Gln
1               5                   10                  15

Asp Leu Gln Gly Leu Lys Asp Lys Pro Leu Lys Phe Lys Lys Val Lys
            20                  25                  30

Lys Asp Lys Lys Glu Glu Lys Glu Gly Lys His Glu Pro Val Gln Pro
        35                  40                  45

Ser Ala His His Ser Ala Glu Pro Ala Glu Ala Gly Lys Ala Glu Thr
    50                  55                  60

Ser Glu Gly Ser Gly Ser Ala Pro Ala Val Pro Glu Ala Ser Ala Ser
65                  70                  75                  80

Pro Lys Gln Arg Arg Ser Ile Ile Arg Asp Arg Gly Pro Met Tyr Asp
                85                  90                  95

Asp Pro Thr Leu Pro Glu Gly Trp Thr Arg Lys Leu Lys Gln Arg Lys
            100                 105                 110

Ser Gly Arg Ser Ala Gly Lys Tyr Asp Val Tyr Leu Ile Asn Pro Gln
            115                 120                 125

Gly Lys Ala Phe Arg Ser Lys Val Glu Leu Ile Ala Tyr Phe Glu Lys
        130                 135                 140

Val Gly Asp Thr Ser Leu Asp Pro Asn Asp Phe Asp Phe Thr Val Thr
145                 150                 155                 160

Gly Arg Gly Ser Pro Ser Arg Arg Glu Gln Lys Pro Pro Lys Lys Pro
                165                 170                 175

Lys Ser Pro Lys Ala Pro Gly Thr Gly Arg Gly Arg Gly Arg Pro Lys
            180                 185                 190

Gly Ser Gly Thr Thr Arg Pro Lys Ala Ala Thr Ser Glu Gly Val Gln
        195                 200                 205

Val Lys Arg Val Leu Glu Lys Ser Pro Gly Lys Leu Leu Val Lys Met
210                 215                 220

Pro Phe Gln Thr Ser Pro Gly Gly Lys Ala Glu Gly Gly Gly Ala Thr
225                 230                 235                 240

Thr Ser Thr Gln Val Met Val Ile Lys Arg Pro Gly Arg Lys Arg Lys
                245                 250                 255

Ala Glu Ala Asp Pro Gln Ala Ile Pro Lys Lys Arg Gly Arg Lys Pro
            260                 265                 270

Gly Ser Val Val Ala Ala Ala Ala Glu Ala Lys Lys Lys Ala Val
        275                 280                 285

Lys Glu Ser Ser Ile Arg Ser Val Gln Glu Thr Val Leu Pro Ile Lys
    290                 295                 300

Lys Arg Lys Thr Arg Glu Thr Val Ser Ile Glu Val Lys Glu Val Val
305                 310                 315                 320

Lys Pro Leu Leu Val Ser Thr Leu Gly Glu Lys Ser Gly Lys Gly Leu
            325                 330                 335

Lys Thr Cys Lys Ser Pro Gly Arg Lys Ser Lys Glu Ser Ser Pro Lys
            340                 345                 350

Gly Arg Ser Ser Ser Ala Ser Ser Pro Lys Lys Glu His His His
        355                 360                 365

His His His His Ser Glu Ser Pro Lys Ala Pro Val Pro Leu Leu Pro
        370                 375                 380

Pro Leu Pro Pro Pro Pro Glu Pro Glu Ser Ser Glu Asp Pro Thr
385                 390                 395                 400

Ser Pro Pro Glu Pro Gln Asp Leu Ser Ser Ser Val Cys Lys Glu Glu
            405                 410                 415
```

| | | | | | | | | | | | |
|---|---|---|---|---|---|---|---|---|---|---|---|
| Lys | Met | Pro | Arg | Gly | Gly | Ser | Leu | Glu | Ser | Asp | Gly | Cys | Pro | Lys | Glu |
| | | | 420 | | | | 425 | | | | 430 | | | | |
| Pro | Ala | Lys | Thr | Gln | Pro | Ala | Val | Ala | Thr | Ala | Ala | Thr | Ala | Ala | Glu |
| | | | 435 | | | | 440 | | | | 445 | | | | |
| Lys | Tyr | Lys | His | Arg | Gly | Glu | Gly | Glu | Arg | Lys | Asp | Ile | Val | Ser | Ser |
| | | | 450 | | | | 455 | | | | 460 | | | | |
| Ser | Met | Pro | Arg | Pro | Asn | Arg | Glu | Glu | Pro | Val | Asp | Ser | Arg | Thr | Pro |
| 465 | | | | | 470 | | | | 475 | | | | | 480 | |
| Val | Thr | Glu | Arg | Val | Ser | | | | | | | | | | |
| | | | | 485 | | | | | | | | | | | |

<210> SEQ ID NO 3
<211> LENGTH: 1504
<212> TYPE: DNA
<213> ORGANISM: Homo sapiens

<400> SEQUENCE: 3

```
ccggaaaatg gccgccgccg ccgccgccgc gccgagcgga ggaggaggag gaggcgagga      60
ggagagactg gaagaaaagt cagaagacca ggacctccag ggcctcaagg acaaacccct     120
caagtttaaa aaggtgaaga agataagaa agaagagaaa gagggcaagc atgagcccgt     180
gcagccatca gcccaccact ctgctgagcc gcagaggca ggcaaagcag agacatcaga     240
agggtcaggc tccgccccgg ctgtgccgga agcttctgcc tccccaaac agcggcgctc     300
catcatccgt gaccggggac ccatgtatga tgacccccacc ctgcctgaag ctggacacg     360
gaagcttaag caaggaaat ctggccgctc tgctgggaag tatgatgtgt atttgatcaa     420
tccccaggga aaagcctttc gctctaaagt ggagttgatt gcgtacttcg aaaaggtagg     480
cgacacatcc ctggacccta atgattttga cttcacggta actgggagag ggagcccctc     540
ccggcgagag cagaaaccac ctaagaagcc caaatctccc aaagctccag gaactggcag     600
aggccgggga cgccccaaag ggagcggcac cacgagaccc aaggcggcca cgtcagaggg     660
tgtgcaggtg aaaagggtcc tggagaaaag tcctgggaag ctccttgtca agatgccttt     720
tcaaacttcg ccaggggggca aggctgaggg gggtggggcc accacatcca cccaggtcat     780
ggtgatcaaa cgccccggca ggaagcgaaa agctgaggcc gaccctcagg ccattcccaa     840
gaaacgggc cgaaagccgg ggagtgtggt ggcagccgct ccgccgagg ccaaaaagaa     900
agccgtgaag gagtcttcta tccgatctgt gcaggagacc gtactcccca tcaagaagcg     960
caagacccgg gagacggtca gcatcgaggt caaggaagtg gtgaagcccc tgctggtgtc    1020
cacccctcggt gagaagagcg ggaaaggact gaagacctgt aagagccctg gcggaaaag    1080
caaggagagc agccccaagg ggcgcagcag cagcgcctcc tcacccccca gaaggagca    1140
ccaccaccat caccaccact cagagtcccc aaaggcccc gtgccactgc tcccaccct    1200
gccccacct ccacctgagc ccgagagctc cgaggacccc accagccccc ctgagcccca    1260
ggacttgagc agcagcgtct gcaaagagga agatgccc agaggaggct cactggagag    1320
cgacggctgc cccaaggagc cagctaagac tcagcccgcg gttgccaccg ccgccacggc    1380
cgcagaaaag tacaaacacc gaggggaggg agagcgcaaa gacattgttt catcctccat    1440
gccaaggcca acagagagg agcctgtgga cagccggacg cccgtgaccg agagagttag    1500
ctga                                                                 1504
```

<210> SEQ ID NO 4
<211> LENGTH: 498
<212> TYPE: PRT

<213> ORGANISM: Homo sapiens

<400> SEQUENCE: 4

| | | | | | | | | | | | | | | |
|---|---|---|---|---|---|---|---|---|---|---|---|---|---|---|
| Met | Ala | Ala | Ala | Ala | Ala | Pro | Ser | Gly | Gly | Gly | Gly | Gly |
| 1 | | | | 5 | | | | | 10 | | | | | 15 |
| Glu | Glu | Glu | Arg | Leu | Glu | Glu | Lys | Ser | Glu | Asp | Gln | Asp | Leu | Gln | Gly |
| | | | 20 | | | | | 25 | | | | | 30 |
| Leu | Lys | Asp | Lys | Pro | Leu | Lys | Phe | Lys | Lys | Val | Lys | Lys | Asp | Lys | Lys |
| | | 35 | | | | | 40 | | | | | 45 |
| Glu | Glu | Lys | Glu | Gly | Lys | His | Glu | Pro | Val | Gln | Pro | Ser | Ala | His | His |
| | 50 | | | | | 55 | | | | | 60 |
| Ser | Ala | Glu | Pro | Ala | Glu | Ala | Gly | Lys | Ala | Glu | Thr | Ser | Glu | Gly | Ser |
| 65 | | | | | 70 | | | | | 75 | | | | | 80 |
| Gly | Ser | Ala | Pro | Ala | Val | Pro | Glu | Ala | Ser | Ala | Ser | Pro | Lys | Gln | Arg |
| | | | | 85 | | | | | 90 | | | | | 95 |
| Arg | Ser | Ile | Ile | Arg | Asp | Arg | Gly | Pro | Met | Tyr | Asp | Asp | Pro | Thr | Leu |
| | | | 100 | | | | | 105 | | | | | 110 |
| Pro | Glu | Gly | Trp | Thr | Arg | Lys | Leu | Lys | Gln | Arg | Lys | Ser | Gly | Arg | Ser |
| | | | 115 | | | | | 120 | | | | | 125 |
| Ala | Gly | Lys | Tyr | Asp | Val | Tyr | Leu | Ile | Asn | Pro | Gln | Gly | Lys | Ala | Phe |
| | | 130 | | | | | 135 | | | | | 140 |
| Arg | Ser | Lys | Val | Glu | Leu | Ile | Ala | Tyr | Phe | Glu | Lys | Val | Gly | Asp | Thr |
| 145 | | | | | 150 | | | | | 155 | | | | | 160 |
| Ser | Leu | Asp | Pro | Asn | Asp | Phe | Asp | Phe | Thr | Val | Thr | Gly | Arg | Gly | Ser |
| | | | | 165 | | | | | 170 | | | | | 175 |
| Pro | Ser | Arg | Arg | Glu | Gln | Lys | Pro | Pro | Lys | Lys | Pro | Lys | Ser | Pro | Lys |
| | | | 180 | | | | | 185 | | | | | 190 |
| Ala | Pro | Gly | Thr | Gly | Arg | Gly | Arg | Gly | Arg | Pro | Lys | Gly | Ser | Gly | Thr |
| | | | 195 | | | | | 200 | | | | | 205 |
| Thr | Arg | Pro | Lys | Ala | Ala | Thr | Ser | Glu | Gly | Val | Gln | Val | Lys | Arg | Val |
| | 210 | | | | | 215 | | | | | 220 |
| Leu | Glu | Lys | Ser | Pro | Gly | Lys | Leu | Leu | Val | Lys | Met | Pro | Phe | Gln | Thr |
| 225 | | | | | 230 | | | | | 235 | | | | | 240 |
| Ser | Pro | Gly | Gly | Lys | Ala | Glu | Gly | Gly | Ala | Thr | Thr | Ser | Thr | Gln |
| | | | | 245 | | | | | 250 | | | | | 255 |
| Val | Met | Val | Ile | Lys | Arg | Pro | Gly | Arg | Lys | Arg | Lys | Ala | Glu | Ala | Asp |
| | | | 260 | | | | | 265 | | | | | 270 |
| Pro | Gln | Ala | Ile | Pro | Lys | Lys | Arg | Gly | Arg | Lys | Pro | Gly | Ser | Val | Val |
| | | 275 | | | | | 280 | | | | | 285 |
| Ala | Ala | Ala | Ala | Glu | Ala | Lys | Lys | Lys | Ala | Val | Lys | Glu | Ser | Ser |
| | | 290 | | | | | 295 | | | | | 300 |
| Ile | Arg | Ser | Val | Gln | Glu | Thr | Val | Leu | Pro | Ile | Lys | Lys | Arg | Lys | Thr |
| 305 | | | | | 310 | | | | | 315 | | | | | 320 |
| Arg | Glu | Thr | Val | Ser | Ile | Glu | Val | Lys | Glu | Val | Val | Lys | Pro | Leu | Leu |
| | | | | 325 | | | | | 330 | | | | | 335 |
| Val | Ser | Thr | Leu | Gly | Glu | Lys | Ser | Gly | Lys | Gly | Leu | Lys | Thr | Cys | Lys |
| | | | 340 | | | | | 345 | | | | | 350 |
| Ser | Pro | Gly | Arg | Lys | Ser | Lys | Glu | Ser | Ser | Pro | Lys | Gly | Arg | Ser | Ser |
| | | | 355 | | | | | 360 | | | | | 365 |
| Ser | Ala | Ser | Ser | Pro | Pro | Lys | Lys | Glu | His | His | His | His | His | His |
| | | 370 | | | | | 375 | | | | | 380 |
| Ser | Glu | Ser | Pro | Lys | Ala | Pro | Val | Pro | Leu | Leu | Pro | Pro | Leu | Pro | Pro |
| 385 | | | | | 390 | | | | | 395 | | | | | 400 |

Pro Pro Pro Glu Pro Glu Ser Ser Glu Asp Pro Thr Ser Pro Pro Glu
            405                 410                 415

Pro Gln Asp Leu Ser Ser Val Cys Lys Glu Glu Lys Met Pro Arg
        420                 425                 430

Gly Gly Ser Leu Glu Ser Asp Gly Cys Pro Lys Glu Pro Ala Lys Thr
            435                 440                 445

Gln Pro Ala Val Ala Thr Ala Ala Thr Ala Ala Glu Lys Tyr Lys His
    450                 455                 460

Arg Gly Glu Gly Glu Arg Lys Asp Ile Val Ser Ser Met Pro Arg
465                 470                 475                 480

Pro Asn Arg Glu Glu Pro Val Asp Ser Arg Thr Pro Val Thr Glu Arg
            485                 490                 495

Val Ser

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic
      HF primer

<400> SEQUENCE: 5
ctcggagaga gggctgtg                                              18

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      HR1 primer

<400> SEQUENCE: 6
cttgaggggt tgtccttga                                             20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      HR2 primer

<400> SEQUENCE: 7
cgtttgatca ccatgacctg                                            20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      MF primer

<400> SEQUENCE: 8
aggaggcgag gaggagagac                                            20

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic MR primer

<400> SEQUENCE: 9
ctggctctgc agaatggtg                                                19

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      MECP2B-specific primer

<400> SEQUENCE: 10
aggagagact ggaagaaaag tc                                            22

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      reverse primer

<400> SEQUENCE: 11
cttgaggggt ttgtccttga                                               20

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      MECP2A transcript-specific primer

<400> SEQUENCE: 12
ctcaccagtt cctgctttga tgt                                           23

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      MECP2B transcript-specific primer

<400> SEQUENCE: 13
aggagagact ggaggaaaag tc                                            22

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Synthetic
      reverse primer

<400> SEQUENCE: 14
cttaaacttc agtggcttgt ctctg                                         25

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      MECP2A forward primer

<400> SEQUENCE: 15
tatggatcca tggtagctgg gat        23

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      MECP2B forward primer

<400> SEQUENCE: 16
tatggatccg gaaaatggcc g        21

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      reverse primer

<400> SEQUENCE: 17
gcgtctagag ctaactctct        20

<210> SEQ ID NO 18
<211> LENGTH: 21
<212> TYPE: PRT
<213> ORGANISM: Artificial Sequence
<220> FEATURE:
<223> OTHER INFORMATION: Description of Artificial Sequence: Synthetic
      MeCP2 N-terminus peptide

<400> SEQUENCE: 18

Met Ala Ala Ala Ala Ala Ala Ala Pro Ser Gly Gly Gly Gly Gly Gly
1               5                   10                  15

Glu Glu Glu Arg Leu
            20

<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence: Synthetic
      X1F primer

<400> SEQUENCE: 19
ccatcacagc caatgacg        18

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      X1R primer

<400> SEQUENCE: 20 aggggggaggg tagagaggag        20

<210> SEQ ID NO 21
<211> LENGTH: 10171
<212> TYPE: DNA
<213> ORGANISM: Homo sapiens

<400> SEQUENCE: 21

| | | | | | |
|---|---|---|---|---|---|
| ccggaaaatg | gccgccgccg | ccgccgccgc | gccgagcagg | aggcgaggag | gagagactgc | 60 |
| tccataaaaa | tacagactca | ccagttcctg | ctttgatgtg | acatgtgact | ccccagaata | 120 |
| caccttgctt | ctgtagacca | gctccaacag | gattccatgg | tagctgggat | gttagggctc | 180 |
| agggaagaaa | agtcagaaga | ccaggacctc | cagggcctca | aggacaaacc | cctcaagttt | 240 |
| aaaaaggtga | agaaagataa | gaaagaagag | aaagagggca | agcatgagcc | cgtgcagcca | 300 |
| tcagcccacc | actctgctga | gcccgcagag | gcaggcaaag | cagagacatc | agaagggtca | 360 |
| ggctccgccc | cggctgtgcc | ggaagcttct | gcctccccca | aacagcggcg | ctccatcatc | 420 |
| cgtgaccggg | gacccatgta | tgatgacccc | accctgcctg | aaggctggac | acggaagctt | 480 |
| aagcaaagga | aatctggccg | ctctgctggg | aagtatgatg | tgtatttgat | caatccccag | 540 |
| ggaaaagcct | ttcgctctaa | agtggagttg | attgcgtact | tcgaaaaggt | aggcgacaca | 600 |
| tccctggacc | ctaatgattt | tgacttcacg | gtaactggga | gagggagccc | ctcccggcga | 660 |
| gagcagaaac | cacctaagaa | gcccaaatct | cccaaagctc | caggaactgg | cagaggccgg | 720 |
| ggacgcccca | agggagcgg | caccacgaga | cccaaggcgg | ccacgtcaga | gggtgtgcag | 780 |
| gtgaaaaggg | tcctggagaa | aagtcctggg | aagctccttg | tcaagatgcc | ttttcaaact | 840 |
| tcgccagggg | gcaaggctga | gggggtggg | gccaccacat | ccacccaggt | catggtgatc | 900 |
| aaacgccccg | gcaggaagcg | aaaagctgag | gccgaccctc | aggccattcc | caagaaacgg | 960 |
| ggccgaaagc | cggggagtgt | ggtggcagcc | gctgccgccg | aggccaaaaa | gaaagccgtg | 1020 |
| aaggagtctt | ctatccgatc | tgtgcaggag | accgtactcc | ccatcaagaa | gcgcaagacc | 1080 |
| cgggagacgt | tcagcatcga | ggtcaaggaa | gtggtgaagc | ccctgctggt | gtccaccctc | 1140 |
| ggtgagaaga | gcgggaaagg | actgaagacc | tgtaagagcc | ctgggcggaa | aagcaaggag | 1200 |
| agcagcccca | aggggcgcag | cagcagcgcc | tcctcacccc | ccaagaagga | gcaccaccac | 1260 |
| catcaccacc | actcagagtc | cccaaaggcc | cccgtgccac | tgctcccacc | cctgccccca | 1320 |
| cctccacctg | agcccgagag | ctccgaggac | cccaccagcc | ccctgagccc | caggacttg | 1380 |
| agcagcagcg | tctgcaaaga | ggagaagatg | cccagaggag | gctcactgga | gagcgacggc | 1440 |
| tgccccaagg | agccagctaa | gactcagccc | gcggttgcca | ccgccgccac | ggccgcagaa | 1500 |
| aagtacaaac | accgagggga | gggagagcgc | aaagacattt | tttcatcctc | catgccaagg | 1560 |
| ccaaacagag | aggagcctgt | ggacagccgg | acgcccgtga | ccgagagagt | tagctgactt | 1620 |
| tacacggagc | ggattgcaaa | gcaaaccaac | aagaataaag | gcagctgttg | tctcttctcc | 1680 |
| ttatgggtag | ggctctgaca | aagcttcccg | attaactgaa | ataaaaaata | ttttttttc | 1740 |
| tttcagtaaa | cttagagttt | cgtggcttca | gggtgggagt | agttggagca | ttggggatgt | 1800 |
| ttttcttacc | gacaagcaca | gtcaggttga | agacctaacc | agggccagaa | gtagctttgc | 1860 |
| actttctaa | actaggctcc | ttcaacaagg | cttgctgcag | atactactga | ccagacaagc | 1920 |
| tgttgaccag | gcacctcccc | tcccgcccaa | acctttcccc | catgtggtcg | ttagagacag | 1980 |
| agcgacagag | cagttgagag | gacactcccg | ttttcggtgc | catcagtgcc | ccgtctacag | 2040 |
| ctcccccagc | tcccccacc | tcccccactc | ccaaccacgt | gggacaggg | aggtgtgagg | 2100 |
| caggagagac | agttggattc | tttagagaag | atggatatga | ccagtggcta | tggcctgtgc | 2160 |
| gatcccaccc | gtggtggctc | aagtctggcc | ccacaccagc | cccaatccaa | aactggcaag | 2220 |
| gacgcttcac | aggacaggaa | agtggcacct | gtctgctcca | gctctggcat | ggctaggagg | 2280 |

```
ggggagtccc ttgaactact gggtgtagac tggcctgaac cacaggagag gatggcccag    2340
ggtgaggtgg catggtccat tctcaaggga cgtcctccaa cgggtggcgc tagaggccat    2400
ggaggcagta ggacaaggtg caggcaggct ggcctggggt caggccgggc agagcacagc    2460
ggggtgagag ggattcctaa tcactcagag cagtctgtga cttagtggac aggggagggg    2520 gcaaagggg aggagaagaa aatgttcttc cagttacttt ccaattctcc tttagggaca    2580
gcttagaatt atttgcacta ttgagtcttc atgttcccac ttcaaaacaa acagatgctc    2640
tgagagcaaa ctggcttgaa ttggtgacat ttagtccctc aagccaccag atgtgacagt    2700
gttgagaact acctggattt gtatatatac ctgcgcttgt tttaaagtgg gctcagcaca    2760
tagggttccc acgaagctcc gaaactctaa gtgtttgctg caatttata aggacttcct    2820 gattggtttc tcttctcccc ttccatttct gccttttgtt catttcatcc tttcacttct    2880
ttcccttcct ccgtcctcct ccttcctagt tcatcccttc tcttccaggc agccgcggtg    2940
cccaaccaca cttgtcggct ccagtcccca gaactctgcc tgccctttgt cctcctgctg    3000
ccagtaccag ccccaccctg ttttgagccc tgaggaggcc ttgggctctg ctgagtccga    3060
cctggcctgt ctgtgaagag caagagagca gcaaggtctt gctctcctag gtagcccct    3120 cttccctggt aagaaaaagc aaaaggcatt tcccaccctg aacaacgagc cttttcaccc    3180
ttctactcta gagaagtgga ctggaggagc tgggcccgat tggtagttg aggaaagcac    3240 agaggcctcc tgtggcctgc cagtcatcga gtggcccaac aggggctcca tgccagccga    3300
ccttgacctc actcagaagt ccagagtcta gcgtagtgca gcagggcagt agcggtacca    3360
atgcagaact cccaagaccc gagctgggac cagtacctgg gtccccagcc cttcctctgc    3420 tcccccttt ccctcggagt tcttcttgaa tggcaatgtt ttgcttttgc tcgatgcaga    3480 caggggggcca gaacaccaca catttcactg tctgtctggt ccatagctgt ggtgtagggg    3540
cttagaggca tgggcttgct gtgggttttt aattgatcag ttttcatgtg ggatcccatc    3600 ttttttaacct ctgttcagga agtccttatc tagctgcata tcttcatcat attggtatat    3660
ccttttctgt gtttacagag atgtctctta tatctaaatc tgtccaactg agaagtacct    3720
tatcaaagta gcaaatgaga cagcagtctt atgcttccag aaacacccac aggcatgtcc    3780
catgtgagct gctgccatga actgtcaagt gtgtgttgtc ttgtgtattt cagttattgt    3840
ccctggcttc cttactatgg tgtaatcatg aaggagtgaa acatcataga aactgtctag    3900
cacttccttg ccagtcttta gtgatcagga accatagttg acagttccaa tcagtagctt    3960
aagaaaaaac cgtgtttgtc tcttctggaa tggttagaag tgagggagtt tgccccgttc    4020
tgtttgtaga gtctcatagt tggactttct agcatatatg tgtccatttc cttatgctgt    4080
aaaagcaagt cctgcaacca aactcccatc agcccaatcc ctgatccctg atcccttcca    4140
cctgctctgc tgatgacccc cccagcttca cttctgactc ttccccagga agggaagggg    4200
ggtcagaaga gagggtgagt cctccagaac tcttcctcca aggacagaag gctcctgccc    4260
ccatagtggc ctcgaactcc tggcactacc aaaggacact tatccacgag agcgcagcat    4320
ccgaccaggt tgtcactgag aagatgttta ttttggtcag ttgggttttt atgtattata    4380
cttagtcaaa tgtaatgtgg cttctggaat cattgtccag agctgcttcc ccgtcacctg    4440
ggcgtcatct ggtcctggta agaggagtgc gtggcccacc aggcccccct gtcacccatg    4500
acagttcatt cagggccgat ggggcagtcg tggttgggaa cacagcattt caagcgtcac    4560
tttatttcat tcgggcccca cctgcagctc cctcaaagag gcagttgccc agcctctttc    4620
ccttccagtt tattccagag ctgccagtgg ggcctgaggc tccttagggt tttctctcta    4680
```

```
tttcccctt tcttcctcat tccctcgtct ttcccaaagg catcacgagt cagtcgcctt    4740
tcagcaggca gccttggcgg tttatcgccc tggcaggcag gggccctgca gctctcatgc    4800
tgcccctgcc ttggggtcag gttgacagga ggttggaggg aaagccttaa gctgcaggat    4860
tctcaccagc tgtgtccggc ccagttttgg ggtgtgacct caatttcaat tttgtctgta    4920
cttgaacatt atgaagatgg gggcctcttt cagtgaattt gtgaacagca gaattgaccg    4980 acagcttttcc agtacccatg gggctaggtc attaaggcca catccacagt ctcccccacc    5040
cttgttccag ttgttagtta ctacctcctc tcctgacaat actgtatgtc gtcgagctcc    5100
ccccaggtct acccctcccg gccctgcctg ctggtgggct tgtcatagcc agtgggattg    5160
ccggtcttga cagctcagtg agctggagat acttggtcac agccaggcgc tagcacagct    5220
cccttctgtt gatgctgtat tcccatatca aagacacag gggacaccca gaaacgccac    5280 atccccaat ccatcagtgc caaactagcc aacggcccca gcttctcagc tcgctggatg    5340
gcggaagctg ctactcgtga cgccagtgc gggtgcagac aatcttctgt tgggtggcat    5400
cattccaggc ccgaagcatg aacagtgcac ctgggacagg gagcagcccc aaattgtcac    5460
ctgcttctct gcccagcttt tcattgctgt gacagtgatg gcgaaagagg gtaataacca    5520
gacacaaact gccaagttgg gtggagaaag gagtttcttt agctgacaga atctctgaat    5580
tttaaatcac ttagtaagcg gctcaagccc aggagggagc agagggatac gagcggagtc    5640
ccctgcgcgg gaccatctgg aattggttta gcccaagtgg agcctgacag ccagaactct    5700
gtgtcccccg tctaaccaca gctccttttc cagagcattc cagtcaggct ctctgggctg    5760
actgggccag gggaggttac aggtaccagt tctttaagaa gatctttggg catatacatt    5820
tttagcctgt gtcattgccc caaatggatt cctgtttcaa gttcacacct gcagattcta    5880
ggacctgtgt cctagacttc agggagtcag ctgtttctag agttcctacc atggagtggg    5940
tctggaggac ctgcccggtg gggggcaga gccctgctcc ctccgggtct tcctactctt    6000
ctctctgctc tgacgggatt tgttgattct ctccattttg gtgtctttct cttttagata    6060
ttgtatcaat ctttagaaaa ggcatagtct acttgttata atcgttagg atactgcctc    6120 ccccagggtc taaaattaca tattagaggg gaaaagctga acactgaagt cagttctcaa    6180
caatttagaa ggaaaaccta gaaaacattt ggcagaaaat tacatttcga tgttttgaa    6240 tgaatacgag caagctttta caacagtgct gatctaaaaa tacttagcac ttggcctgag    6300
atgcctggtg agcattacag gcaaggggaa tctggaggta gccgacctga ggacatggct    6360
tctgaacctg tcttttggga gtggtatgga aggtggagcg ttcaccagtg acctggaagg    6420
cccagcacca ccctccttcc cactcttctc atcttgacag agcctgcccc agcgctgacg    6480
tgtcaggaaa acacccaggg aactaggaag gcacttctgc ctgaggggca gcctgccttg    6540
cccactcctg ctctgctcgc ctcggatcag ctgagccttc tgagctggcc tctcactgcc    6600
tccccaaggc ccctgcctg ccctgtcagg aggcagaagg aagcaggtgt gagggcagtg    6660
caaggaggga gcacaacccc cagctcccgc tccgggctcc gacttgtgca caggcagagc    6720
ccagaccctg gaggaaatcc tacctttgaa ttcaagaaca tttggggaat ttggaaatct    6780
ctttgccccc aaaccccat tctgtcctac ctttaatcag gtcctgctca gcagtgagag    6840
cagatgaggt gaaaaggcca agaggtttgg ctcctgccca ctgatagccc ctctccccgc    6900
agtgtttgtg tgtcaagtgg caaagctgtt cttcctggtg accctgatta tatccagtaa    6960
cacatagact gtgcgcatag gcctgctttg tctcctctat cctgggcttt tgttttgctt    7020
```

```
tttagttttg cttttagttt ttctgtccct tttatttaac gcaccgacta gacacacaaa    7080
gcagttgaat ttttatatat atatctgtat attgcacaat tataaactca ttttgcttgt    7140
ggctccacac acacaaaaaa agacctgtta aaattatacc tgttgcttaa ttacaatatt    7200
tctgataacc atagcatagg acaagggaaa ataaaaaaag aaaaaaaaga aaaaaaaacg    7260
acaaatctgt ctgctggtca cttcttctgt ccaagcagat tcgtggtctt ttcctcgctt    7320
ctttcaaggg ctttcctgtg ccaggtgaag gaggctccag gcagcaccca ggttttgcac    7380
tcttgtttct cccgtgcttg tgaaagaggt cccaaggttc tgggtgcagg agcgctccct    7440
tgacctgctg aagtccggaa cgtagtcggc acagcctggt cgccttccac ctctgggagc    7500
tggagtccac tggggtggcc tgactccccc agtccccttc ccgtgacctg gtcagggtga    7560
gcccatgtgg agtcagcctc gcaggcctcc ctgccagtag ggtccgagtg tgtttcatcc    7620
ttcccactct gtcgagcctg ggggctggag cggagacggg aggcctggcc tgtctcggaa    7680
cctgtgagct gcaccaggta gaacgccagg gaccccagaa tcatgtgcgt cagtccaagg    7740
ggtcccctcc aggagtagtg aagactccag aaatgtccct ttcttctccc ccatcctacg    7800
agtaattgca tttgcttttg taattcttaa tgagcaatat ctgctagaga gtttagctgt    7860
aacagttctt tttgatcatc ttttttttaat aattagaaac accaaaaaaa tccagaaact    7920
tgttcttcca aagcagagag cattataatc accagggcca aaagcttccc tccctgctgt    7980
cattgcttct tctgaggcct gaatccaaaa gaaaacagc cataggccct ttcagtggcc    8040
gggctacccg tgagcccttc ggaggaccag ggctggggca gcctctgggc ccacatccgg    8100
ggccagctcc ggcgtgtgtt cagtgttagc agtgggtcat gatgctcttt cccacccagc    8160
ctgggatagg ggcagaggag gcgaggaggc cgttgccgct gatgtttggc cgtgaacagg    8220
tgggtgtctg cgtgcgtcca cgtgcgtgtt ttctgactga catgaaatcg acgcccgagt    8280
tagcctcacc cggtgacctc tagccctgcc cggatggagc ggggcccacc cggttcagtg    8340
tttctgggga gctggacagt ggagtgcaaa aggcttgcag aacttgaagc ctgctccttc    8400
ccttgctacc acggcctcct ttccgtttga tttgtcactg cttcaatcaa taacagccgc    8460
tccagagtca gtagtcaatg aatatatgac caaatatcac caggactgtt actcaatgtg    8520
tgccgagccc ttgcccatgc tgggctcccg tgtatctgga cactgtaacg tgtgctgtgt    8580
ttgctcccct tccccttcct tctttgccct ttacttgtct ttctggggtt tttctgtttg    8640
ggttttggttt ggttttatt tctccttttg tgttccaaac atgaggttct ctctactggt    8700
cctcttaact gtggtgttga ggcttatatt tgtgtaattt ttggtgggtg aaaggaattt    8760
tgctaagtaa atctcttctg tgtttgaact gaagtctgta ttgtaactat gtttaaagta    8820
attgttccag agacaaatat ttctagacac tttttcttta caaacaaaag cattcggagg    8880
gaggggatg gtgactgaga tgagagggga gagctgaaca gatgacccct gcccagatca    8940
gccagaagcc acccaaagca gtggagccca ggagtccac tccaagccag caagccgaat    9000
agctgatgtg ttgccacttt ccaagtcact gcaaaaccag gttttgttcc gcccagtgga    9060
ttcttgtttt gcttcccctc ccccgagat tattaccacc atcccgtgct tttaaggaaa    9120
ggcaagattg atgtttcctt gagggagcc aggaggggat gtgtgtgtgc agagctgaag    9180
agctggggag aatgggctg gcccaccca agcaggaggc tgggacgctc tgctgtgggc    9240
acaggtcagg ctaatgttgg cagatgcagc tcttcctgga caggccaggt ggtgggcatt    9300
ctctctccaa ggtgtgcccc gtgggcatta ctgtttaaga cacttccgtc acatcccacc    9360
ccatcctcca gggctcaaca ctgtgacatc tctattcccc accctcccct tcccagggca    9420
```

```
ataaaatgac catggagggg gcttgcactc tcttggctgt cacccgatcg ccagcaaaac    9480
ttagatgtga gaaaccccct tcccattcca tggcgaaaac atctccttag aaaagccatt    9540
accctcatta ggcatggttt tgggctccca aaacacctga cagcccctcc ctcctctgag    9600
aggcggagag tgctgactgt agtgaccatt gcatgccggg tgcagcatct ggaagagcta    9660
ggcagggtgt ctgccccctc ctgagttgaa gtcatgctcc cctgtgccag cccagaggcc    9720
gagagctatg gacagcattg ccagtaacac aggccaccct gtgcagaagg gagctggctc    9780
cagcctggaa acctgtctga ggttgggaga ggtgcacttg gggcacaggg agaggccggg    9840
acacacttag ctggagatgt ctctaaaagc cctgtatcgt attcaccttc agttttgtg    9900 ttttgggaca attactttag aaaataagta ggtcgtttta aaacaaaaa ttattgattg    9960 ctttttgta gtgttcagaa aaaggttct ttgtgtatag ccaaatgact gaaagcactg   10020
atatatttaa aaacaaaagg caatttatta aggaaatttg taccatttca gtaaacctgt   10080
ctgaatgtac ctgtatacgt ttcaaaaaca ccccccccc actgaatccc tgtaacctat   10140
ttattatata aagagtttgc cttataaatt t                                 10171

<210> SEQ ID NO 22
<211> LENGTH: 10113
<212> TYPE: DNA
<213> ORGANISM: Homo sapiens

<400> SEQUENCE: 22
gctccataaa aatacagact caccagttcc tgctttgatg tgacatgtga ctccccagaa      60
tacaccttgc ttctgtagac cagctccaac aggattccat ggtagctggg atgttagggc     120
tcagggaaga aaagtcagaa gaccaggacc tccagggcct caaggacaaa cccctcaagt     180
ttaaaaaggt gaagaaagat aagaaagaag agaaagaggg caagcatgag cccgtgcagc     240
catcagccca ccactctgct gagcccgcag aggcaggcaa agcagagaca tcagaagggt     300
caggctccgc cccggctgtg ccggaagctt ctgcctcccc caaacagcgg cgctccatca     360
tccgtgaccg ggacccatg tatgatgacc ccaccctgcc tgaaggctgg acacggaagc      420
ttaagcaaag gaaatctggc cgctctgctg ggaagtatga tgtgtatttg atcaatcccc     480
agggaaaagc ctttcgctct aaagtggagt tgattgcgta cttcgaaaag gtaggcgaca     540
catccctgga ccctaatgat tttgacttca cggtaactgg gagagggagc ccctcccggc     600
gagagcagaa accacctaag aagcccaaat ctcccaaagc tccaggaact ggcagaggcc     660
ggggacgccc caaagggagc ggcaccacga gacccaaggc ggccacgtca gagggtgtgc     720
aggtgaaaag ggtcctggag aaaagtcctg ggaagctcct tgtcaagatg ccttttcaaa     780
cttcgccagg gggcaaggct gaggggggtg gggccaccac atccacccag gtcatggtga     840
tcaaacgccc cggcaggaag cgaaaagctg aggccgaccc tcaggccatt cccaagaaac     900
ggggccgaaa gccggggagt gtggtggcag ccgctgccgc cgaggccaaa agaaagccg      960 tgaaggagtc ttctatccga tctgtgcagg agaccgtact cccatcaag aagcgcaaga    1020 cccgggagac ggtcagcatc gaggtcaagg aagtggtgaa gccctgctg gtgtccaccc    1080 tcggtgagaa gagcgggaaa ggactgaaga cctgtaagag ccctgggcgg aaaagcaagg    1140
agagcagccc caaggggcgc agcagcagcg cctcctcacc cccaagaag gagcaccacc    1200 accatcacca ccactcagag tccccaaagg ccccgtgcc actgctccca ccctgcccc     1260 cacctccacc tgagcccgag agctccgagg accccaccag ccccctgag ccccaggact    1320
```

```
tgagcagcag cgtctgcaaa gaggagaaga tgcccagagg aggctcactg gagagcgacg   1380
gctgccccaa ggagccagct aagactcagc ccgcggttgc caccgccgcc acggccgcag   1440
aaaagtacaa acaccgaggg gagggagagc gcaaagacat tgtttcatcc tccatgccaa   1500
ggccaaacag agaggagcct gtggacagcc ggacgcccgt gaccgagaga gttagctgac   1560
tttacacgga gcggattgca aagcaaacca acaagaataa aggcagctgt tgtctcttct   1620
ccttatgggt agggctctga caaagcttcc cgattaactg aaataaaaaa tattttttt    1680
tctttcagta aacttagagt ttcgtggctt cagggtggga gtagttggag cattgggat    1740
gttttttctta ccgacaagca cagtcaggtt gaagacctaa ccagggccag aagtagcttt   1800
gcacttttct aaactaggct ccttcaacaa ggcttgctgc agatactact gaccagacaa   1860
gctgttgacc aggcacctcc cctcccgccc aaacctttcc cccatgtggt cgttagagac   1920
agagcgacag agcagttgag aggacactcc cgttttcggt gccatcagtg cccgtctac    1980
agctccccca gctccccca cctcccccac tcccaaccac gttgggacag ggaggtgtga   2040
ggcaggagag acagttggat tctttagaga agatggatat gaccagtggc tatgcctgt    2100
gcgatcccac ccgtggtggc tcaagtctgg ccccacacca gccccaatcc aaaactggca   2160
aggacgcttc acaggacagg aaagtggcac ctgtctgctc cagctctggc atggctagga   2220
ggggggagtc ccttgaacta ctgggtgtag actggcctga accacaggag aggatggccc   2280
agggtgaggt ggcatggtcc attctcaagg gacgtcctcc aacgggtggc gctagaggcc   2340
atggaggcag taggacaagg tgcaggcagg ctggcctggg gtcaggccgg gcagagcaca   2400
gcggggtgag agggattcct aatcactcag agcagtctgt gacttagtgg acaggggagg   2460
gggcaaaggg ggaggagaag aaaatgttct tccagttact ttccaattct cctttaggga   2520
cagcttagaa ttatttgcac tattgagtct tcatgttccc acttcaaaac aaacagatgc   2580
tctgagagca aactggcttg aattggtgac atttagtccc tcaagccacc agatgtgaca   2640
gtgttgagaa ctacctggat ttgtatatat acctgcgctt gttttaaagt gggctcagca   2700
catagggttc ccacgaagct ccgaaactct aagtgtttgc tgcaattttta taaggacttc   2760
ctgattggtt tctcttctcc ccttccattt ctgccttttg ttcatttcat cctttcactt   2820
cttttccctct ctccgtcctc ctccttccta gttcatccct tctcttccag gcagccgcgg   2880
tgcccaacca cacttgtcgg ctccagtccc cagaactctg cctgcccttt gtcctcctgc   2940
tgccagtacc agccccaccc tgttttgagc cctgaggagg cctgggctc tgctgagtcc    3000
gacctggcct gtctgtgaag agcaagagag cagcaaggtc ttgctctcct aggtagcccc   3060
ctcttccctg gtaagaaaaa gcaaaaggca tttcccaccc tgaacaacga gccttttcac   3120
ccttctactc tagagaagtg gactggagga gctgggcccg atttggtagt tgaggaaagc   3180
acagaggcct cctgtggcct gccagtcatc gagtggccca acagggctc catgccagcc    3240
gaccttgacc tcactcagaa gtccagagtc tagcgtagtg cagcagggca gtagcggtac   3300
caatgcagaa ctcccaagac ccgagctggg accagtacct gggtccccag cccttcctct   3360
gctcccccttt ttccctcgga gttcttcttg aatggcaatg ttttgctttt gctcgatgca   3420
gacaggggc cagaacacca cacatttcac tgtctgtctg gtccatagct gtggtgtagg   3480
ggcttagagg catgggcttg ctgtgggttt ttaattgatc agttttcatg tgggatccca   3540
tctttttaac ctctgttcag gaagtcctta tctagctgca tatcttcatc atattggtat   3600
atcctttct gtgtttacag agatgtctct tatatctaaa tctgtccaac tgagaagtac    3660
cttatcaaag tagcaaatga gacagcagtc ttatgcttcc agaaacaccc acaggcatgt   3720
```

```
cccatgtgag ctgctgccat gaactgtcaa gtgtgtgttg tcttgtgtat ttcagttatt   3780
gtccctggct tccttactat ggtgtaatca tgaaggagtg aaacatcata gaaactgtct   3840
agcacttcct tgccagtctt tagtgatcag gaaccatagt tgacagttcc aatcagtagc   3900
ttaagaaaaa accgtgtttg tctcttctgg aatggttaga agtgagggag tttgccccgt   3960
tctgtttgta gagtctcata gttggacttt ctagcatata tgtgtccatt tccttatgct   4020
gtaaaagcaa gtcctgcaac caaactccca tcagcccaat ccctgatccc tgatcccttc   4080
cacctgctct gctgatgacc cccccagctt cacttctgac tcttccccag gaagggaagg   4140
ggggtcagaa gagagggtga gtcctccaga actcttcctc caaggacaga aggctcctgc   4200
ccccatagtg gcctcgaact cctggcacta ccaaaggaca cttatccacg agagcgcagc   4260
atccgaccag gttgtcactg agaagatgtt tattttggtc agttgggttt ttatgtatta   4320
tacttagtca aatgtaatgt ggcttctgga atcattgtcc agagctgctt ccccgtcacc   4380
tgggcgtcat ctggtcctgg taagaggagt gcgtggccca ccaggccccc ctgtcaccca   4440
tgacagttca ttcagggccg atggggcagt cgtggttggg aacacagcat ttcaagcgtc   4500
actttatttc attcgggccc cacctgcagc tccctcaaag aggcagttgc ccagcctctt   4560
tcccttccag tttattccag agctgccagt ggggcctgag gctccttagg gttttctctc   4620
tatttccccc tttcttcctc attccctcgt ctttcccaaa ggcatcacga gtcagtcgcc   4680
tttcagcagg cagccttggc ggtttatcgc cctggcaggc aggggccctg cagctctcat   4740 gctgccctg ccttgggtc aggttgacag gaggttggag ggaaagcctt aagctgcagg    4800
attctcacca gctgtgtccg gcccagtttt ggggtgtgac ctcaatttca attttgtctg   4860
tacttgaaca ttatgaagat gggggcctct ttcagtgaat ttgtgaacag cagaattgac   4920
cgacagcttt ccagtaccca tggggctagg tcattaaggc cacatccaca gtctccccca   4980
cccttgttcc agttgttagt tactacctcc tctcctgaca atactgtatg tcgtcgagct   5040 cccccccaggt ctaccctcc cggccctgcc tgctggtggg cttgtcatag ccagtgggat    5100
tgccggtctt gacagctcag tgagctggag atacttggtc acagccaggc gctagcacag   5160
ctcccttctg ttgatgctgt attcccatat caaaagacac aggggacacc cagaaacgcc   5220
acatccccca atccatcagt gccaaactag ccaacggccc cagcttctca gctcgctgga   5280
tggcggaagc tgctactcgt gagcgccagt gcgggtgcac acaatcttct gttgggtggc   5340
atcattccag gcccgaagca tgaacagtgc acctgggaca gggagcagcc ccaaattgtc   5400
acctgcttct ctgcccagct tttcattgct gtgacagtga tggcgaaaga gggtaataac   5460
cagacacaaa ctgccaagtt gggtggagaa aggagtttct ttagctgaca gaatctctga   5520
attttaaatc acttagtaag cggctcaagc ccaggaggga gcagagggat acgagcggag   5580
tcccctgcgc gggaccatct ggaattggtt tagcccaagt ggagcctgac agccagaact   5640
ctgtgtcccc cgtctaacca cagctccttt tccagagcat tccagtcagg ctctctgggc   5700
tgactgggcc aggggaggtt acaggtacca gttctttaag aagatctttg gcatataca    5760 tttttagcct gtgtcattgc cccaaatgga ttcctgtttc aagttcacac ctgcagattc   5820
taggacctgt gtcctagact tcagggagtc agctgttct agagttccta ccatggagtg    5880
ggtctggagg acctgcccgg tggggggca gagccctgct ccctccgggt cttcctactc    5940
ttctctctgc tctgacggga tttgttgatt ctctccattt tggtgtcttt ctcttttaga   6000
tattgtatca atctttagaa aaggcatagt ctacttgtta taaatcgtta ggatactgcc   6060
```

```
tcccccaggg tctaaaatta catattagag gggaaaagct gaacactgaa gtcagttctc    6120
aacaatttag aaggaaaacc tagaaaacat ttggcagaaa attacatttc gatgttttg    6180
aatgaatacg agcaagcttt tacaacagtg ctgatctaaa aatacttagc acttggcctg    6240
agatgcctgg tgagcattac aggcaagggg aatctggagg tagccgacct gaggacatgg    6300
cttctgaacc tgtcttttgg gagtggtatg aaggtggag cgttcaccag tgacctggaa     6360
ggcccagcac caccctcctt cccactcttc tcatcttgac agagcctgcc ccagcgctga    6420
cgtgtcagga aaacacccag ggaactagga aggcacttct gcctgagggg cagcctgcct    6480
tgcccactcc tgctctgctc gcctcggatc agctgagcct tctgagctgg cctctcactg    6540
cctcccaag gcccctgcc tgccctgtca ggaggcagaa ggaagcaggt gtgagggcag       6600
tgcaaggagg gagcacaacc cccagctccc gctccgggct ccgacttgtg cacaggcaga    6660
gcccagaccc tggaggaaat cctacctttg aattcaagaa catttgggga atttggaaat    6720
ctctttgccc ccaaacccc attcgtgtcct acctttaatc aggtcctgct cagcagtgag    6780
agcagatgag gtgaaaaggc caagaggttt ggctcctgcc cactgatagc ccctctcccc    6840
gcagtgtttg tgtgtcaagt ggcaaagctg ttcttcctgg tgaccctgat tatatccagt    6900
aacacataga ctgtgcgcat aggcctgctt tgtctcctct atcctgggct tttgttttgc    6960
tttttagttt tgcttttagt ttttctgtcc cttttattta acgcaccgac tagacacaca    7020
aagcagttga attttatat atatatctgt atattgcaca attataaact cattttgctt      7080
gtggctccac acacacaaaa aaagacctgt taaaattata cctgttgctt aattacaata    7140
tttctgataa ccatagcata ggacaaggga aaataaaaaa agaaaaaaaa gaaaaaaaa     7200
cgacaaatct gtctgctggt cacttcttct gtccaagcag attcgtggtc ttttcctcgc    7260
ttctttcaag ggctttcctg tgccaggtga aggaggctcc aggcagcacc caggttttgc    7320
actcttgttt ctcccgtgct tgtgaaagag gtcccaaggt tctgggtgca ggagcgctcc    7380
cttgacctgc tgaagtccgg aacgtagtcg gcacagcctg gtcgccttcc acctctggga    7440
gctggagtcc actggggtgg cctgactccc ccagtcccct tcccgtgacc tggtcagggt    7500
gagcccatgt ggagtcagcc tcgcaggcct ccctgccagt agggtccgag tgtgtttcat    7560
ccttcccact ctgtcgagcc tgggggctgg agcggagacg ggaggcctgg cctgtctcgg    7620
aacctgtgag ctgcaccagg tagaacgcca gggaccccag aatcatgtgc gtcagtccaa    7680
ggggtcccct ccaggagtag tgaagactcc agaaatgtcc ctttcttctc ccccatccta    7740
cgagtaattg catttgcttt tgtaattctt aatgagcaat atctgctaga gagtttagct    7800
gtaacagttc ttttttgatca tctttttta ataattagaa acaccaaaaa aatccagaaa     7860
cttgttcttc caaagcagag agcattataa tcaccagggc caaaagcttc cctccctgct    7920
gtcattgctt cttctgaggc ctgaatccaa aagaaaaaca gccataggcc ctttcagtgg    7980
ccgggctacc cgtgagccct tcggaggacc agggctgggg cagcctctgg gcccacatcc    8040
ggggccagct ccggcgtgtg ttcagtgtta gcagtgggtc atgatgctct ttcccaccca    8100
gcctgggata ggggcagagg aggcgaggag gccgttgccg ctgatgtttg gccgtgaaca    8160
ggtgggtgtc tgcgtgcgtc cacgtgcgtg ttttctgact gacatgaaat cgacgcccga    8220
gttagcctca cccggtgacc tctagccctg cccggatgga gcggggccca cccggttcag    8280
tgttctgggg gagctggaca gtggagtgca aaaggcttgc agaacttgaa gcctgctcct    8340
tcccttgcta ccacggcctc cttttccgttt gatttgtcac tgcttcaatc aataacagcc    8400
gctccagagt cagtagtcaa tgaatatatg accaaatatc accaggactg ttactcaatg    8460
```

```
tgtgccgagc ccttgcccat gctgggctcc cgtgtatctg gacactgtaa cgtgtgctgt    8520
gtttgctccc cttcccttc cttctttgcc ctttacttgt ctttctgggg tttttctgtt    8580
tgggtttggt ttggttttta tttctccttt tgtgttccaa acatgaggtt ctctctactg    8640
gtcctcttaa ctgtggtgtt gaggcttata tttgtgtaat ttttggtggg tgaaaggaat    8700
tttgctaagt aaatctcttc tgtgtttgaa ctgaagtctg tattgtaact atgtttaaag    8760
taattgttcc agagacaaat atttctagac acttttctt tacaaacaaa agcattcgga     8820
gggaggggga tggtgactga gatgagaggg gagagctgaa cagatgaccc ctgcccagat    8880
cagccagaag ccacccaaag cagtggagcc caggagtccc actccaagcc agcaagccga    8940
atagctgatg tgttgccact ttccaagtca ctgcaaaacc aggttttgtt ccgcccagtg    9000
gattcttgtt ttgcttcccc tcccccgag attattacca ccatcccgtg cttttaagga     9060
aaggcaagat tgatgtttcc ttgaggggag ccaggagggg atgtgtgtgt gcagagctga    9120
agagctgggg agaatggggc tgggcccacc caagcaggag ctgggacgc tctgctgtgg     9180 gcacaggtca ggctaatgtt ggcagatgca gctcttcctg gacaggccag gtggtgggca    9240
ttctctctcc aaggtgtgcc ccgtgggcat tactgtttaa gacacttccg tcacatccca    9300
ccccatcctc cagggctcaa cactgtgaca tctctattcc ccaccctccc cttcccaggg    9360
caataaaatg accatggagg gggcttgcac tctcttggct gtcacccgat cgccagcaaa    9420
acttagatgt gagaaaaccc cttcccattc catggcgaaa acatctcctt agaaaagcca    9480
ttaccctcat taggcatggt tttgggctcc caaaacacct gacagcccct ccctcctctg    9540
agaggcggag agtgctgact gtagtgacca ttgcatgccg ggtgcagcat ctggaagagc    9600
taggcagggt gtctgccccc tcctgagttg aagtcatgct cccctgtgcc agcccagagg    9660
ccgagagcta tggacagcat tgccagtaac acaggccacc ctgtgcagaa gggagctggc    9720
tccagcctgg aaacctgtct gaggttggga gaggtgcact tggggcacag ggagaggccg    9780
ggacacactt agctggagat gtctctaaaa gccctgtatc gtattcacct tcagttttg     9840 tgttttggga caattacttt agaaaataag taggtcgttt taaaaacaaa aattattgat    9900
tgcttttttg tagtgttcag aaaaaaggtt ctttgtgtat agccaaatga ctgaaagcac    9960
tgatatattt aaaaacaaaa ggcaatttat taaggaaatt tgtaccattt cagtaaacct   10020
gtctgaatgt acctgtatac gtttcaaaaa caccccccccc ccactgaatc cctgtaacct   10080
atttattata taaagagttt gccttataaa ttt                                10113
```

<210> SEQ ID NO 23
<211> LENGTH: 10182
<212> TYPE: DNA
<213> ORGANISM: Homo sapiens

<400> SEQUENCE: 23

```
ccggaaattg gccgccgccg ccgccgccgc gccgagcgga ggaggaggag gaggcgagga      60
ggagagactg ctccataaaa atacagactc accagttcct gctttgatgt gacatgtgac    120
tccccagaat acaccttgct tctgtagacc agctccaaca ggattccatg gtagctggga    180
tgttagggct cagggaagaa aagtcagaag accaggacct ccaggcctc aaggacaaac     240 ccctcaagtt taaaaaggtg aagaaagata agaaagaaga gaaagagggc aagcatgagc    300
ccgtgcagcc atcagcccac cactctgctg agcccgcaga ggcaggcaaa gcagagacat    360
cagaagggtc aggctccgcc ccggctgtgc cggaagcttc tgcctccccc aaacagcggc    420
```

```
gctccatcat ccgtgaccgg ggacccatgt atgatgaccc caccctgcct gaaggctgga    480
cacggaagct taagcaaagg aaatctggcc gctctgctgg aagtatgat gtgtatttga     540 tcaatcccca gggaaaagcc tttcgctcta aagtggagtt gattgcgtac ttcgaaaagg    600
taggcgacac atccctggac cctaatgatt ttgacttcac ggtaactggg agagggagcc    660
cctcccggcg agagcagaaa ccacctaaga agcccaaatc tcccaaagct ccaggaactg    720
gcagaggccg gggacgcccc aaagggagcg caccacgag acccaaggcg ccacgtcag      780 agggtgtgca ggtgaaaagg gtcctggaga aaagtcctgg gaagctcctt gtcaagatgc    840
cttttcaaac ttcgccaggg ggcaaggctg aggggggtgg ggccaccaca tccacccagg    900
tcatggtgat caaacgcccc ggcaggaagc gaaaagctga ggccgaccct caggccattc    960
ccaagaaacg gggccgaaag ccggggagtg tggtggcagc cgctgccgcc gaggccaaaa    1020
agaaagccgt gaaggagtct tctatccgat ctgtgcagga gaccgtactc cccatcaaga    1080
agcgcaagac ccgggagacg gtcagcatcg aggtcaagga agtggtgaag cccctgctgg    1140
tgtccaccct cggtgagaag agcggaaaag gactgaagac ctgtaagagc cctgggcgga    1200
aaagcaagga gagcagcccc aaggggcgca gcagcagcgc ctcctcaccc cccaagaagg    1260
agcaccacca ccatcaccac cactcagagt ccccaaaggc ccccgtgcca ctgctcccac    1320
ccctgccccc acctccacct gagcccgaga gctccgagga ccccaccagc cccctgagc    1380 cccaggactt gagcagcagc gtctgcaaag aggagaagat gccagagga ggctcactgg    1440 agagcgacgg ctgccccaag gagccagcta agactcagcc cgcggttgcc accgccgcca    1500
cggccgcaga aaagtacaaa caccgagggg agggagagcg caaagacatt gtttcatcct    1560
ccatgccaag gccaaacaga gaggagcctg tggacagccg gacgcccgtg accgagagag    1620
ttagctgact ttacacggag cggattgcaa agcaaaccaa caagaataaa ggcagctgtt    1680
gtctcttctc cttatgggta gggctctgac aaagcttccc gattaactga aataaaaaat    1740
attttttttt ctttcagtaa acttagagtt tcgtggcttc agggtgggag tagttggagc    1800
attggggatg ttttttcttac cgacaagcac agtcaggttg aagacctaac cagggccaga    1860
agtagctttg cacttttcta aactaggctc cttcaacaag gcttgctgca gatactactg    1920
accagacaag ctgttgacca ggcacctccc ctcccgccca aaccttttccc ccatgtggtc    1980 gttagagaca gagcgacaga gcagttgaga ggacactccc gttttcggtg ccatcagtgc    2040
cccgtctaca gctcccccag ctcccccac ctcccccact cccaaccacg ttgggacagg     2100
gaggtgtgag gcaggagaga cagttggatt ctttagagaa gatggatatg accagtggct    2160
atggcctgtg cgatcccacc cgtggtggct caagtctggc cccacaccag ccccaatcca    2220
aaactggcaa ggacgcttca caggacagga aagtggcacc tgtctgctcc agctctggca    2280
tggctaggag gggggagtcc cttgaactac tgggtgtaga ctggcctgaa ccacaggaga    2340
ggatggccca gggtgaggtg gcatggtcca ttctcaaggg acgtcctcca acgggtggcg    2400
ctagaggcca tggaggcagt aggacaaggt gcaggcaggc tggcctgggg tcaggccggg    2460
cagagcacag cggggtgaga gggattccta atcactcaga gcagtctgtg acttagtgga    2520
caggggaggg ggcaaagggg gaggagaaga aaatgttctt ccagttactt tccaattctc    2580
ctttagggac agcttagaat tatttgcact attgagtctt catgttccca cttcaaaaca    2640
aacagatgct ctgagagcaa actggcttga attggtgaca tttagtccct caagccacca    2700 gatgtgcacag tgttgagaac tacctggatt tgtatatata cctgcgcttg ttttaaagtg    2760
ggctcagcac atagggttcc cacgaagctc cgaaactcta agtgtttgct gcaatttat     2820
```

```
aaggacttcc tgattggttt ctcttctccc cttccatttc tgccttttgt tcatttcatc    2880
ctttcacttc tttcccttcc tccgtcctcc tccttcctag ttcatcccttt ctcttccagg   2940 cagccgcggt gcccaaccac acttgtcggc tccagtcccc agaactctgc ctgcccttg     3000 tcctcctgct gccagtacca gccccaccct gttttgagcc ctgaggaggc cttgggctct    3060
gctgagtccg acctggcctg tctgtgaaga gcaagagagc agcaaggtct tgctctccta   3120
ggtagccccc tcttccctgg taagaaaaag caaaaggcat ttcccaccct gaacaacgag   3180
ccttttcacc cttctactct agagaagtgg actggaggag ctgggcccga tttggtagtt   3240
gaggaaagca cagaggcctc ctgtggcctg ccagtcatcg agtggcccaa caggggctcc   3300
atgccagccg accttgacct cactcagaag tccagagtct agcgtagtgc agcagggcag   3360
tagcggtacc aatgcagaac tcccaagacc cgagctggga ccagtacctg ggtccccagc   3420
ccttcctctg ctcccccttt tccctcggag ttcttcttga atggcaatgt tttgcttttg   3480
ctcgatgcag acaggggggcc agaacaccac acatttcact gtctgtctgg tccatagctg   3540
tggtgtaggg gcttagaggc atgggcttgc tgtgggtttt taattgatca gttttcatgt   3600
gggatcccat cttttttaacc tctgttcagg aagtccttat ctagctgcat atcttcatca   3660
tattggtata tccttttctg tgtttacaga gatgtctctt atatctaaat ctgtccaact   3720
gagaagtacc ttatcaaagt agcaaatgag acagcagtct tatgcttcca gaaacaccca   3780
caggcatgtc ccatgtgagc tgctgccatg aactgtcaag tgtgtgttgt cttgtgtatt   3840
tcagttattg tccctggctt ccttactatg gtgtaatcat gaaggagtga acatcatag   3900 aaactgtcta gcacttcctt gccagtcttt agtgatcagg aaccatagtt gacagttcca   3960
atcagtagct taagaaaaaa ccgtgtttgt ctcttctgga atggttagaa gtgagggagt   4020
ttgccccgtt ctgtttgtag agtctcatag ttggacttc tagcatatat gtgtccattt     4080
ccttatgctg taaaagcaag tcctgcaacc aaactcccat cagcccaatc cctgatccct   4140
gatcccttcc acctgctctg ctgatgaccc ccccagcttc acttctgact cttccccagg    4200
aagggaaggg gggtcagaag agagggtgag tcctccagaa ctcttcctcc aaggacagaa   4260
ggctcctgcc cccatagtgg cctcgaactc ctggcactac caaaggacac ttatccacga    4320
gagcgcagca tccgaccagg ttgtcactga gaagatgttt attttggtca gttgggtttt   4380
tatgtattat acttagtcaa atgtaatgtg gcttctggaa tcattgtcca gagctgcttc    4440
cccgtcacct gggcgtcatc tggtcctggt aagaggagtg cgtggcccac caggcccccc   4500
tgtcacccat gacagttcat tcaggccga tggggcagtc gtggttggga acacagcatt    4560
tcaagcgtca ctttatttca ttcgggcccc acctgcagct ccctcaaaga ggcagttgcc   4620
cagcctcttt cccttccagt ttattccaga gctgccagtg gggcctgagg ctccttaggg   4680
ttttctctct atttcccct ttcttcctca ttccctcgtc tttcccaaag gcatcacgag      4740
tcagtcgcct ttcagcaggc agccttggcg gtttatcgcc ctggcaggca ggggccctgc    4800
agctctcatg ctgcccctgc cttggggtca ggttgacagg aggttggagg gaaagcctta   4860
agctgcagga ttctcaccag ctgtgtccgg cccagttttg gggtgtgacc tcaatttcaa   4920
ttttgtctgt acttgaacat tatgaagatg ggggcctctt tcagtgaatt tgtgaacagc    4980
agaattgacc gacagctttc cagtacccat ggggctaggt cattaaggcc acatccacag    5040
tctcccccac ccttgttcca gttgttagtt actacctcct ctcctgacaa tactgtatgt   5100
cgtcgagctc ccccaggtc taccccctccc ggccctgcct gctggtgggc ttgtcatagc    5160
```

| | |
|---|---|
| cagtgggatt gccggtcttg acagctcagt gagctggaga tacttggtca cagccaggcg | 5220 |
| ctagcacagc tcccttctgt tgatgctgta ttcccatatc aaaagacaca ggggacaccc | 5280 |
| agaaacgcca catcccccaa tccatcagtg ccaaactagc caacggcccc agcttctcag | 5340 |
| ctcgctggat ggcggaagct gctactcgtg agcgccagtg cgggtgcaga caatcttctg | 5400 |
| ttgggtggca tcattccagg cccgaagcat gaacagtgca cctgggacag ggagcagccc | 5460 |
| caaattgtca cctgcttctc tgcccagctt ttcattgctg tgacagtgat ggcgaaagag | 5520 |
| ggtaataacc agacacaaac tgccaagttg ggtggagaaa ggagtttctt tagctgacag | 5580 |
| aatctctgaa tttaaatca cttagtaagc ggctcaagcc caggagggag cagagggata | 5640 |
| cgagcggagt cccctgcgcg ggaccatctg gaattggttt agcccaagtg gagcctgaca | 5700 |
| gccagaactc tgtgtccccc gtctaaccac agctccttt ccagagcatt ccagtcaggc | 5760 |
| tctctgggct gactgggcca ggggaggtta caggtaccag ttctttaaga agatctttgg | 5820 |
| gcatatacat ttttagcctg tgtcattgcc ccaaatggat tcctgtttca agttcacacc | 5880 |
| tgcagattct aggacctgtg tcctagactt cagggagtca gctgtttcta gagttcctac | 5940 |
| catggagtgg gtctggagga cctgcccggt ggggggcag agccctgctc cctccgggtc | 6000 |
| ttcctactct tctctctgct ctgacgggat tgttgattc tctccatttt ggtgtctttc | 6060 |
| tcttttagat attgtatcaa tctttagaaa aggcatagtc tacttgttat aaatcgttag | 6120 |
| gatactgcct cccccagggt ctaaaattac atattgagg ggaaaagctg aacactgaag | 6180 |
| tcagttctca acaatttaga aggaaaacct agaaacatt tggcagaaaa ttacatttcg | 6240 |
| atgttttga atgaatacga gcaagctttt acaacagtgc tgatctaaaa atacttagca | 6300 |
| cttggcctga gatgcctggt gagcattaca ggcaagggga atctggaggt agccgacctg | 6360 |
| aggacatggc ttctgaacct gtcttttggg agtggtatgg aaggtggagc gttcaccagt | 6420 |
| gacctggaag gcccagcacc accctccttc ccactcttct catcttgaca gagcctgccc | 6480 |
| cagcgctgac gtgtcaggaa aacacccagg gaactaggaa ggcacttctg cctgaggggc | 6540 |
| agcctgcctt gcccactcct gctctgctcg cctcggatca gctgagcctt ctgagctggc | 6600 |
| ctctcactgc ctccccaagg ccccctgcct gccctgtcag gaggcagaag gaagcaggtg | 6660 |
| tgagggcagt gcaaggaggg agcacaaccc ccagctcccg ctccgggctc cgacttgtgc | 6720 |
| acaggcagag cccagaccct ggaggaaatc ctacctttga attcaagaac atttggggaa | 6780 |
| tttggaaatc tctttgcccc caaaccccca ttctgtccta cctttaatca ggtcctgctc | 6840 |
| agcagtgaga gcagatgagg tgaaaaggcc aagaggtttg gctcctgccc actgatagcc | 6900 |
| cctctccccg cagtgtttgt gtgtcaagtg gcaaagctgt tcttcctggt gaccctgatt | 6960 |
| atatccagta acacatagac tgtgcgcata ggcctgcttt gtctcctcta tcctgggctt | 7020 |
| ttgttttgct ttttagtttt gctttagtt tttctgtccc tttatttaa cgcaccgact | 7080 |
| agacacacaa agcagttgaa tttttatata tatatctgta tattgcacaa ttataaactc | 7140 |
| attttgcttg tggctccaca cacacaaaaa aagacctgtt aaaattatac ctgttgctta | 7200 |
| attacaatat ttctgataac catagcatag gacaagggaa aataaaaaaa gaaaaaaaag | 7260 |
| aaaaaaaaac gacaaatctg tctgctggtc acttcttctg tccaagcaga ttcgtggtct | 7320 |
| tttcctcgct tctttcaagg gctttcctgt gccaggtgaa ggaggctcca ggcagcaccc | 7380 |
| aggttttgca ctcttgtttc tcccgtgctt gtgaaagagg tcccaaggtt ctgggtgcag | 7440 |
| gagcgctccc ttgacctgct gaagtccgga acgtagtcgg cacagcctgg tcgccttcca | 7500 |
| cctctgggag ctggagtcca ctggggtggc ctgactcccc cagtccccctt cccgtgacct | 7560 |

```
ggtcagggtg agcccatgtg gagtcagcct cgcaggcctc cctgccagta gggtccgagt    7620
gtgtttcatc cttcccactc tgtcgagcct gggggctgga gcggagacgg gaggcctggc    7680
ctgtctcgga acctgtgagc tgcaccaggt agaacgccag ggaccccaga atcatgtgcg    7740
tcagtccaag gggtcccctc caggagtagt gaagactcca gaaatgtccc tttcttctcc    7800
cccatcctac gagtaattgc atttgctttt gtaattctta atgagcaata tctgctagag    7860
agtttagctg taacagttct ttttgatcat cttttttaa taattagaaa caccaaaaaa    7920
atccagaaac ttgttcttcc aaagcagaga gcattataat caccagggcc aaaagcttcc    7980
ctccctgctg tcattgcttc ttctgaggcc tgaatccaaa agaaaaacag cataggccc    8040 tttcagtggc cgggctaccc gtgagccctt cggaggacca gggctggggc agcctctggg    8100
cccacatccg gggccagctc cggcgtgtgt tcagtgttag cagtgggtca tgatgctctt    8160
tcccacccag cctgggatag gggcagagga ggcgaggagg ccgttgccgc tgatgtttgg    8220
ccgtgaacag gtgggtgtct gcgtgcgtcc acgtgcgtgt tttctgactg acatgaaatc    8280
gacgcccgag ttagcctcac ccggtgacct ctagccctgc ccggatggag cggggcccac    8340
ccggttcagt gtttctgggg agctggacag tggagtgcaa aaggcttgca gaacttgaag    8400
cctgctcctt cccttgctac cacggcctcc tttccgtttg atttgtcact gcttcaatca    8460
ataacagccg ctccagagtc agtagtcaat gaatatatga ccaaatatca ccaggactgt    8520
tactcaatgt gtgccgagcc cttgcccatg ctgggctccc gtgtatctgg acactgtaac    8580
gtgtgctgtg tttgctcccc ttcccctccc tctttgccc tttacttgtc tttctggggt    8640
ttttctgttt gggtttggtt tggttttat ttctccttt gtgttccaaa catgaggttc    8700
tctctactgg tcctcttaac tgtggtgttg aggcttatat ttgtgtaatt tttggtgggt    8760
gaaaggaatt ttgctaagta aatctcttct gtgtttgaac tgaagtctgt attgtaacta    8820
tgtttaaagt aattgttcca gagacaaata tttctagaca cttttctctt acaaacaaaa    8880
gcattcggag ggagggggat ggtgactgag atgagagggg agagctgaac agatgacccc    8940
tgcccagatc agccagaagc cacccaaagc agtggagccc aggagtccca ctccaagcca    9000
gcaagccgaa tagctgatgt gttgccactt tccaagtcac tgcaaaacca ggttttgttc    9060
cgcccagtgg attcttgttt tgcttccct ccccccgaga ttattaccac catcccgtgc    9120
ttttaaggaa aggcaagatt gatgtttcct tgaggggagc caggagggga tgtgtgtgtg    9180
cagagctgaa gagctgggga gaatgggggct gggcccaccc aagcaggagg ctgggacgct    9240
ctgctgtggg cacaggtcag gctaatgttg gcagatgcag ctcttcctgg acaggccagg    9300
tggtgggcat tctctctcca aggtgtgccc cgtgggcatt actgtttaag acacttccgt    9360
cacatcccac cccatcctcc agggctcaac actgtgacat ctctattccc cacccctccc    9420
ttcccagggc aataaaatga ccatggaggg ggcttgcact ctcttggctg tcacccgatc    9480
gccagcaaaa cttagatgtg agaaaacccc ttcccattcc atggcgaaaa catctcctta    9540
gaaaagccat taccctcatt aggcatggtt ttgggctccc aaaacacctg acagcccctc    9600
cctcctctga gaggcggaga gtgctgactg tagtgaccat tgcatgccgg gtgcagcatc    9660
tggaagagct aggcagggtg tctgcccct cctgagttga agtcatgctc ccctgtgcca    9720
gcccagaggc cgagagctat ggacagcatt gccagtaaca caggccaccc tgtgcagaag    9780
ggagctggct ccagcctgga aacctgtctg aggttgggag aggtgcactt ggggcacagg    9840
gagaggccgg gacacactta gctggagatg tctctaaaag ccctgtatcg tattcacctt    9900
```

| | |
|---|---|
| cagttttttgt gttttgggac aattacttta gaaataagt aggtcgtttt aaaaacaaaa | 9960 |
| attattgatt gctttttgt agtgttcaga aaaaaggttc tttgtgtata gccaaatgac | 10020 |
| tgaaagcact gatatattta aaaacaaaag gcaatttatt aaggaaattt gtaccatttc | 10080 |
| agtaaacctg tctgaatgta cctgtatacg tttcaaaaac accccccccc cactgaatcc | 10140 |
| ctgtaaccta tttattatat aaagagtttg ccttataaat tt | 10182 |

<210> SEQ ID NO 24
<211> LENGTH: 10180
<212> TYPE: DNA
<213> ORGANISM: Homo sapiens

<400> SEQUENCE: 24

| | |
|---|---|
| ccggaaaatg gccgccgccg ccgccgccgc gccgagcgga ggaggaggag gaggcgagga | 60 |
| ggagagacct ccataaaaat acagactcac cagttcctgc tttgatgtga catgtgactc | 120 |
| cccagaatac accttgcttc tgtagaccag ctccaacagg attccatggt agctgggatg | 180 |
| ttagggctca gggaagaaaa gtcagaagac caggacctcc agggcctcaa ggacaaaccc | 240 |
| ctcaagttta aaaaggtgaa gaaagataag aaagaagaga aagagggcaa gcatgagccc | 300 |
| gtgcagccat cagcccacca ctctgctgag cccgcagagg caggcaaagc agagacatca | 360 |
| gaagggtcag gctccgcccc ggctgtgccg gaagcttctg cctcccccaa acagcggcgc | 420 |
| tccatcatcc gtgaccgggg acccatgtat gatgacccca ccctgcctga aggctggaca | 480 |
| cggaagctta agcaaaggaa atctggccgc tctgctggga agtatgatgt gtatttgatc | 540 |
| aatccccagg gaaaagcctt tcgctctaaa gtggagttga ttgcgtactt cgaaaaggta | 600 |
| ggcgacacat ccctggaccc taatgatttt gacttcacgg taactgggag agggagcccc | 660 |
| tcccggcgag agcagaaacc acctaagaag cccaaatctc ccaaagctcc aggaactggc | 720 |
| agaggccggg gacgccccaa agggagcggc accacgagac ccaaggcggc cacgtcagag | 780 |
| ggtgtgcagg tgaaaagggt cctggagaaa agtcctggga agctccttgt caagatgcct | 840 |
| tttcaaactt cgccaggggg caaggctgag gggggtgggg ccaccacatc cacccaggtc | 900 |
| atggtgatca acgccccgg caggaagcga aaagctgagg ccgaccctca ggccattccc | 960 |
| aagaaacggg gccgaaagcc ggggagtgtg gtggcagccg ctgccgccga ggccaaaaag | 1020 |
| aaagccgtga aggagtcttc tatccgatct gtgcaggaga ccgtactccc catcaagaag | 1080 |
| cgcaagaccc gggagacggt cagcatcgag gtcaaggaag tggtgaagcc cctgctggtg | 1140 |
| tccacccctcg gtgagaagag cgggaaagga ctgaagacct gtaagagccc tgggcggaaa | 1200 |
| agcaaggaga gcagccccaa ggggcgcagc agcagcgcct cctcaccccc caagaaggag | 1260 |
| caccaccacc atcaccacca ctcagagtcc ccaaaggccc ccgtgccact gctcccaccc | 1320 |
| ctgccccccac ctcaccctga gcccgagagc tccgaggacc ccaccagccc cctgagccc | 1380 |
| caggacttga gcagcagcgt ctgcaaagag gagaagatgc ccagaggagg ctcactggag | 1440 |
| agcgacggct gccccaagga gccagctaag actcagcccg cggttgccac cgccgccacg | 1500 |
| gccgcagaaa agtacaaaca ccgaggggag ggagagcgca agacattgt ttcatcctcc | 1560 |
| atgccaaggc caaacagaga ggagcctgtg gacagccgga cgcccgtgac cgagagagtt | 1620 |
| agctgacttt acacggagcg gattgcaaag caaaccaaca agaataaagg cagctgttgt | 1680 |
| ctcttctcct tatgggtagg gctctgacaa agcttcccga ttaactgaaa taaaaaatat | 1740 |
| tttttttct ttcagtaaac ttagagtttc gtggcttcag ggtggagta gttggagcat | 1800 |
| tggggatgtt tttcttaccg acaagcacag tcaggttgaa gacctaacca gggccagaag | 1860 |

```
tagctttgca cttttctaaa ctaggctcct tcaacaaggc ttgctgcaga tactactgac    1920
cagacaagct gttgaccagg cacctcccct cccgcccaaa cctttccccc atgtggtcgt    1980
tagagacaga gcgacagagc agttgagagg acactcccgt tttcggtgcc atcagtgccc    2040
cgtctacagc tcccccagct cccccacct ccccactcc caaccacgtt gggacaggga    2100
ggtgtgaggc aggagagaca gttggattct ttagagaaga tggatatgac cagtggctat    2160
ggcctgtgcg atcccacccg tggtggctca agtctggccc cacaccagcc ccaatccaaa    2220
actggcaagg acgcttcaca ggacaggaaa gtggcacctg tctgctccag ctctggcatg    2280
gctaggaggg gggagtccct tgaactactg ggtgtagact ggcctgaacc acaggagagg    2340
atggcccagg gtgaggtggc atggtccatt ctcaagggac gtcctccaac gggtggcgct    2400
agaggccatg gaggcagtag acaaggtgc aggcaggctg gcctggggtc aggccgggca    2460
gagcacagcg gggtgagagg gattcctaat cactcagagc agtctgtgac ttagtggaca    2520 ggggagggg caaggggga ggagaagaaa atgttcttcc agttactttc caattctcct    2580
ttagggacag cttagaatta tttgcactat tgagtcttca tgttcccact tcaaaacaaa    2640
cagatgctct gagagcaaac tggcttgaat tggtgacatt tagtccctca agccaccaga    2700
tgtgacagtg ttgagaacta cctggatttg tatatatacc tgcgcttgtt ttaaagtggg    2760
ctcagcacat agggttccca cgaagctccg aaactctaag tgtttgctgc aattttataa    2820
ggacttcctg attggtttct cttctcccct tccatttctg cctttgtgtc atttcatcct    2880
ttcacttctt tcccttcctc cgtcctcctc cttcctagtt catcccttct cttccaggca    2940
gccgcggtgc ccaaccacac ttgtcggctc cagtccccag aactctgcct gccctttgtc    3000
ctcctgctgc cagtaccagc cccaccctgt tttgagccct gaggaggcct tgggctctgc    3060
tgagtccgac ctggcctgtc tgtgaagagc aagagagcag caaggtcttg ctctcctagg    3120
tagccccctc ttccctggta agaaaaagca aaggcatt cccaccctga caacgagcc    3180 ttttcacct tctactctag agaagtggac tggaggagct gggcccgatt tggtagttga    3240
ggaaagcaca gaggcctcct gtggcctgcc agtcatcgag tggcccaaca ggggctccat    3300
gccagccgac cttgacctca ctcagaagtc cagagtctag cgtagtgcag cagggcagta    3360
gcggtaccaa tgcagaactc ccaagacccg agctgggacc agtacctggg tccccagccc    3420
ttcctctgct ccccctttc cctcggagtt cttcttgaat ggcaatgttt tgcttttgct    3480
cgatgcagac agggggccag aacaccacac atttcactgt ctgtctggtc catagctgtg    3540 gtgtagggc ttagaggcat gggcttgctg tgggttttta attgatcagt ttcatgtgg    3600 gatcccatct ttttaacctc tgttcaggaa gtccttatct agctgcatat cttcatcata    3660
ttggtatatc cttttctgtg tttacagaga tgtctcttat atctaaatct gtccaactga    3720
gaagtacctt atcaaagtag caaatgagac agcagtctta tgcttccaga aacacccaca    3780
ggcatgtccc atgtgagctg ctgccatgaa ctgtcaagtg tgtgttgtct tgtgtatttc    3840
agttattgtc cctggcttcc ttactatggt gtaatcatga aggagtgaaa catcatagaa    3900
actgtctagc acttccttgc cagtctttag tgatcaggaa ccatagttga cagttccaat    3960
cagtagctta agaaaaaacc gtgtttgtct cttctggaat ggttagaagt gagggagttt    4020
gccccgttct gtttgtagag tctcatagtt ggactttcta gcatatatgt gtccatttcc    4080
ttatgctgta aaagcaagtc ctgcaaccaa actcccatca gcccaatccc tgatccctga    4140
tcccttccac ctgctctgct gatgaccccc ccagcttcac ttctgactct tccccaggaa    4200
```

```
gggaaggggg gtcagaagag agggtgagtc ctccagaact cttcctccaa ggacagaagg    4260
ctcctgcccc catagtggcc tcgaactcct ggcactacca aaggacactt atccacgaga    4320
gcgcagcatc cgaccaggtt gtcactgaga agatgtttat tttggtcagt tgggttttta    4380
tgtattatac ttagtcaaat gtaatgtggc ttctggaatc attgtccaga gctgcttccc    4440
cgtcacctgg gcgtcatctg gtcctggtaa gaggagtgcg tggcccacca ggcccccctg    4500
tcacccatga cagttcattc agggccgatg gggcagtcgt ggttgggaac acagcatttc    4560
aagcgtcact ttatttcatt cgggccccac ctgcagctcc ctcaaagagg cagttgccca    4620 gcctcttttcc cttccagttt attccagagc tgccagtggg gcctgaggct ccttagggtt    4680
ttctctctat ttcccccttt cttcctcatt ccctcgtctt tcccaaaggc atcacgagtc    4740
agtcgccttt cagcaggcag ccttggcggt ttatcgccct ggcaggcagg ggccctgcag    4800
ctctcatgct gccccctgcct tggggtcagg ttgacaggag gttggaggga aagccttaag    4860
ctgcaggatt ctcaccagct gtgtccggcc cagttttggg gtgtgacctc aatttcaatt    4920
ttgtctgtac ttgaacatta tgaagatggg ggcctctttc agtgaatttg tgaacagcag    4980
aattgaccga cagcttttcca gtacccatgg ggctaggtca ttaaggccac atccacagtc    5040 tccccccaccc ttgttccagt tgttagttac tacctcctct cctgacaata ctgtatgtcg    5100
tcgagctccc cccaggtcta cccctcccgg ccctgcctgc tggtgggctt gtcatagcca    5160
gtgggattgc cggtcttgac agctcagtga gctggagata cttggtcaca gccaggcgct    5220
agcacagctc ccttctgttg atgctgtatt cccatatcaa agacacagg ggacacccag    5280 aaacgccaca tccccaatc catcagtgcc aaactagcca acggcccag cttctcagct    5340 cgctggatgg cggaagctgc tactcgtgag cgccagtgcg ggtgcagaca atcttctgtt    5400
gggtggcatc attccaggcc cgaagcatga acagtgcacc tgggacaggg agcagcccca    5460
aattgtcacc tgcttctctg cccagctttt cattgctgtg acagtgatgg cgaaagaggg    5520
taataaccag acacaaactg ccaagttggg tggagaaagg agtttcttta gctgacagaa    5580
tctctgaatt ttaaatcact tagtaagcgg ctcaagccca ggagggagca gagggatacg    5640
agcggagtcc cctgcgcggg accatctgga attggtttag cccaagtgga gcctgacagc    5700
cagaactctg tgtccccgt ctaaccacag ctccttttcc agagcattcc agtcaggctc    5760
tctgggctga ctgggccagg ggaggttaca ggtaccagtt cttaagaag atctttgggc    5820 atatacattt ttagcctgtg tcattgcccc aaatggattc ctgtttcaag ttcacacctg    5880
cagattctag gacctgtgtc ctagacttca gggagtcagc tgtttctaga gttcctacca    5940
tggagtgggt ctggaggacc tgcccggtgg gggggcagag ccctgctccc tccgggtctt    6000
cctactcttc tctctgctct gacgggattt gttgattctc tccatttggg tgtctttctc    6060
ttttagatat tgtatcaatc tttagaaaag gcatagtcta cttgttataa atcgttagga    6120
tactgcctcc cccagggtct aaaattacat attagagggg aaaagctgaa cactgaagtc    6180
agttctcaac aatttagaag gaaaacctag aaaacatttg gcagaaaatt acatttcgat    6240 gttttttgaat gaatacgagc aagcttttac aacagtgctg atctaaaaat acttagcact    6300
tggcctgaga tgcctggtga gcattacagg caagggggaat ctggaggtag ccgacctgag    6360
gacatggctt ctgaacctgt cttttgggag tggtatggaa ggtggagcgt tcaccagtga    6420
cctggaaggc ccagcaccac cctccttccc actcttctca tcttgacaga gcctgcccca    6480
gcgctgacgt gtcaggaaaa cacccaggga actaggaagg cacttctgcc tgaggggcag    6540
cctgccttgc ccactcctgc tctgctcgcc tcggatcagc tgagccttct gagctggcct    6600
```

```
ctcactgcct ccccaaggcc ccctgcctgc cctgtcagga ggcagaagga agcaggtgtg    6660
agggcagtgc aaggagggag cacaacccc agctcccgct ccgggctccg acttgtgcac     6720
aggcagagcc cagaccctgg aggaaatcct acctttgaat tcaagaacat ttggggaatt    6780
tggaaatctc tttgccccca aacccccatt ctgtcctacc tttaatcagg tcctgctcag    6840
cagtgagagc agatgaggtg aaaaggccaa gaggtttggc tcctgcccac tgatagcccc    6900
tctccccgca gtgtttgtgt gtcaagtggc aaagctgttc ttcctggtga ccctgattat    6960
atccagtaac acatagactg tgcgcatagg cctgctttgt ctcctctatc ctgggctttt    7020
gttttgcttt ttagttttgc ttttagtttt tctgtcccctt ttatttaacg caccgactag    7080
acacacaaag cagttgaatt tttatatata tatctgtata ttgcacaatt ataaactcat    7140
tttgcttgtg gctccacaca cacaaaaaaa gacctgttaa aattataacct gttgcttaat   7200 tacaatattt ctgataacca tagcatagga caagggaaaa taaaaaaaga aaaaaaagaa    7260
aaaaaaacga caaatctgtc tgctggtcac ttcttctgtc caagcagatt cgtggtcttt    7320
tcctcgcttc tttcaagggc tttcctgtgc caggtgaagg aggctccagg cagcacccag    7380
gttttgcact cttgttttctc ccgtgcttgt gaaagaggtc ccaaggttct gggtgcagga    7440
gcgctccctt gacctgctga agtccggaac gtagtcggca cagcctggtc gccttccacc    7500
tctgggagct ggagtccact gggtggcct gactcccca gtccccttcc cgtgacctgg     7560
tcagggtgag cccatgtgga gtcagcctcg caggcctccc tgccagtagg gtccgagtgt    7620
gtttcatcct tcccactctg tcgagcctgg gggctggagc ggagacggga ggcctggcct    7680
gtctcggaac ctgtgagctg caccaggtag aacgccaggg accccagaat catgtgcgtc    7740
agtccaaggg gtcccctcca ggagtagtga agactccaga aatgtcccctt tcttctcccc   7800 catcctacga gtaattgcat ttgcttttgt aattcttaat gagcaatatc tgctagagag    7860
tttagctgta acagttcttt ttgatcatct ttttttaata attagaaaca ccaaaaaaat    7920
ccagaaactt gttcttccaa agcagagagc attataatca ccagggccaa aagcttccct    7980
ccctgctgtc attgcttctt ctgaggcctg aatccaaaag aaaaacagcc ataggccctt    8040
tcagtggccg ggctacccgt gagcccttcg gaggaccagg gctggggcag cctctgggcc    8100
cacatccggg gccagctccg gcgtgtgttc agtgttagca gtgggtcatg atgctctttc    8160
ccacccagcc tgggataggg gcagaggagg cgaggaggcc gttgccgctg atgtttggcc    8220
gtgaacaggt gggtgtctgc gtgcgtccac gtgcgtgttt tctgactgac atgaaatcga    8280
cgcccgagtt agcctcaccc ggtgacctct agccctgccc ggatggagcg gggcccaccc    8340
ggttcagtgt ttctggggag ctggacagtg gagtgcaaaa ggcttgcaga acttgaagcc    8400
tgctccttcc cttgctacca cggcctcctt tccgtttgat tgtcactgc ttcaatcaat     8460 aacagccgct ccagagtcag tagtcaatga atatatgacc aaatatcacc aggactgtta    8520
ctcaatgtgt gccgagccct tgcccatgct gggctcccgt gtatctggac actgtaacgt    8580
gtgctgtgtt tgctccccctt cccttccttt cttttgccctt tacttgtctt tctggggttt   8640
ttctgtttgg gtttggtttg gtttttattt ctccttttgt gttccaaaca tgaggttctc    8700
tctactggtc ctcttaactg tggtgttgag gcttatattt gtgtaatttt tggtgggtga    8760
aaggaatttt gctaagtaaa tctcttctgt gtttgaactg aagtctgtat tgtaactatg    8820
tttaaagtaa ttgttccaga gacaaatatt tctagacact ttttctttac aaacaaaagc    8880
attcggaggg aggggggatgg tgactgagat gagagggggag agctgaacag atgaccctg    8940
```

```
cccagatcag ccagaagcca cccaaagcag tggagcccag gagtcccact ccaagccagc    9000
aagccgaata gctgatgtgt tgccactttc caagtcactg caaaaccagg ttttgttccg    9060
cccagtggat tcttgttttg cttcccctcc ccccgagatt attaccacca tcccgtgctt    9120
ttaaggaaag gcaagattga tgtttccttg aggggagcca ggaggggatg tgtgtgtgca    9180
gagctgaaga gctggggaga atggggctgg gcccacccaa gcaggaggct gggacgctct    9240
gctgtgggca caggtcaggc taatgttggc agatgcagct cttcctggac aggccaggtg    9300
gtgggcattc tctctccaag gtgtgccccg tgggcattac tgtttaagac acttccgtca    9360
catcccaccc catcctccag ggctcaacac tgtgacatct ctattcccca ccctcccctt    9420
cccagggcaa taaaatgacc atggaggggg cttgcactct cttggctgtc acccgatcgc    9480
cagcaaaact tagatgtgag aaaacccctt cccattccat ggcgaaaaca tctccttaga    9540
aaagccatta ccctcattag gcatggtttt gggctcccaa acacctgac agcccctccc     9600
tcctctgaga ggcggagagt gctgactgta gtgaccattg catgccgggt gcagcatctg    9660
gaagagctag gcagggtgtc tgcccectcc tgagttgaag tcatgctccc ctgtgccagc    9720
ccagaggccg agagctatgg acagcattgc cagtaacaca ggccaccctg tgcagaaggg    9780
agctggctcc agcctggaaa cctgtctgag gttgggagag gtgcacttgg ggcacaggga    9840
gaggccggga cacacttagc tggagatgtc tctaaaagcc ctgtatcgta ttcaccttca    9900
gttttttgtgt tttgggacaa ttactttaga aaataagtag gtcgttttaa aaacaaaaat    9960
tattgattgc tttttttgtag tgttcagaaa aaaggttctt tgtgtatagc caaatgactg   10020
aaaagcactga tatatttaaa aacaaaaggc aatttattaa ggaaatttgt accatttcag   10080
taaacctgtc tgaatgtacc tgtatacgtt tcaaaaacac ccccccccca ctgaatccct   10140
gtaacctatt tattatataa agagtttgcc ttataaattt                         10180

<210> SEQ ID NO 25
<211> LENGTH: 10191
<212> TYPE: DNA
<213> ORGANISM: Homo sapiens

<400> SEQUENCE: 25
ccggaaaatg gccgccgccg ccgccgccgc cgccgccgcg ccgagcggag gaggaggagg      60
aggcgaggag gagagactgc tccataaaaa tacagactca ccagttcctg ctttgatgtg    120
acatgtgact ccccagaata caccttgctt ctgtagacca gctccaacag gattccatgg    180
tagctgggat gttagggctc agggaagaaa agtcagaaga ccaggacctc cagggcctca    240
aggacaaacc cctcaagttt aaaaaggtga agaaagataa gaaagaagag aaagagggca    300
agcatgagcc cgtgcagcca tcagcccacc actctgctga gccgcagag gcaggcaaag    360
cagagacatc agaagggtca ggctccgccc cggctgtgcc ggaagcttct gcctccccca    420
aacagcggcg ctccatcatc cgtgaccggg gacccatgta tgatgacccc accctgcctg    480
aaggctggac acggaagctt aagcaaagga atctggccg ctctgctggg aagtatgatg     540
tgtatttgat caatccccag ggaaaagcct ttcgctctaa agtggagttg attgcgtact    600
tcgaaaaggt aggcgacaca tccctggacc ctaatgattt tgacttcacg gtaactggga    660
gagggagccc ctcccggcga gagcagaaac cacctaagaa gcccaaatct cccaaagctc    720
caggaactgg cagaggccgg ggacgcccca agggagcgg caccacgaga cccaaggcgg    780
ccacgtcaga gggtgtgcag gtgaaaaggg tcctggagaa aagtcctggg aagctccttg    840
tcaagatgcc tttcaaact tcgccagggg gcaaggctga gggggtggg gccaccacat     900
```

```
ccacccaggt catggtgatc aaacgccccg gcaggaagcg aaaagctgag gccgaccctc    960
aggccattcc caagaaacgg ggccgaaagc cggggagtgt ggtggcagcc gctgccgccg   1020
aggccaaaaa gaaagccgtg aaggagtctt ctatccgatc tgtgcaggag accgtactcc   1080
ccatcaagaa gcgcaagacc cgggagacgg tcagcatcga ggtcaaggaa gtggtgaagc   1140
ccctgctggt gtccaccctc ggtgagaaga gcgggaaagg actgaagacc tgtaagagcc   1200
ctgggcggaa aagcaaggag agcagcccca aggggcgcag cagcagcgcc tcctcacccc   1260
ccaagaagga gcaccaccac catcaccacc actcagagtc cccaaaggcc cccgtgccac   1320
tgctcccacc cctgccccca cctccacctg agcccgagag ctccgaggac cccaccagcc   1380
cccctgagcc ccaggacttg agcagcagcg tctgcaaaga ggagaagatg cccagaggag   1440
gctcactgga gagcgacggc tgccccaagg agccagctaa gactcagccc gcggttgcca   1500
ccgccgccac ggccgcagaa aagtacaaac accgagggga gggagagcgc aaagacattg   1560
tttcatcctc catgccaagg ccaaacagag aggagcctgt ggacagccgg acgcccgtga   1620
ccgagagagt tagctgactt tacacggagc ggattgcaaa gcaaaccaac aagaataaag   1680
gcagctgttg tctcttctcc ttatgggtag ggctctgaca aagcttcccg attaactgaa   1740
ataaaaaata ttttttttc tttcagtaaa cttagagttt cgtggcttca gggtgggagt   1800
agttggagca ttggggatgt ttttcttacc gacaagcaca gtcaggttga agacctaacc   1860
agggccagaa gtagctttgc acttttctaa actaggctcc ttcaacaagg cttgctgcag   1920
atactactga ccagacaagc tgttgaccag gcacctcccc tcccgcccaa accttttccc   1980
catgtggtcg ttagagacag agcgacagag cagttgagag gacactcccg ttttcggtgc   2040
catcagtgcc ccgtctacag ctcccccagc tcccccacc tccccactc ccaaccacgt   2100 tgggacaggg aggtgtgagg caggagagac agttggattc tttagagaag atggatatga   2160
ccagtggcta tggcctgtgc gatcccaccc gtggtggctc aagtctggcc ccacaccagc   2220
cccaatccaa aactggcaag gacgcttcac aggacaggaa agtggcacct gtctgctcca   2280
gctctggcat ggctaggagg ggggagtccc ttgaactact gggtgtagac tggcctgaac   2340
cacaggagag gatggcccag ggtgaggtgg catggtccat tctcaaggga cgtcctccaa   2400
cgggtggcgc tagaggccat ggaggcagta ggacaaggtg caggcaggct ggcctggggt   2460
caggccgggc agagcacagc ggggtgagag ggattcctaa tcactcagag cagtctgtga   2520
cttagtggac aggggagggg gcaaaggggg aggagaagaa aatgttcttc cagttacttt   2580
ccaattctcc tttagggaca gcttagaatt atttgcacta ttgagtcttc atgttcccac   2640
ttcaaaacaa acagatgctc tgagagcaaa ctggcttgaa ttggtgacat ttagtccctc   2700
aagccaccag atgtgacagt gttgagaact acctggattt gtatatatac ctgcgcttgt   2760
tttaaagtgg gctcagcaca tagggttccc acgaagctcc gaaactctaa gtgtttgctg   2820
caattttata aggacttcct gattggtttc tcttctcccc ttccattcct gccttttgtt   2880
catttcatcc tttcacttct ttcccttcct ccgtcctcct ccttcctagt tcatcccttc   2940
tcttccaggc agccgcggtg cccaaccaca cttgtcggct ccagtcccca gaactctgcc   3000 tgcccttttgt cctcctgctg ccagtaccag ccccaccctg ttttgagccc tgaggaggcc   3060
ttgggctctg ctgagtccga cctggcctgt ctgtgaagag caagagagca gcaaggtctt   3120
gctctcctag gtagccccct cttccctggt aagaaaaagc aaaaggcatt tcccaccctg   3180
aacaacgagc cttttcaccc ttctactcta gagaagtgga ctggaggagc tgggcccgat   3240
```

```
ttggtagttg aggaaagcac agaggcctcc tgtggcctgc cagtcatcga gtggcccaac   3300
aggggctcca tgccagccga ccttgacctc actcagaagt ccagagtcta gcgtagtgca   3360
gcagggcagt agcggtacca atgcagaact cccaagaccc gagctgggac cagtacctgg   3420
gtccccagcc cttcctctgc tcccccttt  ccctcgagt tcttcttgaa tggcaatgtt   3480
ttgcttttgc tcgatgcaga caggggggcca gaacaccaca catttcactg tctgtctggt   3540
ccatagctgt ggtgtagggg cttagaggca tgggcttgct gtgggttttt aattgatcag   3600
ttttcatgtg ggatcccatc tttttaacct ctgttcagga agtccttatc tagctgcata   3660
tcttcatcat attggtatat ccttttctgt gtttacagag atgtctctta tatctaaatc   3720
tgtccaactg agaagtacct tatcaaagta gcaaatgaga cagcagtctt atgcttccag   3780
aaacacccac aggcatgtcc catgtgagct gctgccatga actgtcaagt gtgtgttgtc   3840
ttgtgtattt cagttattgt ccctggcttc cttactatgg tgtaatcatg aaggagtgaa   3900
acatcataga aactgtctag cacttccttg ccagtcttta gtgatcagga accatagttg   3960
acagttccaa tcagtagctt aagaaaaaac cgtgtttgtc tcttctggaa tggttagaag   4020
tgagggagtt tgccccgttc tgtttgtaga gtctcatagt tggactttct agcatatatg   4080
tgtccatttc cttatgctgt aaaagcaagt cctgcaacca aactcccatc agcccaatcc   4140
ctgatccctg atcccttcca cctgctctgc tgatgacccc cccagcttca cttctgactc   4200
ttccccagga agggaagggg ggtcagaaga gagggtgagt cctccagaac tcttcctcca   4260
aggacagaag gctcctgccc ccatagtggc ctcgaactcc tggcactacc aaaggacact   4320
tatccacgag agcgcagcat ccgaccaggt tgtcactgag aagatgttta ttttggtcag   4380
ttgggttttt atgtattata cttagtcaaa tgtaatgtgg cttctggaat cattgtccag   4440
agctgcttcc ccgtcacctg ggcgtcatct ggtcctggta agaggagtgc gtggcccacc   4500
aggccccccct gtcacccatg acagttcatt cagggccgat ggggcagtcg tggttgggaa   4560
cacagcattt caagcgtcac tttatttcat tcgggcccca cctgcagctc cctcaaagag   4620
gcagttgccc agcctctttc ccttccagtt tattccagag ctgccagtgg ggcctgaggc   4680
tccttagggt tttctctcta tttccccctt tcttcctcat tccctcgtct ttcccaaagg   4740
catcacgagt cagtcgcctt tcagcaggca gccttggcgg tttatcgccc tggcaggcag   4800
gggccctgca gctctcatgc tgcccctgcc ttggggtcag gttgacagga ggttggaggg   4860
aaagccttaa gctgcaggat tctcaccagc tgtgtccggc ccagttttgg ggtgtgacct   4920
caatttcaat tttgtctgta cttgaacatt atgaagatgg gggcctcttt cagtgaattt   4980
gtgaacagca gaattgaccg acagctttcc agtacccatg gggctaggtc attaaggcca   5040
catccacagt ctcccccacc cttgttccag ttgttagtta ctacctcctc tcctgacaat   5100
actgtatgtc gtcgagctcc ccccaggtct accccctcccg gccctgcctg ctggtgggct   5160
tgtcatagcc agtgggattg ccggtcttga cagctcagtg agctggagat acttggtcac   5220
agccaggcgc tagcacagct cccttctgtt gatgctgtat tcccatatca aaagacacag   5280
gggacaccca gaaacgccac atcccccaat ccatcagtgc caaactagcc aacggcccca   5340
gcttctcagc tcgctggatg gcggaagctg ctactcgtga gcgccagtgc gggtgcagac   5400
aatcttctgt tgggtggcat cattccaggc ccgaagcatg aacagtgcac ctgggacagg   5460
gagcagcccc aaattgtcac ctgcttctct gcccagcttt tcattgctgt gacagtgatg   5520
gcgaaagagg gtaataacca gacacaaact gccaagttgg gtggagaaag gagtttcttt   5580
agctgacaga atctctgaat tttaaatcac ttagtaagcg gctcaagccc aggagggagc   5640
```

```
agagggatac gagcggagtc ccctgcgcgg gaccatctgg aattggttta gcccaagtgg    5700
agcctgacag ccagaactct gtgtcccccg tctaaccaca gctccttttc cagagcattc    5760
cagtcaggct ctctgggctg actgggccag gggaggttac aggtaccagt tctttaagaa    5820
gatctttggg catatacatt tttagcctgt gtcattgccc caaatggatt cctgtttcaa    5880
gttcacacct gcagattcta ggacctgtgt cctagacttc agggagtcag ctgtttctag    5940
agttcctacc atggagtggg tctggaggac ctgcccggtg gggggcaga gccctgctcc     6000 ctccgggtct tcctactctt ctctctgctc tgacgggatt tgttgattct ctccattttg    6060
gtgtctttct cttttagata ttgtatcaat ctttagaaaa ggcatagtct acttgttata    6120
aatcgttagg atactgcctc ccccagggtc taaaattaca tattagaggg gaaaagctga    6180
acactgaagt cagttctcaa caatttagaa ggaaaaccta gaaacatttt ggcagaaaat    6240
tacatttcga tgttttgaa tgaatacgag caagctttta caacagtgct gatctaaaaa     6300
tacttagcac ttggcctgag atgcctggtg agcattacag gcaagggaa tctggaggta     6360 gccgacctga ggacatggct tctgaacctg tcttttggga gtggtatgga aggtggagcg    6420
ttcaccagtg acctggaagg cccagcacca ccctccttcc cactcttctc atcttgacag    6480
agcctgcccc agcgctgacg tgtcaggaaa acacccaggg aactaggaag gcacttctgc    6540
ctgaggggca gcctgccttg cccactcctg ctctgctcgc ctcggatcag ctgagccttc    6600
tgagctggcc tctcactgcc tccccaaggc ccctgcctg cctgtcagg aggcagaagg      6660 aagcaggtgt gagggcagtg caaggaggga gcacaacccc cagctcccgc tccgggctcc    6720
gacttgtgca caggcagagc ccagaccctg gaggaaatcc tacctttgaa ttcaagaaca    6780
tttggggaat ttggaaatct ctttgccccc aaaccccat tctgtcctac ctttaatcag     6840
gtcctgctca gcagtgagag cagatgaggt gaaaaggcca agaggtttgg ctcctgccca    6900
ctgatagccc ctctcccgc agtgtttgtg tgtcaagtgg caaagctgtt cttcctggtg     6960
accctgatta tatccagtaa cacatagact gtgcgcatag gcctgctttg tctcctctat    7020
cctgggcttt tgttttgctt tttagttttg cttttagttt ttctgtccct tttatttaac    7080
gcaccgacta gacacacaaa gcagttgaat ttttatatat atatctgtat attgcacaat    7140
tataaactca ttttgcttgt ggctccacac acacaaaaaa agacctgtta aaattatacc    7200
tgttgcttaa ttacaatatt tctgataacc atagcatagg acaagggaaa ataaaaaaag    7260 aaaaaaaga aaaaaaacg acaaatctgt ctgctggtca cttcttctgt ccaagcagat     7320
tcgtggtctt ttcctcgctt cttttcaaggg cttttcctgtg ccaggtgaag gaggctccag   7380
gcagcaccca ggttttgcac tcttgtttct cccgtgcttg tgaaagaggt cccaaggttc    7440
tgggtgcagg agcgctccct tgacctgctg aagtccggaa cgtagtcggc acagcctggt    7500
cgccttccac ctctgggagc tggagtccac tggggtggcc tgactccccc agtccccttc    7560
ccgtgacctg gtcagggtga gcccatgtgg agtcagcctc gcaggcctcc ctgccagtag    7620
ggtccgagtg tgtttcatcc ttcccactct gtcgagcctg ggggctggag cggagacggg    7680
aggcctggcc tgtctcggaa cctgtgagct gcaccaggta gaacgccagg gaccccagaa    7740
tcatgtgcgt cagtccaagg ggtcccctcc aggagtagta aagactccag aaatgtccct    7800
ttcttctccc ccatcctacg agtaattgca tttgcttttg taattcttaa tgagcaatat    7860
ctgctagaga gttagctgt aacagttctt tttgatcatc ttttttttaat aattagaaac    7920 accaaaaaaa tccagaaact tgttcttcca aagcagagag cattataatc accagggcca    7980
```

```
aaagcttccc tccctgctgt cattgcttct tctgaggcct gaatccaaaa gaaaaacagc    8040
cataggccct ttcagtggcc gggctacccg tgagcccttc ggaggaccag ggctggggca    8100
gcctctgggc ccacatccgg ggccagctcc ggcgtgtgtt cagtgttagc agtgggtcat    8160
gatgctcttt cccacccagc ctgggatagg ggcagaggag gcgaggaggc cgttgccgct    8220
gatgtttggc cgtgaacagg tgggtgtctg cgtgcgtcca cgtgcgtgtt ttctgactga    8280
catgaaatcg acgcccgagt tagcctcacc cggtgacctc tagccctgcc cggatggagc    8340
ggggcccacc cggttcagtg tttctgggga gctggacagt ggagtgcaaa aggcttgcag    8400
aacttgaagc ctgctccttc ccttgctacc acggcctcct ttccgtttga tttgtcactg    8460
cttcaatcaa taacagccgc tccagagtca gtagtcaatg aatatatgac caaatatcac    8520
caggactgtt actcaatgtg tgccgagccc ttgcccatgc tgggctcccg tgtatctgga    8580
cactgtaacg tgtgctgtgt ttgctcccct tccccttcct tctttgccct ttacttgtct    8640
ttctggggtt tttctgtttg ggtttggttt ggtttttatt tctccttttg tgttccaaac    8700
atgaggttct ctctactggt cctcttaact gtggtgttga ggcttatatt tgtgtaattt    8760
ttggtgggtg aaaggaattt tgctaagtaa atctcttctg tgtttgaact gaagtctgta    8820
ttgtaactat gtttaaagta attgttccag agacaaatat ttctagacac tttttctttta   8880 caaacaaaag cattcggagg gaggggatg gtgactgaga tgagagggga gagctgaaca    8940
gatgacccct gcccagatca gccagaagcc acccaaagca gtggagccca ggagtcccac    9000
tccaagccag caagccgaat agctgatgtg ttgccacttt ccaagtcact gcaaaaccag    9060
gttttgttcc gcccagtgga ttcttgtttt gcttcccctc cccccgagat tattaccacc    9120
atcccgtgct tttaaggaaa ggcaagattg atgtttcctt gaggggagcc aggaggggat    9180
gtgtgtgtgc agagctgaag agctggggag aatggggctg ggcccaccca agcaggaggc    9240
tgggacgctc tgctgtgggc acaggtcagg ctaatgttgg cagatgcagc tcttcctgga    9300
caggccaggt ggtgggcatt ctctctccaa ggtgtgcccc gtgggcatta ctgtttaaga    9360
cacttccgtc acatcccacc ccatcctcca gggctcaaca ctgtgacatc tctattcccc    9420 acccccctt ccccagggca ataaaatgac catggagggg gcttgcactc tcttggctgt     9480
cacccgatcg ccagcaaaac ttagatgtga gaaaacccct tcccattcca tggcgaaaac    9540
atctccttag aaaagccatt accctcatta ggcatggttt tgggctccca aaacacctga    9600
cagcccctcc ctcctctgag aggcggagag tgctgactgt agtgaccatt gcatgccggg    9660
tgcagcatct ggaagagcta ggcagggtgt ctgcccctc ctgagttgaa gtcatgctcc     9720
cctgtgccag cccagaggcc gagagctatg gacagcattg ccagtaacac aggccaccct    9780
gtgcagaagg gagctggctc cagcctggaa acctgtctga ggttgggaga ggtgcacttg    9840
gggcacaggg agaggccggg acacacttag ctggagatgt ctctaaaagc cctgtatcgt    9900
attccccttc agttttttgtg ttttgggaca attactttag aaaataagta ggtcgttttta  9960 aaaacaaaaa ttattgattg cttttttgta gtgttcagaa aaaggttct ttgtgtatag    10020 ccaaatgact gaaagcactg atatatttaa aaacaaaagg caatttatta aggaaatttg   10080
taccatttca gtaaacctgt ctgaatgtac ctgtatacgt ttcaaaaaca ccccccccc    10140 actgaatccc tgtaacctat ttattatata aagagtttgc cttataaatt t            10191

<210> SEQ ID NO 26
<211> LENGTH: 10179
<212> TYPE: DNA
<213> ORGANISM: Homo sapiens
```

<400> SEQUENCE: 26

```
ccggaaaatg gccgccgccg ccgccgcgcc gagcggagga ggaggaggag gcgaggagga     60
gagactgctc cataaaaata cagactcacc agttcctgct ttgatgtgac atgtgactcc    120
ccagaataca ccttgcttct gtagaccagc tccaacagga ttccatggta gctgggatgt    180
tagggctcag ggaagaaaag tcagaagacc aggacctcca gggcctcaag acaaacccc    240
tcaagtttaa aaaggtgaag aaagataaga aagaagagaa agagggcaag catgagcccg    300
tgcagccatc agcccaccac tctgctgagc ccgcagaggc aggcaaagca gagacatcag    360
aagggtcagg ctccgcccg gctgtgccgg aagcttctgc ctccccaaa cagcggcgct    420
ccatcatccg tgaccgggga cccatgtatg atgaccccac cctgcctgaa ggctggacac    480
ggaagcttaa gcaaaggaaa tctggccgct ctgctgggaa gtatgatgtg tatttgatca    540
atccccaggg aaaagccttt cgctctaaag tggagttgat tgcgtacttc gaaaaggtag    600
gcgacacatc cctggaccct aatgattttg acttcacggt aactgggaga gggagcccct    660
cccggcgaga gcagaaacca cctaagaagc ccaaatctcc caaagctcca ggaactggca    720
gaggccgggg acgccccaaa gggagcggca ccacgagacc caaggcggcc acgtcagagg    780
gtgtgcaggt gaaaagggtc ctggagaaaa gtcctgggaa gctccttgtc aagatgcctt    840
ttcaaacttc gccaggggc aaggctgagg ggggtgggc caccacatcc acccaggtca    900
tggtgatcaa acgccccggc aggaagcgaa aagctgaggc cgaccctcag gccattccca    960
agaaacgggg ccgaaagccg gggagtgtgg tggcagccgc tgccgccgag gccaaaaaga   1020
aagccgtgaa ggagtcttct atccgatctg tgcaggagac cgtactcccc atcaagaagc   1080
gcaagacccg ggagacggtc agcatcgagg tcaaggaagt ggtgaagccc ctgctggtgt   1140
ccaccctcgg tgagaagagc gggaaaggac tgaagacctg taagagccct gggcggaaaa   1200
gcaaggagag cagccccaag gggcgcagca gcagcgcctc ctcaccccc aagaaggagc   1260
accaccacca tcaccaccac tcagagtccc caaaggcccc cgtgccactg ctcccaccc   1320
tgccccacc tccacctgag cccgagagct ccgaggaccc caccagcccc cctgagcccc   1380
aggacttgag cagcagcgtc tgcaaagagg agaagatgcc cagaggaggc tcactggaga   1440
gcgacggctg ccccaaggag ccagctaaga ctcagcccgc ggttgccacc gccgccacgg   1500
ccgcagaaaa gtacaaacac cgaggggagg gagagcgcaa agacattgtt tcatcctcca   1560
tgccaaggcc aaacagagag gagcctgtgg acagccggac gcccgtgacc gagagagtta   1620
gctgactttta cacggagcgg attgcaaagc aaaccaacaa gaataaaggc agctgttgtc   1680
tcttctcctt atgggtaggg ctctgacaaa gcttcccgat taactgaaat aaaaaatatt   1740
tttttttctt tcagtaaact tagagtttcg tggcttcagg gtgggagtag ttggagcatt   1800
ggggatgttt ttcttaccga caagcacagt caggttgaag acctaaccag ggccagaagt   1860
agctttgcac ttttctaaac taggctcctt caacaaggct tgctgcagat actactgacc   1920
agacaagctg ttgaccaggc acctcccctc ccgcccaaac ctttccccca tgtggtcgtt   1980
agagacagag cgacagagca gttgagagga cactcccgtt ttcggtgcca tcagtgcccc   2040
gtctacagct ccccccagctc cccccacctc ccccactccc aaccacgttg ggacagggag   2100
gtgtgaggca ggagagacag ttggattctt tagagaagat ggatatgacc agtggctatg   2160
gcctgtgcga tccacccgt ggtggctcaa gtctggcccc acaccagccc caatccaaaa   2220
ctggcaagga cgcttcacag gacaggaaag tggcacctgt ctgctccagc tctggcatgg   2280
```

```
ctaggagggg ggagtcccett gaactactgg gtgtagactg gectgaacca caggagagga    2340 tggcccaggg tgaggtggca tggtccattc tcaaggacg tcctccaacg ggtggcgcta     2400
gaggccatgg aggcagtagg acaaggtgca ggcaggctgg cctggggtca ggccgggcag    2460
agcacagcgg ggtgagaggg attcctaatc actcagagca gtctgtgact tagtggacag    2520 gggaggggc aaaggggag gagaagaaaa tgttcttcca gttactttcc aattctcctt     2580
tagggacagc ttagaattat ttgcactatt gagtcttcat gttcccactt caaaacaaac    2640
agatgctctg agagcaaact ggcttgaatt ggtgacattt agtccctcaa gccaccagat    2700
gtgacagtgt tgagaactac ctggatttgt atatatacct gcgcttgttt taaagtgggc    2760
tcagcacata gggttcccac gaagctccga aactctaagt gtttgctgca attttataag    2820
gacttcctga ttggtttctc ttctcccctt ccatttctgc cttttgttca tttcatcctt    2880
tcacttcttt cccttcctcc gtcctcctcc ttcctagttc atcccttctc ttccaggcag    2940
ccgcggtgcc caaccacact tgtcggctcc agtcccccaga actctgcctg ccctttgtcc  3000
tcctgctgcc agtaccagcc ccaccctgtt ttgagccctg aggaggcctt gggctctgct    3060
gagtccgacc tggcctgtct gtgaagagca agagagcagc aaggtcttgc tctcctaggt    3120
agccccctct tccctggtaa gaaaagcaa aaggcatttc ccaccctgaa caacgagcct    3180 tttcacccctt ctactctaga gaagtggact ggaggagctg ggcccgattt ggtagttgag   3240
gaaagcacag aggcctcctg tggcctgcca gtcatcgagt ggcccaacag gggctccatg   3300
ccagccgacc ttgacctcac tcagaagtcc agagtctagc gtagtgcagc agggcagtag   3360
cggtaccaat gcagaactcc caagacccga gctgggacca gtacctgggt ccccagccct   3420
tcctctgctc ccccttttcc ctcggagttc ttcttgaatg gcaatgttt tgcttttgctc   3480 gatgcagaca gggggccaga acaccacaca tttcactgtc tgtctggtcc atagctgtgg   3540
tgtaggggct tagaggcatg ggcttgctgt gggttttaa ttgatcagtt ttcatgtggg    3600
atcccatctt tttaacctct gttcaggaag tccttatcta gctgcatatc ttcatcatat    3660
tggtatatcc ttttctgtgt ttacagagat gtctcttata tctaaatctg tccaactgag    3720
aagtacctta tcaaagtagc aaatgagaca gcagtcttat gcttccagaa acacccacag    3780
gcatgtccca tgtgagctgc tgccatgaac tgtcaagtgt gtgttgtctt gtgtatttca    3840
gttattgtcc ctggcttcct tactatggtg taatcatgaa ggagtgaaac atcatagaaa   3900
ctgtctagca cttccttgcc agtctttagt gatcaggaac catagttgac agttccaatc    3960
agtagcttaa gaaaaaccg tgtttgtctc ttctggaatg gttagaagtg agggagtttg    4020
ccccgttctg tttgtagagt ctcatagttg gactttctag catatatgtg tccatttcct    4080
tatgctgtaa aagcaagtcc tgcaaccaaa ctcccatcag cccaatccct gatccctgat    4140
cccttccacc tgctctgctg atgaccccccc cagcttcact tctgactctt ccccaggaag   4200 ggaaggggg tcagaagaga gggtgagtcc tccagaactc ttcctccaag acagaaggc    4260 tcctgccccc atagtggcct cgaactcctg gcactaccaa aggacactta ccacgagag     4320 cgcagcatcc gaccaggttg tcactgagaa gatgtttatt ttggtcagtt gggttttat    4380 gtattatact tagtcaaatg taatgtggct tctggaatca ttgtccagag ctgcttcccc    4440
gtcacctggg cgtcatctgg tcctggtaag aggagtgcgt ggcccaccag gcccccctgt    4500
cacccatgac agttcattca gggccgatgg ggcagtcgtg gttgggaaca cagcatttca    4560
agcgtcactt tatttcattc gggccccacc tgcagctccc tcaaagaggc agttgcccag    4620
cctcttcccc ttccagttta ttccagagct gccagtgggg cctgaggctc cttagggttt    4680
```

```
tctctctatt tccccctttc ttcctcattc cctcgtcttt cccaaaggca tcacgagtca    4740
gtcgcctttc agcaggcagc cttggcggtt tatcgccctg gcaggcaggg gccctgcagc    4800
tctcatgctg cccctgcctt ggggtcaggt tgacaggagg ttggagggaa agccttaagc    4860
tgcaggattc tcaccagctg tgtccggccc agttttgggg tgtgacctca atttcaattt    4920
tgtctgtact tgaacattat gaagatgggg gcctctttca gtgaatttgt gaacagcaga    4980
attgaccgac agctttccag tacccatggg gctaggtcat taaggccaca tccacagtct    5040
cccccaccct tgttccagtt gttagttact acctcctctc ctgacaatac tgtatgtcgt    5100
cgagctcccc ccaggtctac ccctcccggc cctgcctgct ggtgggcttg tcatagccag    5160
tgggattgcc ggtcttgaca gctcagtgag ctggagatac ttggtcacag ccaggcgcta    5220
gcacagctcc cttctgttga tgctgtattc ccatatcaaa agacacaggg gacacccaga    5280
aacgccacat cccccaatcc atcagtgcca aactagccaa cggccccagc ttctcagctc    5340
gctggatggc ggaagctgct actcgtgagc gccagtgcgg gtgcagacaa tcttctgttg    5400
ggtggcatca ttccaggccc gaagcatgaa cagtgcacct gggacaggga gcagcccaa    5460 attgtcacct gcttctctgc ccagcttttc attgctgtga cagtgatggc gaaagagggt    5520
aataaccaga cacaaactgc caagttgggt ggagaaagga gtttctttag ctgacagaat    5580
ctctgaattt taaatcactt agtaagcggc tcaagcccag gagggagcag agggatacga    5640
gcggagtccc ctgcgcggga ccatctggaa ttggtttagc ccaagtggag cctgacagcc    5700
agaactctgt gtccccgtc taaccacagc tcctttccca gagcattcca gtcaggctct    5760
ctgggctgac tgggccaggg gaggttacag gtaccagttc tttaagaaga tctttgggca    5820
tatacatttt tagcctgtgt cattgcccca aatggattcc tgtttcaagt tcacacctgc    5880
agattctagg acctgtgtcc tagacttcag ggagtcagct gtttctagag ttcctaccat    5940
ggagtgggtc tggaggacct gcccggtggg ggggcagagc cctgctcct ccgggtcttc    6000 ctactcttct ctctgctctg acgggatttg ttgattctct ccatttggt gtctttctct    6060 tttagatatt gtatcaatct ttagaaaagg catagtctac ttgttataaa tcgttaggat    6120
actgcctccc ccagggtcta aaattacata ttagagggga aaagctgaac actgaagtca    6180
gttctcaaca atttagaagg aaaacctaga aaacatttgg cagaaaatta catttcgatg    6240
tttttgaatg aatacgagca agcttttaca acagtgctga tctaaaaata cttagcactt    6300
ggcctgagat gcctggtgag cattacaggc aagggaatc tggaggtagc cgacctgagg    6360
acatggcttc tgaacctgtc ttttgggagt ggtatggaag gtggagcgtt caccagtgac    6420
ctggaaggcc cagcaccacc ctccttccca ctcttctcat cttgacagag cctgccccag    6480
cgctgacgtg tcaggaaaac acccagggaa ctaggaaggc acttctgcct gaggggcagc    6540
ctgccttgcc cactcctgct ctgctcgcct cggatcagct gagccttctg agctggcctc    6600
tcactgcctc cccaaggccc cctgcctgcc tgtcaggag gcagaaggaa gcaggtgtga    6660
gggcagtgca aggagggagc acaaccccca gctcccgctc cgggctccga cttgtgcaca    6720
ggcagagccc agaccctgga ggaaatccta cctttgaatt caagaacatt tggggaattt    6780
ggaaatctct ttgcccccaa accccattc tgtcctacct ttaatcaggt cctgctcagc    6840
agtgagagca gatgaggtga aaaggccaag aggtttggct cctgcccact gatagcccct    6900
ctccccgcag tgtttgtgtg tcaagtggca aagctgttct tcctggtgac cctgattata    6960
tccagtaaca catagactgt gcgcataggc ctgctttgtc tcctctatcc tgggcttttg    7020
```

```
tttgctttt tagttttgct tttagttttt ctgtccctttt tatttaacgc accgactaga   7080
cacacaaagc agttgaattt ttatatatat atctgtatat tgcacaatta taaactcatt   7140
ttgcttgtgg ctccacacac acaaaaaaag acctgttaaa attatacctg ttgcttaatt   7200
acaatatttc tgataaccat agcataggac aagggaaaat aaaaaaagaa aaaaagaaa    7260
aaaaaacgac aaatctgtct gctggtcact tcttctgtcc aagcagattc gtggtctttt   7320
cctcgcttct ttcaagggct ttcctgtgcc aggtgaagga ggctccaggc agcacccagg   7380
ttttgcactc ttgtttctcc cgtgcttgtg aaagaggtcc caaggttctg ggtgcaggag   7440
cgctcccttg acctgctgaa gtccggaacg tagtcggcac agcctggtcg ccttccacct   7500
ctgggagctg gagtccactg gggtggcctg actcccccag tcccctttccc gtgacctggt  7560
cagggtgagc ccatgtggag tcagcctcgc aggcctccct gccagtaggg tccgagtgtg   7620
tttcatcctt cccactctgt cgagcctggg ggctggagcg gagacgggag gcctggcctg   7680
tctcggaacc tgtgagctgc accaggtaga acgccaggga ccccagaatc atgtgcgtca   7740
gtccaagggg tccctccag gagtagtgaa gactccagaa atgtcccttt cttctccccc    7800
atcctacgag taattgcatt tgcttttgta attcttaatg agcaatatct gctagagagt   7860
ttagctgtaa cagttctttt tgatcatctt tttttaataa ttagaaacac caaaaaaatc   7920
cagaaacttg ttcttccaaa gcagagagca ttataatcac cagggccaaa agcttccctc   7980
cctgctgtca ttgcttcttc tgaggcctga atccaaaaga aaaacagcca taggcccttt   8040
cagtggccgg gctacccgtg agcccttcgg aggaccaggg ctggggcagc ctctgggccc   8100
acatccgggg ccagctccgg cgtgtgttca gtgttagcag tgggtcatga tgctctttcc   8160
cacccagcct gggataggg cagaggaggc gaggaggccg ttgccgctga tgtttggccg    8220
tgaacaggtg ggtgtctgcg tgcgtccacg tgcgtgtttt ctgactgaca tgaaatcgac   8280
gcccgagtta gcctcacccg gtgacctcta gccctgcccg gatggagcgg ggcccacccg   8340
gttcagtgtt tctggggagc tggacagtgg agtgcaaaag gcttgcagaa cttgaagcct   8400
gctccttccc ttgctaccac ggcctccttt ccgtttgatt tgtcactgct tcaatcaata   8460
acagccgctc cagagtcagt agtcaatgaa tatatgacca aatatcacca ggactgttac   8520
tcaatgtgtg ccgagcccctt gcccatgctg ggctcccgtg tatctggaca ctgtaacgtg   8580
tgctgtgttt gctccccttc ccttccttc tttgcccttt acttgtcttt ctggggtttt     8640
tctgtttggg tttggtttgg ttttttatttc tccttttgtg ttccaaacat gaggttctct    8700
ctactggtcc tcttaactgt ggtgttgagg cttatatttg tgtaattttt ggtgggtgaa   8760
aggaattttg ctaagtaaat ctcttctgtg tttgaactga agtctgtatt gtaactatgt    8820
ttaaagtaat tgttccagag acaaatattt ctagacactt tttcttttaca aacaaaagca   8880
ttcggaggga gggggatggt gactgagatg agaggggaga gctgaacaga tgacccctgc   8940
ccagatcagc cagaagccac ccaaagcagt ggagcccagg agtcccactc caagccagca   9000
agccgaatag ctgatgtgtt gccactttcc aagtcactgc aaaaccaggt tttgttccgc   9060
ccagtggatt cttgttttgc ttcccctccc cccgagatta ttaccaccat cccgtgctttt  9120
taaggaaagg caagattgat gtttccttga ggggagccag gaggggatgt gtgtgtgcag   9180
agctgaagag ctggggagaa tggggctggg cccacccaag caggaggctg ggacgctctg   9240
ctgtgggcac aggtcaggct aatgttggca gatgcagctc ttcctggaca ggccaggtgg   9300
tgggcattct ctctccaagg tgtgcccgt gggcattact gtttaagaca cttccgtcac    9360
atcccacccc atcctccagg gctcaacact gtgacatctc tattccccac cctccccttc   9420
```

| | |
|---|---|
| ccagggcaat aaaatgacca tggagggggc ttgcactctc ttggctgtca cccgatcgcc | 9480 |
| agcaaaactt agatgtgaga aaaccccttc ccattccatg gcgaaaacat ctccttagaa | 9540 |
| aagccattac cctcattagg catggttttg ggctcccaaa acacctgaca gcccctccct | 9600 |
| cctctgagag gcggagagtg ctgactgtag tgaccattgc atgccgggtg cagcatctgg | 9660 |
| aagagctagg cagggtgtct gcccctcct gagttgaagt catgctcccc tgtgccagcc | 9720 |
| cagaggccga gagctatgga cagcattgcc agtaacacag gccaccctgt gcagaaggga | 9780 |
| gctggctcca gcctggaaac ctgtctgagg ttgggagagg tgcacttggg gcacagggag | 9840 |
| aggccgggac acactagct ggagatgtct ctaaaagccc tgtatcgtat tcaccttcag | 9900 |
| tttttgtgtt ttgggacaat tactttagaa aataagtagg tcgtttttaaa aacaaaaatt | 9960 |
| attgattgct tttttgtagt gttcagaaaa aaggttcttt gtgtatagcc aaatgactga | 10020 |
| aagcactgat atatttaaaa acaaaaggca atttattaag gaaatttgta ccatttcagt | 10080 |
| aaacctgtct gaatgtacct gtatacgttt caaaaacacc cccccccccac tgaatccctg | 10140 |
| taacctattt attatataaa gagtttgcct tataaattt | 10179 |

<210> SEQ ID NO 27
<211> LENGTH: 10185
<212> TYPE: DNA
<213> ORGANISM: Homo sapiens

<400> SEQUENCE: 27

| | |
|---|---|
| ccggaaaatg gccgccgccg ccgccgccgc gccgagcgga ggaggaggag gaggaggcga | 60 |
| ggaggagaga ctgctccata aaatacaga ctcaccagtt cctgctttga tgtgacatgt | 120 |
| gactccccag aatacacctt gcttctgtag accagctcca acaggattcc atggtagctg | 180 |
| ggatgttagg gctcagggaa gaaaagtcag aagaccagga cctccagggc ctcaaggaca | 240 |
| aaccctcaa gtttaaaaag gtgaagaaag ataagaaaga agagaaagag ggcaagcatg | 300 |
| agcccgtgca gccatcagcc caccactctg ctgagcccgc agaggcaggc aaagcagaga | 360 |
| catcagaagg gtcaggctcc gccccggctg tgccggaagc ttctgcctcc cccaaacagc | 420 |
| ggcgctccat catccgtgac cggggaccca tgtatgatga ccccaccctg cctgaaggct | 480 |
| ggacacggaa gcttaagcaa aggaaatctg gccgctctgc tgggaagtat gatgtgtatt | 540 |
| tgatcaatcc ccagggaaaa gcctttcgct ctaaagtgga gttgattgcg tacttcgaaa | 600 |
| aggtaggcga cacatccctg gaccctaatg attttgactt cacggtaact gggagaggga | 660 |
| gcccctcccg gcgagagcag aaaccaccta agaagcccaa atctcccaaa gctccaggaa | 720 |
| ctggcagagg ccggggacgc cccaagggga gcggcaccac gagacccaag gcggccacgt | 780 |
| cagagggtgt gcaggtgaaa agggtcctgg agaaaagtcc tgggaagctc cttgtcaaga | 840 |
| tgccttttca aacttcgcca gggggcaagg ctgagggggg tggggccacc acatccaccc | 900 |
| aggtcatggt gatcaaacgc cccggcagga agcgaaaagc tgaggccgac cctcaggcca | 960 |
| ttcccaagaa acgggccga aagccgggga gtgtggtggc agccgctgcc gccgaggcca | 1020 |
| aaaagaaagc cgtgaaggag tcttctatcc gatctgtgca ggagaccgta ctccccatca | 1080 |
| agaagcgcaa gacccgggag acggtcagca tcgaggtcaa ggaagtggtg aagccctgc | 1140 |
| tggtgtccac cctcggtgag aagagcggga aaggactgaa gacctgtaag agccctgggc | 1200 |
| ggaaaagcaa ggagagcagc cccagggggc gcagcagcag cgcctcctca ccccccaaga | 1260 |
| aggagcacca ccaccatcac caccactcag agtcccaaaa ggccccgtg ccactgctcc | 1320 |

```
caccccctgcc cccacctcca cctgagcccg agagctccga ggaccccacc agcccccctg    1380
agccccagga cttgagcagc agcgtctgca aagaggagaa gatgcccaga ggaggctcac    1440
tggagagcga cggctgcccc aaggagccag ctaagactca gcccgcggtt gccaccgccg    1500
ccacggccgc agaaaagtac aaacaccgag gggagggaga gcgcaaagac attgtttcat    1560
cctccatgcc aaggccaaac agagaggagc ctgtggacag ccggacgccc gtgaccgaga    1620
gagttagctg actttacacg gagcggattg caaagcaaac caacaagaat aaaggcagct    1680
gttgtctctt ctccttatgg gtagggctct gacaaagctt cccgattaac tgaaataaaa    1740
aatatttttt tttctttcag taaacttaga gtttcgtggc ttcagggtgg gagtagttgg    1800
agcattgggg atgttttttct taccgacaag cacagtcagg ttgaagacct aaccagggcc    1860
agaagtagct ttgcactttt ctaaactagg ctccttcaac aaggcttgct gcagatacta    1920
ctgaccagac aagctgttga ccaggcacct cccctcccgc ccaaacctttt cccccatgtg    1980 gtcgttagag acagagcgac agagcagttg agaggacact cccgttttcg gtgccatcag    2040
tgccccgtct acagctcccc cagctccccc cacctccccc actcccaacc acgttgggac    2100
agggaggtgt gaggcaggag agacagttgg attctttaga gaagatggat atgaccagtg    2160
gctatggcct gtgcgatccc acccgtggtg gctcaagtct ggccccacac cagcccccaat    2220 ccaaaactgg caaggacgct tcacaggaca ggaaagtggc acctgtctgc tccagctctg    2280
gcatggctag gaggggggag tcccttgaac tactgggtgt agactggcct gaaccacagg    2340
agaggatggc ccagggtgag gtggcatggt ccattctcaa gggacgtcct ccaacgggtg    2400
gcgctagagg ccatggaggc agtaggacaa ggtgcaggca ggctggcctg ggtcaggcc    2460 gggcagagca cagcggggtg agagggattc ctaatcactc agagcagtct gtgacttagt    2520
ggacagggga gggggcaaag ggggaggaga agaaaatgtt cttccagtta ctttccaatt    2580
ctcctttagg gacagcttag aattatttgc actattgagt cttcatgttc ccacttcaaa    2640
acaaacagat gctctgagag caaactggct tgaattggtg acatttagtc cctcaagcca    2700
ccagatgtga cagtgttgag aactacctgg atttgtatat atacctgcgc ttgttttaaa    2760
gtgggctcag cacatagggt tcccacgaag ctccgaaact ctaagtgttt gctgcaattt    2820
tataaggact tcctgattgg tttctcttct ccccttccat ttctgccttt tgttcatttc    2880
atcctttcac ttctttccct tcctccgtcc tcctccttcc tagttcatcc cttctcttcc    2940
aggcagccgc ggtgcccaac cacacttgtc ggctccagtc cccagaactc tgcctgccct    3000
ttgtcctcct gctgccagta ccagcccac cctgttttga gccctgagga ggccttgggc    3060
tctgctgagt ccgacctggc ctgtctgtga agagcaagag agcagcaagg tcttgctctc    3120
ctaggtagcc ccctcttccc tggtaagaaa aagcaaaagg catttcccac cctgaacaac    3180
gagccttttc acccttctac tctagagaag tggactggag gagctgggcc cgatttggta    3240
gttgaggaaa gcacagaggc ctcctgtggc ctgccagtca tcgagtgcc caacaggggc    3300 tccatgccag ccgaccttga cctcactcag aagtccagag tctagcgtag tgcagcaggg    3360
cagtagcggt accaatgcag aactcccaag acccgagctg gaccagtac ctgggtcccc    3420 agcccttcct ctgctcccccc ttttcccctcg agttcttct tgaatggcaa tgttttgctt    3480
ttgctcgatg cagacagggg gccagaacac cacacatttc actgtctgtc tggtccatag    3540
ctgtggtgta ggggcttaga ggcatgggct tgctgtgggt ttttaattga tcagttttca    3600
tgtgggatcc catcttttta acctctgttc aggaagtcct tatctagctg catatcttca    3660
tcatattggt atatcctttt ctgtgtttac agagatgtct cttatatcta aatctgtcca    3720
```

```
actgagaagt accttatcaa agtagcaaat gagacagcag tcttatgctt ccagaaacac    3780
ccacaggcat gtcccatgtg agctgctgcc atgaactgtc aagtgtgtgt tgtcttgtgt    3840
atttcagtta ttgtccctgg cttccttact atggtgtaat catgaaggag tgaaacatca    3900
tagaaactgt ctagcacttc cttgccagtc tttagtgatc aggaaccata gttgacagtt    3960
ccaatcagta gcttaagaaa aaaccgtgtt tgtctcttct ggaatggtta aagtgagggg    4020
agtttgcccc gttctgtttg tagagtctca tagttggact ttctagcata tatgtgtcca    4080
tttccttatg ctgtaaaagc aagtcctgca accaaactcc catcagccca atccctgatc    4140
cctgatccct tccacctgct ctgctgatga ccccccagc ttcacttctg actcttcccc    4200
aggaagggaa gggggtcag aagagagggt gagtcctcca gaactcttcc tccaaggaca    4260
gaaggctcct gccccatag tggcctcgaa ctcctggcac taccaaagga cacttatcca    4320
cgagagcgca gcatccgacc aggttgtcac tgagaagatg tttattttgg tcagttgggt    4380
ttttatgtat tatacttagt caaatgtaat gtggcttctg gaatcattgt ccagagctgc    4440
ttccccgtca cctgggcgtc atctggtcct ggtaagagga gtgcgtggcc caccaggccc    4500
ccctgtcacc catgacagtt cattcagggc cgatggggca gtcgtggttg gaacacagc    4560 atttcaagcg tcactttatt tcattcgggc cccacctgca gctccctcaa agaggcagtt    4620
gcccagcctc tttcccttcc agtttattcc agagctgcca gtggggcctg aggctcctta    4680
gggttttctc tctatttccc cctttcttcc tcattccctc gtctttccca aaggcatcac    4740
gagtcagtcg cctttcagca ggcagccttg gcggtttatc gccctggcag gcaggggccc    4800
tgcagctctc atgctgcccc tgccttgggg tcaggttgac aggaggttgg agggaaagcc    4860
ttaagctgca ggattctcac cagctgtgtc cggcccagtt ttggggtgtg acctcaattt    4920
caattttgtc tgtacttgaa cattatgaag atgggggcct ctttcagtga atttgtgaac    4980
agcagaattg accgacagct ttccagtacc catgggcta ggtcattaag cccacatcca    5040
cagtctcccc caccccttgtt ccagttgtta gttactacct cctctcctga caatactgta    5100
tgtcgtcgag ctcccccccag gtctaccccct cccggcccctg cctgctggtg ggcttgtcat    5160
agccagtggg attgccggtc ttgacagctc agtgagctgg agatacttgg tcacagccag    5220
gcgctagcac agctcccttc tgttgatgct gtattcccat atcaaaagac acagggggaca    5280 cccagaaacg ccacatcccc caatccatca gtgccaaact agccaacggc cccagcttct    5340
cagctcgctg gatggcggaa gctgctactc gtgagcgcca gtgcgggtgc agacaatctt    5400
ctgttgggtg gcatcattcc aggcccgaag catgaacagt gcacctggga cagggagcag    5460
ccccaaattg tcacctgctt ctctgcccag cttttcattg ctgtgacagt gatggcgaaa    5520
gagggtaata accagacaca aactgccaag ttgggtggag aaaggagttt ctttagctga    5580
cagaatctct gaattttaaa tcacttagta agcggctcaa gcccaggagg gagcagaggg    5640
atacgagcga gtcccctgc gcgggaccat ctggaattgg tttagcccaa gtggagcctg    5700
acagccagaa ctctgtgtcc cccgtctaac cacagctcct tttccagagc attccagtca    5760
ggctctctgg gctgactggg ccaggggagg ttacaggtac cagttctttta agaagatctt    5820 tgggcatata catttttagc ctgtgtcatt gcccaaatg gattcctgtt tcaagttcac    5880
acctgcagat tctaggacct gtgtcctaga cttcagggag tcagctgttt ctagagttcc    5940
taccatggag tgggtctgga ggacctgccc ggtgggggg cagagccctg ctccctccgg    6000
gtcttcctac tcttctctct gctctgacgg gatttgttga ttctctccat tttggtgtct    6060
```

```
ttctctttta gatattgtat caatctttag aaaaggcata gtctacttgt tataaatcgt    6120
taggatactg cctcccccag ggtctaaaat tacatattag aggggaaaag ctgaacactg    6180
aagtcagttc tcaacaattt agaaggaaaa cctagaaaac atttggcaga aaattacatt    6240
tcgatgtttt tgaatgaata cgagcaagct tttacaacag tgctgatcta aaaatactta    6300
gcacttggcc tgagatgcct ggtgagcatt acaggcaagg ggaatctgga ggtagccgac    6360
ctgaggacat ggcttctgaa cctgtctttt gggagtggta tggaaggtgg agcgttcacc    6420
agtgacctgg aaggcccagc accaccctcc ttcccactct tctcatcttg acagagcctg    6480
ccccagcgct gacgtgtcag gaaaacaccc agggaactag gaaggcactt ctgcctgagg    6540
ggcagcctgc cttgcccact cctgctctgc tcgcctcgga tcagctgagc cttctgagct    6600
ggcctctcac tgcctcccca aggcccctg cctgccctgt caggaggcag aaggaagcag     6660
gtgtgagggc agtgcaagga gggagcacaa cccccagctc ccgctccggg ctccgacttg    6720
tgcacaggca gagcccagac cctggaggaa atcctacctt tgaattcaag aacatttggg    6780
gaatttggaa atctctttgc ccccaaaccc ccattctgtc ctacctttaa tcaggtcctg    6840
ctcagcagtg agagcagatg aggtgaaaag gccaagaggt ttggctcctg cccactgata    6900
gcccctctcc ccgcagtgtt tgtgtgtcaa gtggcaaagc tgttcttcct ggtgaccctg    6960
attatatcca gtaacacata gactgtgcgc ataggcctgc tttgtctcct ctatcctggg    7020
cttttgtttt gcttttttagt tttgctttta gttttttctgt cccttttatt taacgcaccg    7080
actagacaca caaagcagtt gaatttttat atatatatct gtatattgca caattataaa    7140
ctcattttgc ttgtggctcc acacacacaa aaaaagacct gttaaaatta tacctgttgc    7200
ttaattacaa tatttctgat aaccatagca taggacaagg gaaaataaaa aagaaaaaa     7260
aagaaaaaaa aacgacaaat ctgtctgctg gtcacttctt ctgtccaagc agattcgtgg    7320
tcttttcctc gcttctttca agggctttcc tgtgccaggt gaaggaggct ccaggcagca    7380
cccaggtttt gcactcttgt ttctcccgtg cttgtgaaag aggtcccaag gttctgggtg    7440
caggagcgct cccttgacct gctgaagtcc ggaacgtagt cggcacagcc tggtcgcctt    7500
ccacctctgg gagctggagt ccactggggt ggcctgactc ccccagtccc cttcccgtga    7560
cctggtcagg gtgagcccat gtggagtcag cctcgcaggc ctccctgcca gtagggtccg    7620
agtgtgtttc atccttccca ctctgtcgag cctgggggct ggagcggaga cgggaggcct    7680
ggcctgtctc ggaacctgtg agctgcacca ggtagaacgc cagggacccc agaatcatgt    7740
gcgtcagtcc aaggggtccc ctccaggagt agtgaagact ccagaaatgt ccctttcttc    7800
tcccccatcc tacgagtaat tgcatttgct tttgtaattc ttaatgagca atatctgcta    7860
gagagtttag ctgtaacagt tcttttttgat catcttttt taataattag aaacaccaaa    7920
aaaatccaga aacttgttct tccaaagcag agagcattat aatcaccagg gccaaaagct    7980
tccctccctg ctgtcattgc ttcttctgag gcctgaatcc aaaagaaaaa cagccatagg    8040
cccttttcagt ggccgggcta cccgtgagcc cttcggagga ccagggctgg ggcagcctct    8100
gggcccacat ccggggccag ctccggcgtg tgttcagtgt tagcagtggg tcatgatgct    8160
ctttcccacc cagcctggga taggggcaga ggaggcgagg aggccgttgc cgctgatgtt    8220
tggccgtgaa caggtgggtg tctgcgtgcg tccacgtgcg tgttttctga ctgacatgaa    8280
atcgacgccc gagttagcct caccggtga cctctagccc tgcccggatg gagcggggcc     8340
cacccggttc agtgtttctg gggagctgga cagtggagtg caaaaggctt gcagaacttg    8400
aagcctgctc cttcccttgc taccacggcc tcctttccgt ttgatttgtc actgcttcaa    8460
```

-continued

```
tcaataacag ccgctccaga gtcagtagtc aatgaatata tgaccaaata tcaccaggac    8520
tgttactcaa tgtgtgccga gcccttgccc atgctgggct cccgtgtatc tggacactgt    8580
aacgtgtgct gtgtttgctc cccttcccct tccttctttg cccttttactt gtctttctgg   8640 ggttttctg tttgggtttg gtttggtttt tatttctcct tttgtgttcc aaacatgagg     8700
ttctctctac tggtcctctt aactgtggtg ttgaggctta tatttgtgta attttttggtg  8760 ggtgaaagga atttttgctaa gtaaatctct tctgtgtttg aactgaagtc tgtattgtaa  8820
ctatgtttaa agtaattgtt ccagagacaa atatttctag acactttttc tttacaaaca   8880
aaagcattcg gagggagggg gatggtgact gagatgagag gggagagctg aacagatgac   8940
ccctgcccag atcagccaga agccacccaa agcagtggag cccaggagtc ccactccaag   9000
ccagcaagcc gaatagctga tgtgttgcca ctttccaagt cactgcaaaa ccaggttttg   9060
ttccgcccag tggattcttg ttttgcttcc cctccccccg agattattac caccatcccg   9120
tgcttttaag gaaaggcaag attgatgttt ccttgagggg agccaggagg ggatgtgtgt   9180
gtgcagagct gaagagctgg ggagaatggg gctgggccca cccaagcagg aggctgggac   9240
gctctgctgt gggcacaggt caggctaatg ttggcagatg cagctcttcc tggacaggcc   9300
aggtggtggg cattctctct ccaaggtgtg ccccgtgggc attactgttt aagacacttc   9360
cgtcacatcc caccccatcc tccagggctc aacactgtga catctctatt ccccacccctc  9420 cccttcccag ggcaataaaa tgaccatgga gggggcttgc actctcttgg ctgtcacccg   9480
atcgccagca aaacttagat gtgagaaaac cccttcccat tccatggcga aaacatctcc   9540
ttagaaaagc cattaccctc attaggcatg gtttttgggct cccaaaacac ctgacagccc  9600
ctccctcctc tgagaggcgg agagtgctga ctgtagtgac cattgcatgc cgggtgcagc   9660
atctggaaga gctaggcagg gtgtctgccc cctcctgagt tgaagtcatg ctcccctgtg   9720
ccagcccaga ggccgagagc tatggacagc attgccagta acacaggcca ccctgtgcag   9780
aagggagctg gctccagcct ggaaacctgt ctgaggttgg gagaggtgca cttggggcac   9840
agggagaggc cgggacacac ttagctggag atgtctctaa aagccctgta tcgtattcac   9900
cttcagtttt tgtgttttgg gacaattact ttagaaaata agtaggtcgt tttaaaaaca   9960
aaaattattg attgcttttt tgtagtgttc agaaaaaagg ttctttgtgt atagccaaat  10020
gactgaaagc actgatatat ttaaaaacaa aaggcaattt attaaggaaa tttgtaccat  10080
ttcagtaaac ctgtctgaat gtacctgtat acgtttcaaa aacacccccc ccccactgaa  10140
tccctgtaac ctatttatta tataaagagt ttgccttata aattt                   10185
```

<210> SEQ ID NO 28
<211> LENGTH: 10227
<212> TYPE: DNA
<213> ORGANISM: Homo sapiens

<400> SEQUENCE: 28

```
gggcgcgcgc tccctcctct cggagagagg gctgtggtaa aagccgtccg gaaaatgcgc     60
cgccgccgcc gccgcgccga gcggaggagg aggaggaggc gaggaggaga gactgctcca   120
taaaatacac gactcaccag ttcctgcttt gatgtgacat gtgactcccc agaatacacc   180
ttgcttctgt agaccagctc caacaggatt ccatggtagc tgggatgtta gggctcaggg   240
aagaaaagtc agaagaccag gacctccagg gcctcaagga caaacccctc aagtttaaaa   300
aggtgaagaa agataagaaa gaagagaaag agggcaagca tgagcccgtg cagccatcag   360
```

| | |
|---|---|
| cccaccactc tgctgagccc gcagaggcag gcaaagcaga gacatcagaa gggtcaggct | 420 |
| ccgccccggc tgtgccggaa gcttctgcct cccccaaaca gcggcgctcc atcatccgtg | 480 |
| accggggacc catgtatgat daccccaccc tgcctgaagg ctggacacgg aagcttaagc | 540 |
| aaaggaaatc tggccgctct gctgggaagt atgatgtgta tttgatcaat ccccagggaa | 600 |
| aagcctttcg ctctaaagtg gagttgattg cgtacttcga aaaggtaggc gacacatccc | 660 |
| tggaccctaa tgattttgac ttcacggtaa ctgggagagg gagcccctcc cggcgagagc | 720 |
| agaaaccacc taagaagccc aaatctccca agctccagg aactggcaga ggccggggac | 780 |
| gccccaaagg gagcggcacc acgagaccca aggcggccac gtcagagggt gtgcaggtga | 840 |
| aaagggtcct ggagaaaagt cctgggaagc tccttgtcaa gatgcctttt caaacttcgc | 900 |
| caggggcaa ggctgagggg ggtgggccca ccacatccac ccaggtcatg gtgatcaaac | 960 |
| gccccggcag gaagcgaaaa gctgaggccg accctcaggc cattcccaag aaacggggcc | 1020 |
| gaaagccggg gagtgtggtg gcagccgctg ccgccgaggc caaaaagaaa gccgtgaagg | 1080 |
| agtcttctat ccgatctgtg caggagaccg tactccccat caagaagcgc aagacccggg | 1140 |
| agacggtcag catcgaggtc aaggaagtgg tgaagccccg ctggtgtcc accctcggtg | 1200 |
| agaagagcgg gaaaggactg aagacctgta agagccctgg gcggaaaagc aaggagagca | 1260 |
| gccccaaggg gcgcagcagc agcgcctcct acccccccaa gaaggagcac caccaccatc | 1320 |
| accaccactc agagtcccca aaggccccg tgccactgct cccacccctg cccccacctc | 1380 |
| cacctgagcc cgagagctcc gaggaccca ccagcccccc tgagcccag acttgagca | 1440 |
| gcagcgtctg caaagaggag aagatgccca gaggaggctc actggagagc gacggctgcc | 1500 |
| ccaaggagcc agctaagact cagcccgcgg ttgccaccgc cgccacggcc gcagaaaagt | 1560 |
| acaaacaccg aggggaggga gagcgcaaag acattgtttc atcctccatg ccaaggccaa | 1620 |
| acagagagga gcctgtggac agccggacgc ccgtgaccga gagagttagc tgactttaca | 1680 |
| cggagcggat tgcaaagcaa accaacaaga ataaaggcag ctgttgtctc ttctccttat | 1740 |
| gggtagggct ctgacaaagc ttcccgatta actgaaataa aaatatttt tttttcttc | 1800 |
| agtaaactta gagtttcgtg gcttcagggt gggagtagtt ggagcattgg ggatgttttt | 1860 |
| cttaccgaca agcacagtca ggttgaagac ctaaccaggg ccagaagtag cttgcactt | 1920 |
| ttctaaacta ggctccttca acaaggcttg ctgcagatac tactgaccag acaagctgtt | 1980 |
| gaccaggcac ctcccctccc gcccaaacct ttccccatg tggtcgttag agacagagcg | 2040 |
| acagagcagt tgagaggaca ctcccgtttt cggtgccatc agtgcccgt ctacagctcc | 2100 |
| cccagctccc cccacctccc ccactcccaa ccacgttggg acagggaggt gtgaggcagg | 2160 |
| agagacagtt ggattcttta gagaagatgg atatgaccag tggctatggc ctgtgcgatc | 2220 |
| ccacccgtgg tggctcaagt ctggccccac accagcccca atccaaaact ggcaaggacg | 2280 |
| cttcacagga caggaaagtg gcacctgtct gctccagctc tggcatggct aggagggggg | 2340 |
| agtcccttga actactgggt gtagactggc ctgaaccaca ggagaggatg gcccagggtg | 2400 |
| aggtggcatg gtccattctc aagggacgtc ctccaacggg tggcgctaga ggccatggag | 2460 |
| gcagtaggac aaggtgcagg caggctgcc tgggtcagg ccgggcagag cacacgcggg | 2520 |
| tgagagggat tcctaatcac tcagagcagt ctgtgactta gtggacaggg gaggggcaa | 2580 |
| agggggagga gaagaaaatg ttcttccagt tactttccaa ttctcctta gggacagctt | 2640 |
| agaattattt gcactattga gtcttcatgt tcccacttca aaacaaacag atgctctgag | 2700 |
| agcaaactgg cttgaattgg tgacatttag tccctcaagc caccagatgt gacagtgttg | 2760 |

```
agaactacct ggatttgtat atatacctgc gcttgtttta aagtgggctc agcacatagg    2820
gttcccacga agctccgaaa ctctaagtgt ttgctgcaat tttataagga cttcctgatt    2880
ggtttctctt ctccccttcc atttctgcct tttgttcatt tcatcctttc acttctttcc    2940
cttcctccgt cctcctcctt cctagttcat cccttctctt ccaggcagcc gcggtgccca    3000
accacacttg tcggctccag tccccagaac tctgcctgcc ctttgtcctc ctgctgccag    3060
taccagcccc accctgtttt gagccctgag gaggccttgg gctctgctga gtccgacctg    3120
gcctgtctgt gaagagcaag agagcagcaa ggtcttgctc tcctaggtag ccccctcttc    3180
cctggtaaga aaaagcaaaa ggcatttccc accctgaaca acgagccttt tcacccttct    3240
actctagaga agtggactgg aggagctggg cccgatttgg tagttgagga aagcacagag    3300
gcctcctgtg gcctgccagt catcgagtgg cccaacaggg gctccatgcc agccgacctt    3360
gacctcactc agaagtccag agtctagcgt agtgcagcag ggcagtagcg gtaccaatgc    3420
agaactccca agacccgagc tgggaccagt acctgggtcc ccagcccttc ctctgctccc    3480 cctttccct cggagttctt cttgaatggc aatgttttgc ttttgctcga tgcagacagg    3540
gggccagaac accacacatt tcactgtctg tctggtccat agctgtggtg tagggggctta    3600 gaggcatggg cttgctgtgg gttttaatt gatcagtttt catgtgggat cccatctttt    3660
taacctctgt tcaggaagtc cttatctagc tgcatatctt catcatattg gtatatcctt    3720
ttctgtgttt acagagatgt ctcttatatc taaatctgtc caactgagaa gtaccttatc    3780
aaagtagcaa atgagacagc agtcttatgc ttccagaaac acccacaggc atgtcccatg    3840
tgagctgctg ccatgaactg tcaagtgtgt gttgtcttgt gtatttcagt tattgtccct    3900
ggcttcctta ctatggtgta atcatgaagg agtgaaacat catagaaact gtctagcact    3960
tccttgccag tctttagtga tcaggaacca tagttgacag ttccaatcag tagcttaaga    4020 aaaaccgtg tttgtctctt ctggaatggt tagaagtgag ggagtttgcc ccgttctgtt    4080
tgtagagtct catagttgga ctttctagca tatatgtgtc catttcctta tgctgtaaaa    4140
gcaagtcctg caaccaaact cccatcagcc caatccctga tccctgatcc cttccacctg    4200
ctctgctgat gacccccca gcttcacttc tgactcttcc ccaggaaggg aaggggggtc    4260
agaagagagg gtgagtcctc cagaactctt cctccaagga cagaaggctc ctgcccccat    4320
agtggcctcg aactcctggc actaccaaag gacacttatc cacgagagcg cagcatccga    4380
ccaggttgtc actgagaaga tgtttatttt ggtcagttgg gttttatgt attatactta    4440 gtcaaatgta atgtggcttc tggaatcatt gtccagagct gcttccccgt cacctgggcg    4500
tcatctggtc ctggtaagag gagtgcgtgg cccaccaggc cccctgtca cccatgacag    4560 ttcattcagg gccgatgggg cagtcgtggt tgggaacaca gcatttcaag cgtcactta    4620 tttcattcgg gccccacctg cagctccctc aaagaggcag ttgcccagcc tctttccctt    4680
ccagtttatt ccagagctgc cagtggggcc tgaggctcct tagggttttc tctctatttc    4740
ccccttcttt cctcattccc tcgtctttcc caaaggcatc acgagtcagt cgcctttcag    4800
caggcagcct tggcggttta tcgccctggc aggcaggggc cctgcagctc tcatgctgcc    4860
cctgccttgg ggtcaggttg acaggaggtt ggagggaaag ccttaagctg caggattctc    4920
accagctgtg tccggcccag ttttgggtg tgacctcaat ttcaattttg tctgtacttg    4980
aacattatga agatgggggc ctctttcagt gaatttgtga acagcagaat tgaccgcacg    5040
ctttccagta cccatggggc taggtcatta aggccacatc cacagtctcc cccacccttg    5100
```

```
ttccagttgt tagttactac ctcctctcct gacaatactg tatgtcgtcg agctcccccc    5160
aggtctaccc ctcccggccc tgcctgctgg tgggcttgtc atagccagtg ggattgccgg    5220
tcttgacagc tcagtgagct ggagatactt ggtcacagcc aggcgctagc acagctccct    5280
tctgttgatg ctgtattccc atatcaaaag acacaggga cacccagaaa cgccacatcc    5340
cccaatccat cagtgccaaa ctagccaacg gccccagctt ctcagctcgc tggatggcgg    5400
aagctgctac tcgtgagcgc cagtgcgggt gcagacaatc ttctgttggg tggcatcatt    5460
ccaggcccga agcatgaaca gtgcacctgg gacagggagc agccccaaat tgtcacctgc    5520
ttctctgccc agcttttcat tgctgtgaca gtgatggcga agagggtaa taaccagaca    5580
caaactgcca agttgggtgg agaaaggagt ttctttagct gacagaatct ctgaatttta    5640
aatcacttag taagcggctc aagcccagga gggagcagag ggatacgagc ggagtcccct    5700
gcgcgggacc atctggaatt ggtttagccc aagtggagcc tgacagccag aactctgtgt    5760
cccccgtcta accacagctc cttttccaga gcattccagt caggctctct gggctgactg    5820
ggccagggga ggttacaggt accagttctt taagaagatc tttgggcata tacatttta    5880
gcctgtgtca ttgccccaaa tggattcctg tttcaagttc acacctgcag attctaggac    5940
ctgtgtccta gacttcaggg agtcagctgt ttctagagtt cctaccatgg agtgggtctg    6000
gaggacctgc ccggtggggg ggcagagccc tgctccctcc gggtcttcct actcttctct    6060
ctgctctgac gggatttgtt gattctctcc attttggtgt cttctctttt tagatattgt    6120
atcaatcttt agaaaaggca tagtctactt gttataaatc gttaggatac tgcctccccc    6180
agggtctaaa attacatatt agaggggaaa agctgaacac tgaagtcagt tctcaacaat    6240
ttagaaggaa aacctagaaa acatttggca gaaaattaca tttcgatgtt tttgaatgaa    6300
tacgagcaag cttttacaac agtgctgatc taaaaatact tagcacttgg cctgagatgc    6360
ctggtgagca ttacaggcaa ggggaatctg gaggtagccg acctgaggac atggcttctg    6420
aacctgtctt ttgggagtgg tatggaaggt ggagcgttca ccagtgacct ggaaggccca    6480
gcaccaccct ccttcccact cttctcatct tgacagagcc tgccccagcg ctgacgtgtc    6540
aggaaaacac ccagggaact aggaaggcac ttctgcctga ggggcagcct gccttgccca    6600
ctcctgctct gctcgcctcg gatcagctga gccttctgag ctggcctctc actgcctccc    6660
caaggccccc tgcctgccct gtcaggaggc agaaggaagc aggtgtgagg gcagtgcaag    6720
gagggagcac aaccccagc tcccgctccg ggctccgact tgtgcacagg cagagcccag    6780
accctggagg aaatcctacc tttgaattca agaacatttg gggaatttgg aaatctcttt    6840
gcccccaaac ccccattctg tcctacccttt aatcaggtcc tgctcagcag tgagagcaga    6900
tgaggtgaaa aggccaagag gtttggctcc tgcccactga tagcccctct ccccgcagtg    6960
tttgtgtgtc aagtggcaaa gctgttcttc ctggtgaccc tgattatatc cagtaacaca    7020
tagactgtgc gcataggcct gcttgtctc ctctatcctg ggcttttgtt ttgcttttta    7080
gttttgcttt tagtttttct gtccctttta tttaacgcac cgactagaca cacaaagcag    7140
ttgaattttt atatatatat ctgtatattg cacaattata aactcatttt gcttgtggct    7200
ccacacacac aaaaaaagac ctgttaaaat tatacctgtt gcttaattac aatatttctg    7260
ataaccatag cataggacaa gggaaaataa aaaagaaaa aaagaaaaa aaacgacaa     7320
atctgtctgc tggtcacttc ttctgtccaa gcagattcgt ggtcttttcc tcgcttcttt    7380
caagggcttt cctgtgccag gtgaaggagg ctccaggcag cacccaggtt ttgcactctt    7440
gtttctcccg tgcttgtgaa agaggtccca aggttctggg tgcaggagcg ctcccttgac    7500
```

```
ctgctgaagt ccggaacgta gtcggcacag cctggtcgcc ttccacctct gggagctgga    7560
gtccactggg gtggcctgac tcccccagtc cccttcccgt gacctggtca gggtgagccc    7620
atgtggagtc agcctcgcag gcctccctgc cagtagggtc cgagtgtgtt tcatccttcc    7680
cactctgtcg agcctggggg ctggagcgga cgggaggc ctggcctgtc tcggaacctg      7740
tgagctgcac caggtagaac gccagggacc ccagaatcat gtgcgtcagt ccaaggggtc    7800
ccctccagga gtagtgaaga ctccagaaat gtcccttttct tctcccccat cctacgagta   7860
attgcatttg cttttgtaat tcttaatgag caatatctgc tagagagttt agctgtaaca    7920
gttcttttttg atcatctttt tttaataatt agaaacacca aaaaaatcca gaaacttgtt   7980
cttccaaagc agagagcatt ataatcacca gggccaaaag cttccctccc tgctgtcatt    8040
gcttcttctg aggcctgaat ccaaaagaaa aacagccata ggccctttca gtggccgggc    8100
tacccgtgag cccttcggag gaccagggct ggggcagcct ctgggcccac atccggggcc    8160
agctccggcg tgtgttcagt gttagcagtg ggtcatgatg ctctttccca cccagcctgg    8220
gatagggggca gaggaggcga ggaggccgtt gccgctgatg tttggccgtg aacaggtggg   8280
tgtctgcgtg cgtccacgtg cgtgttttct gactgacatg aaatcgacgc ccagttagc    8340
ctcacccggt gacctctagc cctgcccgga tggagcgggg cccacccggt tcagtgtttc    8400
tggggagctg gacagtggag tgcaaaaggc ttgcagaact tgaagcctgc tccttccctt    8460
gctaccacgg cctcctttcc gtttgatttg tcactgcttc aatcaataac agccgctcca    8520
gagtcagtag tcaatgaata tatgaccaaa tatcaccagg actgttactc aatgtgtgcc    8580
gagcccttgc ccatgctggg ctcccgtgta tctggacact gtaacgtgtg ctgtgtttgc    8640
tcccctcccc cttccttctt tgcccttttac ttgtctttct gggggtttttc tgtttgggtt   8700
tggtttggtt tttatttctc cttttgtgtt ccaaacatga ggttctctct actggtcctc    8760
ttaactgtgg tgttgaggct tatatttgtg taattttttgg tgggtgaaag gaattttgct   8820
aagtaaatct cttctgtgtt tgaactgaag tctgtattgt aactatgttt aaagtaattg    8880
ttccagagac aaatatttct agacacttttt tctttacaaa caaaagcatt cggagggagg   8940
gggatggtga ctgagatgag aggggagagc tgaacagatg cccctgccc agatcagcca    9000
gaagccaccc aaagcagtgg agcccaggag tcccactcca agccagcaag ccgaatagct    9060
gatgtgttgc cactttccaa gtcactgcaa aaccaggttt tgttccgccc agtggattct    9120
tgttttgctt cccctccccc cgagattatt accaccatcc cgtgctttta aggaaaggca    9180
agattgatgt ttccttgagg ggagccagga ggggatgtgt gtgtgcagag ctgaagagct    9240
ggggagaatg gggctgggcc cacccaagca ggaggctggg acgctctgct gtgggcacag    9300
gtcaggctaa tgttggcaga tgcagctctt cctggacagg ccaggtggtg ggcattctct    9360
ctccaaggtg tgccccgtgg gcattactgt ttaagacact tccgtcacat cccaccccat    9420
cctccagggc tcaacactgt gacatctcta ttccccaccc tcccctttccc agggcaataa   9480
aatgaccatg gagggggctt gcactctctt ggctgtcacc cgatcgccag caaaacttag    9540
atgtgagaaa accccttccc attccatggc gaaaacatct ccttagaaaa gccattaccc    9600
tcattaggca tggttttggg ctcccaaaac acctgacagc ccctccctcc tctgagaggc    9660
ggagagtgct gactgtagtg accattgcat gccgggtgca gcatctggaa gagctaggca    9720
gggtgtctgc cccctcctga gttgaagtca tgctcccctg tgccagccca gaggccgaga    9780
gctatggaca gcattgccag taacacaggc caccctgtgc agaagggagc tggctccagc    9840
```

```
ctggaaacct gtctgaggtt gggagaggtg cacttggggc acagggagag gccgggacac    9900
acttagctgg agatgtctct aaaagccctg tatcgtattc accttcagtt tttgtgtttt    9960
gggacaatta ctttagaaaa taagtaggtc gttttaaaaa caaaaattat tgattgcttt   10020
tttgtagtgt tcagaaaaaa ggttctttgt gtatagccaa atgactgaaa gcactgatat   10080
atttaaaaac aaaaggcaat ttattaagga aatttgtacc atttcagtaa acctgtctga   10140
atgtacctgt atacgtttca aaaacacccc cccccactg aatccctgta acctatttat    10200
tatataaaga gtttgcctta taaattt                                        10227
```

<210> SEQ ID NO 29
<211> LENGTH: 10227
<212> TYPE: DNA
<213> ORGANISM: Homo sapiens

<400> SEQUENCE: 29

```
gggcgcgcgc gctccctcct ctcggagagg gctgtggtaa aagccgtccg gaaaatggcc      60
gccgccgccg ccgccgccga gcggaggagg aggaggaggc gaggaggaga gactgctcca    120
taaaaataca gactcaccag ttcctgcttt gatgtgacat gtgactcccc agaatacacc    180
ttgcttctgt agaccagctc caacaggatt ccatggtagc tgggatgtta gggctcaggg    240
aagaaaagtc agaagaccag gacctccagg gcctcaagga caaacccctc aagtttaaaa    300
aggtgaagaa agataagaaa gaagagaaag agggcaagca tgagcccgtg cagccatcag    360
cccaccactc tgctgagccc gcagaggcag gcaaagcaga gacatcagaa gggtcaggct    420 ccgcccggc tgtgccggaa gcttctgcct ccccaaaca gcggcgctcc atcatccgtg     480
accggggacc catgtatgat gaccccaccc tgcctgaagg ctggacacgg aagcttaagc    540
aaaggaaatc tggccgctct gctgggaagt atgatgtgta tttgatcaat ccccagggaa    600
aagcctttcg ctctaaagtg gagttgattg cgtacttcga aaaggtaggc gacacatccc    660
tggaccctaa tgattttgac ttcacggtaa ctgggagagg gagcccctcc cggcgagagc    720
agaaaccacc taagaagccc aaatctccca agctccagg aactggcaga ggccggggac    780
gccccaaagg gagcggcacc acgagaccca aggcggccac gtcagagggt gtgcaggtga    840
aaagggtcct ggagaaaagt cctgggaagc tccttgtcaa gatgcctttt caaacttcgc    900 caggggcaa ggctgagggg ggtggggcca ccacatccac ccaggtcatg gtgatcaaac    960
gccccggcag gaagcgaaaa gctgaggccg accctcaggc cattcccaag aaacggggcc   1020
gaaagccggg gagtgtggtg gcagccgctg ccgccgaggc caaaaagaaa gccgtgaagg   1080
agtcttctat ccgatctgtg caggagaccg tactccccat caagaagcgc aagacccggg   1140
agacggtcag catcgaggtc aaggaagtgg tgaagcccct gctggtgtcc accctcggtg   1200
agaagagcgg gaaaggactg aagacctgta agagccctgg gcggaaaagc aaggagagca   1260
gcccaagggg gcgcagcagc agcgcctcct caccccccaa gaaggagcac caccaccatc   1320
accaccactc agagtcccca aaggccccg tgccactgct cccaccctg ccccaccctc     1380 cacctgagcc cgagagctcc gaggacccca ccagcccccc tgagcccag acttgagca     1440 gcagcgtctg caaagaggag aagatgccca gaggaggctc actggagagc gacggctgcc   1500
ccaaggagcc agctaagact cagcccgcgg ttgccaccgc cgccacggcc gcagaaaagt   1560
acaaacaccg aggggaggga gagcgcaaag acattgtttc atcctccatg ccaaggccaa   1620
acagagagga gcctgtggac agccggacgc ccgtgaccga gagagttagc tgactttaca   1680
cggagcggat tgcaaagcaa accaacaaga ataaaggcag ctgttgtctc ttctccttat   1740
```

```
gggtagggct ctgacaaagc ttcccgatta actgaaataa aaaatatttt tttttctttc   1800
agtaaactta gagtttcgtg gcttcagggt gggagtagtt ggagcattgg ggatgttttt   1860
cttaccgaca agcacagtca ggttgaagac ctaaccaggg ccagaagtag ctttgcactt   1920
ttctaaacta ggctccttca acaaggcttg ctgcagatac tactgaccag acaagctgtt   1980
gaccaggcac ctcccctccc gcccaaacct tccccccatg tggtcgttag agacagagcg   2040
acagagcagt tgagaggaca ctcccgtttt cggtgccatc agtgcccgt ctacagctcc    2100 cccagctccc cccacctccc ccactcccaa ccacgttggg acagggaggt gtgaggcagg   2160
agagacagtt ggattctttta gagaagatgg atatgaccag tggctatggc ctgtgcgatc   2220
ccacccgtgg tggctcaagt ctggccccac accagcccca atccaaaact ggcaaggacg   2280
cttcacagga caggaaagtg gcacctgtct gctccagctc tggcatggct aggagggggg   2340
agtcccttga actactgggt gtagactggc ctgaaccaca ggagaggatg cccagggtg    2400 aggtggcatg gtccattctc aagggacgtc ctccaacggg tggcgctaga ggccatggag   2460
gcagtaggac aaggtgcagg caggctggcc tggggtcagg ccgggcagag cacagcgggg   2520
tgagagggat tcctaatcac tcagagcagt ctgtgactta gtggacaggg gaggggcaa    2580 aggggagga gaagaaaatg ttcttccagt tactttccaa ttctccttta gggacagctt    2640
agaattattt gcactattga gtcttcatgt tcccacttca aaacaaacag atgtctgag    2700 agcaaactgg cttgaattgg tgacatttag tccctcaagc caccagatgt gacagtgttg   2760
agaactacct ggatttgtat atatacctgc gcttgttta aagtgggctc agcacatagg     2820
gttcccacga agctccgaaa ctctaagtgt ttgctgcaat tttataagga cttcctgatt   2880
ggtttctctt ctccccttcc atttctgcct tttgttcatt tcatcctttc acttctttcc   2940
cttcctccgt cctcctcctt cctagttcat cccttctctt ccaggcagcc gcggtgccca   3000
accacacttg tcggctccag tccccagaac tctgcctgcc cttttgtcctc ctgctgccag   3060 taccagcccc accctgtttt gagccctgag gaggccttgg gctctgctga gtccgacctg    3120
gcctgtctgt gaagagcaag agagcagcaa ggtcttgctc tcctaggtag cccctcttc     3180 cctggtaaga aaaagcaaaa ggcatttccc accctgaaca cgagcctttt tcacccttct   3240
actctagaga agtggactgg aggagctggg cccgatttgg tagttgagga aagcacagag   3300
gcctcctgtg gcctgccagt catcgagtgg cccaacaggg gctccatgcc agccgacctt   3360
gacctcactc agaagtccag agtctagcgt agtgcagcag ggcagtagcg gtaccaatgc   3420
agaactccca agacccgagc tgggaccagt acctgggtcc ccagcccttc ctctgctccc   3480 cctttccct cggagttctt cttgaatggc aatgttttgc ttttgctcga tgcagacagg    3540
gggccagaac accacacatt tcactgtctg tctggtccat agctgtggtg taggggctta   3600
gaggcatggg cttgctgtgg gttttttaatt gatcagtttt catgtgggat cccatctttt   3660
taacctctgt tcaggaagtc cttatctagc tgcatatctt catcatattg gtatatcctt   3720
ttctgtgttt acagagatgt ctcttatatc taaatctgtc caactgagaa gtaccttatc   3780
aaagtagcaa atgagacagc agtcttatgc ttccagaaac acccacaggc atgtcccatg   3840
tgagctgctg ccatgaactg tcaagtgtgt gttgtcttgt gtatttcagt tattgtccct   3900
ggcttcctta ctatggtgta atcatgaagg agtgaaacat catagaaact gtctagcact   3960
tccttgccag tctttagtga tcaggaacca tagttgacag ttccaatcag tagcttaaga   4020
aaaaaccgtg tttgtctctt ctggaatggt tagaagtgag ggagtttgcc ccgttctgtt   4080
```

| | |
|---|---|
| tgtagagtct catagttgga cttcctagca tatatgtgtc catttcctta tgctgtaaaa | 4140 |
| gcaagtcctg caaccaaact cccatcagcc caatccctga tccctgatcc cttccacctg | 4200 |
| ctctgctgat gaccccccca gcttcacttc tgactcttcc ccaggaaggg aaggggggtc | 4260 |
| agaagagagg gtgagtcctc cagaactctt cctccaagga cagaaggctc ctgcccccat | 4320 |
| agtggcctcg aactcctggc actaccaaag gacacttatc cacgagagcg cagcatccga | 4380 |
| ccaggttgtc actgagaaga tgtttatttt ggtcagttgg ttttttatgt attatactta | 4440 |
| gtcaaatgta atgtggcttc tggaatcatt gtccagagct gcttccccgt cacctgggcg | 4500 |
| tcatctggtc ctggtaagag gagtgcgtgg cccaccaggc cccctgtca cccatgacag | 4560 |
| ttcattcagg gccgatgggg cagtcgtggt tgggaacaca gcatttcaag cgtcactttta | 4620 |
| tttcattcgg gccccacctg cagctccctc aaagaggcag ttgcccagcc tctttccctt | 4680 |
| ccagtttatt ccagagctgc cagtgggggcc tgaggctcct tagggttttc tctctatttc | 4740 |
| cccctttctt cctcattccc tcgtcttccc caaaggcatc acgagtcagt cgcctttcag | 4800 |
| caggcagcct tggcggttta tcgccctggc aggcaggggc cctgcagctc tcatgctgcc | 4860 |
| cctgccttgg ggtcaggttg acaggaggtt ggagggaaag ccttaagctg caggattctc | 4920 |
| accagctgtg tccggcccag ttttggggtg tgacctcaat ttcaatttg tctgtacttg | 4980 |
| aacattatga agatgggggc ctctttcagt gaatttgtga acagcagaat tgaccgacag | 5040 |
| cttttccagta cccatgggggc taggtcatta aggccacatc cacagtctcc cccacccttg | 5100 |
| ttccagttgt tagttactac ctcctctcct gacaatactg tatgtcgtcg agctcccccc | 5160 |
| aggtctaccc ctcccggccc tgcctgctgg tgggcttgtc atagccagtg ggattgccgg | 5220 |
| tcttgacagc tcagtgagct ggagatactt ggtcacagcc aggcgctagc acagctccct | 5280 |
| tctgttgatg ctgtattccc atatcaaaag acacagggga cacccagaaa cgccacatcc | 5340 |
| cccaatccat cagtgccaaa ctagccaacg gccccagctt ctcagctcgc tggatggcgg | 5400 |
| aagctgctac tcgtgagcgc cagtgcgggt gcagacaatt ttctgttggg tggcatcatt | 5460 |
| ccaggcccga agcatgaaca gtgcacctgg gacagggagc agccccaaat tgtcacctgc | 5520 |
| ttctctgccc agcttttcat tgctgtgaca gtgatggcga aagagggtaa taaccagaca | 5580 |
| caaactgcca agttgggtgg agaaaggagt ttctttagct gacagaatct ctgaatttta | 5640 |
| aatcacttag taagcggctc aagcccagga gggagcagag ggatacgagc ggagtcccct | 5700 |
| gcgcgggacc atctggaatt ggtttagccc aagtggagcc tgacagccag aactctgtgt | 5760 |
| cccccgtcta accacagctc cttttccaga gcattccagt caggctctct gggctgactg | 5820 |
| ggccagggga ggttacaggt accagttctt taagaagatc tttgggcata tacatttta | 5880 |
| gcctgtgtca ttgccccaaa tggattcctg tttcaagttc acacctgcag attctaggac | 5940 |
| ctgtgtccta gacttcaggg agtcagctgt ttctagagtt cctaccatgg agtgggtctg | 6000 |
| gaggacctgc ccggtggggg ggcagagccc tgctccctcc gggtcttcct actcttctct | 6060 |
| ctgctctgac gggatttgtt gattctctcc attttggtgt ctttctcttt tagatattgt | 6120 |
| atcaatcttt agaaaaggca tagtctactt gttataaatc gttaggatac tgcctccccc | 6180 |
| agggtctaaa attacatatt agaggggaaa agctgaacac tgaagtcagt tctcaacaat | 6240 |
| ttagaaggaa aacctagaaa acatttggca gaaaattaca tttcgatgtt tttgaatgaa | 6300 |
| tacgagcaag cttttacaac agtgctgatc taaaaatact tagcacttgg cctgagatgc | 6360 |
| ctggtgagca ttacaggcaa ggggaatctg gaggtagccg acctgaggac atggcttctg | 6420 |
| aacctgtctt ttgggagtgg tatggaaggt ggagcgttca ccagtgacct ggaaggccca | 6480 |

```
gcaccaccct ccttcccact cttctcatct tgacagagcc tgcccagcg ctgacgtgtc      6540 aggaaaacac ccagggaact aggaaggcac ttctgcctga ggggcagcct gccttgccca      6600
ctcctgctct gctcgcctcg gatcagctga gccttctgag ctggcctctc actgcctccc      6660
caaggccccc tgcctgccct gtcaggaggc agaaggaagc aggtgtgagg gcagtgcaag      6720
gagggagcac aaccccagc tcccgctccg ggctccgact tgtgcacagg cagagcccag       6780
accctggagg aaatcctacc tttgaattca agaacatttg gggaatttgg aaatctcttt      6840
gcccccaaac ccccattctg tcctaccttt aatcaggtcc tgctcagcag tgagagcaga      6900
tgaggtgaaa aggccaagag gtttggctcc tgcccactga tagcccctct ccccgcagtg      6960
tttgtgtgtc aagtggcaaa gctgttcttc ctggtgaccc tgattatatc cagtaacaca      7020
tagactgtgc gcataggcct gctttgtctc ctctatcctg ggcttttgtt ttgcttttta      7080
gttttgcttt tagtttttct gtcccttttta tttaacgcac cgactagaca cacaaagcag     7140 ttgaatttttt atatatatat ctgtatattg cacaattata aactcatttt gcttgtggct     7200
ccacacacac aaaaaaagac ctgttaaaat tatacctgtt gcttaattac aatatttctg      7260
ataaccatag cataggacaa gggaaaataa aaaagaaaaa aaaagaaaaa aaaacgacaa      7320
atctgtctgc tggtcacttc ttctgtccaa gcagattcgt ggtcttttcc tcgcttcttt      7380
caagggcttt cctgtgccag gtgaaggagg ctccaggcag cacccaggtt ttgcactctt      7440
gtttctcccg tgcttgtgaa agaggtccca aggttctggg tgcaggagcg ctcccttgac      7500
ctgctgaagt ccggaacgta gtcggcacag cctggtcgcc ttccacctct gggagctgga      7560
gtccactggg gtggcctgac tcccccagtc cccttcccgt gacctggtca gggtgagccc      7620
atgtggagtc agcctcgcag gcctccctgc cagtagggtc cgagtgtgtt tcatccttcc      7680
cactctgtcg agcctggggg ctggagcgga gacgggaggc ctggcctgtc tcggaacctg      7740
tgagctgcac caggtagaac gccagggacc ccagaatcat gtgcgtcagt ccaaggggtc      7800
ccctccagga gtagtgaaga ctccagaaat gtccctttct tctcccccat cctacgagta      7860
attgcatttg cttttgtaat tcttaatgag caatatctgc tagagagttt agctgtaaca      7920
gttctttttg atcatctttt tttaataatt agaaacacca aaaaaatcca gaaacttgtt      7980
cttccaaagc agagagcatt ataatcacca gggccaaaag cttccctccc tgctgtcatt      8040
gcttcttctg aggcctgaat ccaaaagaaa aacagccata ggcccttttca gtggccgggc     8100 tacccgtgag cccttcggag gaccagggct ggggcagcct ctgggccac atccggggcc       8160 agctccggcg tgtgttcagt gttagcagtg ggtcatgatg ctctttccca cccagcctgg      8220
gataggggca gaggaggcga ggaggccgtt gccgctgatg tttggccgtg aacaggtggg      8280
tgtctgcgtg cgtccacgtg cgtgttttct gactgacatg aaatcgacgc ccgagttagc      8340
ctcacccggt gacctctagc cctgcccgga tggagcgggg cccacccggt tcagtgtttc      8400
tggggagctg gacagtggag tgcaaaaggc ttgcagaact tgaagcctgc tccttccctt      8460
gctaccacgg cctccttttcc gtttgatttg tcactgcttc aatcaataac agccgctcca    8520
gagtcagtag tcaatgaata tatgaccaaa tatcaccagg actgttactc aatgtgtgcc      8580
gagcccttgc ccatgctggg ctcccgtgta tctggacact gtaacgtgtg ctgtgtttgc      8640
tccccttccc cttccttctt tgcccttttac ttgtctttct ggggtttttc tgtttgggtt    8700
tggtttggtt tttatttctc cttttgtgtt ccaaacatga ggttctctct actggtcctc      8760
ttaactgtgg tgttgaggct tatatttgtg taattttttgg tgggtgaaag gaattttgct    8820
```

```
aagtaaatct cttctgtgtt tgaactgaag tctgtattgt aactatgttt aaagtaattg    8880
ttccagagac aaatatttct agacactttt tctttacaaa caaaagcatt cggagggagg    8940
gggatggtga ctgagatgag aggggagagc tgaacagatg acccctgccc agatcagcca    9000
gaagccaccc aaagcagtgg agcccaggag tcccactcca agccagcaag ccgaatagct    9060
gatgtgttgc cactttccaa gtcactgcaa aaccaggttt tgttccgccc agtggattct    9120
tgttttgctt cccctccccc cgagattatt accaccatcc cgtgctttta aggaaaggca    9180
agattgatgt ttccttgagg ggagccagga ggggatgtgt gtgtgcagag ctgaagagct    9240
ggggagaatg gggctgggcc cacccaagca ggaggctggg acgctctgct gtgggcacag    9300
gtcaggctaa tgttggcaga tgcagctctt cctggacagg ccaggtggtg ggcattctct    9360
ctccaaggtg tgccccgtgg gcattactgt ttaagacact tccgtcacat cccaccccat    9420
cctccagggc tcaacactgt gacatctcta ttccccaccc tccccttccc agggcaataa    9480
aatgaccatg gagggggctt gcactctctt ggctgtcacc cgatcgccag caaaacttag    9540
atgtgagaaa accccttccc attccatggc gaaaacatct ccttagaaaa gccattaccc    9600
tcattaggca tggttttggg ctcccaaaac acctgacagc ccctccctcc tctgagaggc    9660
ggagagtgct gactgtagtg accattgcat gccgggtgca gcatctggaa gagctaggca    9720
gggtgtctgc cccctcctga gttgaagtca tgctcccctg tgccagccca gaggccgaga    9780
gctatggaca gcattgccag taacacaggc caccctgtgc agaagggagc tggctccagc    9840
ctggaaacct gtctgaggtt gggagaggtg cacttggggc acaggggagag gccgggacac    9900 acttagctgg agatgtctct aaaagccctg tatcgtattc accttcagtt tttgtgtttt    9960
gggacaatta ctttagaaaa taagtaggtc gttttaaaaa caaaaattat tgattgcttt   10020
tttgtagtgt tcagaaaaaa ggttctttgt gtatagccaa atgactgaaa gcactgtatat   10080 atttaaaaac aaaaggcaat ttattaagga aatttgtacc atttcagtaa acctgtctga   10140
atgtacctgt atacgtttca aaacaccccc ccccccactg aatccctgta acctatttat   10200
tatataaaga gtttgcctta taaattt                                       10227
```

<210> SEQ ID NO 30
<211> LENGTH: 9
<212> TYPE: PRT
<213> ORGANISM: Homo sapiens

<400> SEQUENCE: 30

Met Val Ala Gly Met Leu Gly Leu Arg
1               5

<210> SEQ ID NO 31
<211> LENGTH: 21
<212> TYPE: PRT
<213> ORGANISM: Homo sapiens

<400> SEQUENCE: 31

Met Ala Ala Ala Ala Ala Ala Ala Pro Ser Gly Gly Gly Gly Gly Gly
1               5                   10                  15

Glu Glu Glu Arg Leu
            20

<210> SEQ ID NO 32
<211> LENGTH: 21
<212> TYPE: PRT
<213> ORGANISM: Pan troglodytes

```
<400> SEQUENCE: 32

Met Ala Ala Ala Ala Ala Ala Pro Ser Gly Gly Gly Gly Gly
1               5                   10                  15

Glu Glu Glu Arg Leu
            20

<210> SEQ ID NO 33
<211> LENGTH: 26
<212> TYPE: PRT
<213> ORGANISM: Mus musculus

<400> SEQUENCE: 33

Met Ala Ala Ala Ala Ala Thr Ala Ala Ala Ala Ala Pro Ser Gly
1               5                   10                  15

Gly Gly Gly Gly Gly Glu Glu Glu Arg Leu
            20                  25

<210> SEQ ID NO 34
<211> LENGTH: 37
<212> TYPE: PRT
<213> ORGANISM: Rattus norvegicus

<400> SEQUENCE: 34

Met Ala Ala Ala Ala Ala Ala Ala Ala Ala Ala Ala Ala Ala Ala
1               5                   10                  15

Ala Ala Ala Ala Ala Ala Ala Pro Ser Gly Gly Gly Gly Gly
            20                  25                  30

Glu Glu Glu Arg Leu
        35

<210> SEQ ID NO 35
<211> LENGTH: 21
<212> TYPE: PRT
<213> ORGANISM: Felis catus

<400> SEQUENCE: 35

Met Ala Ala Ala Ala Ala Ala Ala Pro Ser Gly Gly Gly Gly Gly
1               5                   10                  15

Glu Glu Glu Arg Leu
            20

<210> SEQ ID NO 36
<211> LENGTH: 15
<212> TYPE: PRT
<213> ORGANISM: Gallus gallus

<400> SEQUENCE: 36

Met Ala Ala Ala Ala Ala Ala Ala Ala Gly Gly Glu Glu Arg Leu
1               5                   10                  15

<210> SEQ ID NO 37
<211> LENGTH: 11
<212> TYPE: PRT
<213> ORGANISM: Xenopus laevis

<400> SEQUENCE: 37

Met Ala Ala Ala Pro Ser Gly Glu Glu Arg Leu
1               5                   10

<210> SEQ ID NO 38
<211> LENGTH: 11
<212> TYPE: PRT
```

```
<213> ORGANISM: Danio rerio

<400> SEQUENCE: 38

Met Ala Ala Ala Glu Ser Gly Glu Glu Arg Leu
1               5                   10

<210> SEQ ID NO 39
<211> LENGTH: 9
<212> TYPE: PRT
<213> ORGANISM: Fugu rubripes

<400> SEQUENCE: 39

Met Ala Ala Val Glu Ser Gly Glu Glu
1               5

<210> SEQ ID NO 40
<211> LENGTH: 13
<212> TYPE: PRT
<213> ORGANISM: Homo sapiens

<400> SEQUENCE: 40

Met Ala Ala Ala Ala Ala Gln Gly Gly Gly Gly Gly Glu
1               5                   10

<210> SEQ ID NO 41
<211> LENGTH: 14
<212> TYPE: PRT
<213> ORGANISM: Mus musculus

<400> SEQUENCE: 41

Met Ala Ala Ala Ala Ala Ala Pro Gly Gly Gly Gly Gly Glu
1               5                   10

<210> SEQ ID NO 42
<211> LENGTH: 14
<212> TYPE: PRT
<213> ORGANISM: Rattus norvegicus

<400> SEQUENCE: 42

Met Ala Ala Ala Ala Ala Ala Pro Gly Gly Gly Gly Gly Glu
1               5                   10

<210> SEQ ID NO 43
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Pro Ser Gly Gly Gly Gly Gly Gly Glu Glu Glu Arg Leu
1               5                   10

<210> SEQ ID NO 44
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
ccgagcggag gaggaggagg aggcgaggag gagagactg                                39
```

```
<210> SEQ ID NO 45
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ala Ala Pro Ser Gly Gly Gly Gly Glu Thr Val Glu Trp
1               5                   10

<210> SEQ ID NO 46
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
cgccgcgccg agcggaggag gaggaggaga gactgtgagt gg                          42

<210> SEQ ID NO 47
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
ggcgtcggcg gcgcgcgctc cctcctctcg gagagaggct gtggtaaaag ccgtccc         57

<210> SEQ ID NO 48
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Met Ala Ala Ala Ala Ala Ala Ala Pro Ser Gly Gly Gly Gly Gly Gly
1               5                   10                  15

Gly Glu Glu Glu Arg Leu
            20

<210> SEQ ID NO 49
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
gaaaatggcc gccgccgccg ccgccgcgcc gagggaggag gaggaggagg agccg           55

<210> SEQ ID NO 50
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50
```

Met Ala Ala Ala Ala Ala Ala Pro Ser Gly Gly Gly Gly Gly Glu
1               5                   10                  15

Glu Glu Arg Leu
            20

<210> SEQ ID NO 51
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
gaaaatggcc gccgccgccg ccgcgccgag cggaggagga ggaggaggcg aggaggaga      59

<210> SEQ ID NO 52
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Met Ala Ala Ala Ala Ala Ala Ala Ala Pro Ser Gly Gly Gly
1               5                   10                  15

Gly Gly Gly Glu Glu Glu Arg Leu
            20

<210> SEQ ID NO 53
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
gccgtccgga aaatggccgc cgccgccgcc gccgccgccg ccgcgccgag cggaggagga     60

<210> SEQ ID NO 54
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Met Ala Ala Ala Ala Ala Ala Ala Pro Ser Gly Gly Gly Gly Gly Gly
1               5                   10                  15

Glu Glu Glu Arg Leu
            20

<210> SEQ ID NO 55
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 55
cctcctctcg gagagggctg tggtaaaagc cgtccggaaa atc                    43
```